(12) United States Patent
Yildirim et al.

(10) Patent No.: US 11,517,639 B2
(45) Date of Patent: Dec. 6, 2022

(54) GENERATING COLD PLASMA AWAY FROM SKIN, AND ASSOCIATED SYSTEMS AND METHODS

(71) Applicant: L'Oreal, Paris (FR)

(72) Inventors: Ozgur Emek Yildirim, Bellevue, WA (US); Thi Hong Lien Planard-Luong, Chevilly Larue (FR); Matthieu Jacob, Chevilly Larue (FR); Geoffrey Deane, Bellevue, WA (US)

(73) Assignee: L'Oreal, Paris (FR)

( * ) Notice: Subject to any disclaimer, the term of this patent is extended or adjusted under 35 U.S.C. 154(b) by 507 days.

(21) Appl. No.: 16/526,899

(22) Filed: Jul. 30, 2019

(65) Prior Publication Data
US 2020/0038530 A1    Feb. 6, 2020

Related U.S. Application Data

(60) Provisional application No. 62/773,944, filed on Nov. 30, 2018, provisional application No. 62/773,984, (Continued)

(51) Int. Cl.
*A61L 2/14* (2006.01)
*A61N 1/44* (2006.01)
(Continued)

(52) U.S. Cl.
CPC .................. *A61L 2/14* (2013.01); *A61N 1/44* (2013.01); *A61B 18/042* (2013.01); *A61L 9/22* (2013.01)

(58) Field of Classification Search
CPC .................. A61B 18/042; A61B 18/14; A61B 2018/00017; A61B 2018/00452;
(Continued)

(56) References Cited

U.S. PATENT DOCUMENTS 7,633,231 B2 * 12/2009 Watson .................... A61N 1/44
                                                    219/121.36
8,343,090 B2 *  1/2013 Rooks .................. A61B 18/042
                                                    606/49

(Continued)

FOREIGN PATENT DOCUMENTS

EP    2765837 A2    8/2014
EP    2670477 B1    11/2015
(Continued)

OTHER PUBLICATIONS

International Search Report and Written Opinion, dated Dec. 17, 2019, issued in corresponding International Application No. PCT/US2019/044224, filed Jul. 30, 2019, 19 pages.
(Continued)

*Primary Examiner* — Jonathan T Kuo
(74) *Attorney, Agent, or Firm* — Christensen O'Connor Johnson Kindness PLLC

(57) ABSTRACT

A cold plasma system and method for treating a region of a biological surface is presented. In one embodiment, the system includes: a housing; an air conduit within the housing; a first electrode configured proximately along the air conduit; a second electrode configured proximately along the air conduit and opposite from the first electrode; and a source of alternating current (AC) electrically connected with the first electrode. The source of alternating current is configured to generate cold plasma in the air conduit.

7 Claims, 34 Drawing Sheets

Related U.S. Application Data filed on Nov. 30, 2018, provisional application No. 62/773,958, filed on Nov. 30, 2018, provisional application No. 62/773,969, filed on Nov. 30, 2018, provisional application No. 62/712,860, filed on Jul. 31, 2018, provisional application No. 62/712,876, filed on Jul. 31, 2018, provisional application No. 62/712,849, filed on Jul. 31, 2018, provisional application No. 62/712,873, filed on Jul. 31, 2018, provisional application No. 62/712,812, filed on Jul. 31, 2018.

(51) Int. Cl.
*A61L 9/22* (2006.01)
*A61B 18/04* (2006.01)

(58) Field of Classification Search
CPC .. A61B 2018/00583; A61H 2201/0153; A61H 2201/0221; A61H 2201/10; A61H 2201/1207; A61H 2201/50; A61H 2201/5058; A61H 2205/022; A61H 2205/023; A61H 2205/024; A61H 2205/06; A61H 2205/102; A61H 2205/12; A61H 23/0245; A61H 23/0263; A61H 7/005; A61L 2/0094; A61L 2/14; A61L 9/22; A61N 1/328; A61N 1/44; A61N 2005/0644; A61N 2005/0659; A61N 2005/0662; A61N 5/06; A61N 5/0616; A61N 5/0625
See application file for complete search history.

(56) References Cited

U.S. PATENT DOCUMENTS

| | | | |
|---|---|---|---|
| 8,521,274 B2 | 8/2013 | Gutsol et al. | |
| 8,906,659 B2 | 12/2014 | Clyne et al. | |
| 8,994,271 B2 | 3/2015 | Kindel et al. | |
| 9,044,219 B2* | 6/2015 | Rooks | A61B 18/042 |
| 9,257,264 B2* | 2/2016 | Hummel | H01J 37/32348 |
| 9,384,947 B2* | 7/2016 | Watson | A61N 1/44 |
| 9,656,095 B2* | 5/2017 | Watson | A61M 15/02 |
| 2009/0012589 A1* | 1/2009 | Watson | A61L 2/0011 |
| | | | 607/99 |
| 2013/0069530 A1* | 3/2013 | Watson | H01J 37/3266 |
| | | | 315/111.21 |
| 2013/0071286 A1* | 3/2013 | Watson | A61L 2/00 |
| | | | 315/111.21 |
| 2013/0072858 A1* | 3/2013 | Watson | H01J 37/3244 |
| | | | 604/23 |
| 2013/0345620 A1 | 12/2013 | Zemel et al. | |
| 2014/0188097 A1 | 7/2014 | Watson et al. | |
| 2014/0225495 A1* | 8/2014 | Koo | H01J 37/32431 |
| | | | 313/35 |
| 2016/0106993 A1* | 4/2016 | Watson | H01J 37/32825 |
| | | | 604/23 |
| 2016/0136062 A1 | 5/2016 | Woodland et al. | |
| 2016/0193373 A1* | 7/2016 | Fridman | A61L 2/14 |
| | | | 250/493.1 |
| 2016/0271419 A1 | 9/2016 | Varghese et al. | |
| 2018/0008333 A1 | 1/2018 | Jin | |

FOREIGN PATENT DOCUMENTS

| | | |
|---|---|---|
| EP | 3068328 | 9/2016 |
| JP | 2014505553 | 3/2014 |
| JP | 2014167913 | 9/2014 |
| JP | 2014212839 | 11/2014 |
| JP | 2015516219 | 6/2015 |
| JP | 2017-522926 A | 8/2017 |
| JP | 2018921 A | 1/2018 |
| JP | 2018519858 A | 4/2018 |
| JP | 2018516657 A | 6/2018 |
| JP | 2018-114287 A | 7/2018 |
| WO | 2010107722 A1 | 9/2010 |
| WO | 2018207020 A1 | 11/2018 |

OTHER PUBLICATIONS

Annex to Form PCT/ISA/206: Communication Relating to the Search Results of the Partial International Search and Provisional Opinion Accompanying the Partial Search Report, dated Oct. 22, 2019, issued in corresponding International Patent Application No. PCT/US2019/044083, filed Jul. 30, 2019, 12 pages.

Annex to Form PCT/ISA/206: Communication Relating to the Search Results of the Partial International Search and Provisional Opinion Accompanying the Partial Search Report, dated Oct. 25, 2019, issued in corresponding International Patent Application No. PCT/US2019/044224, filed Jul. 30, 2019, 13 pages.

Japanese Patent Office, Notice of Reasons for Refusal, Japanese Patent Application No. 2021-505513, dated Feb. 28, 2022, 10 pages.

Japanese Patent Office, Notice of Reasons for Refusal, Japanese Patent Application No. 2021-505244, dated Feb. 28, 2022, 8 pages.

International Search Report and Written Opinion, dated Jan. 8, 2020, issued in corresponding International Application No. PCT/US2019/044083, filed Jul. 30, 2019, 17 pages.

Notice of Reasons for Refusal dated Aug. 2, 2022, issued in corresponding JP Application No. 2021-505213, filed Jul. 30, 2019, 4 pages.

* cited by examiner

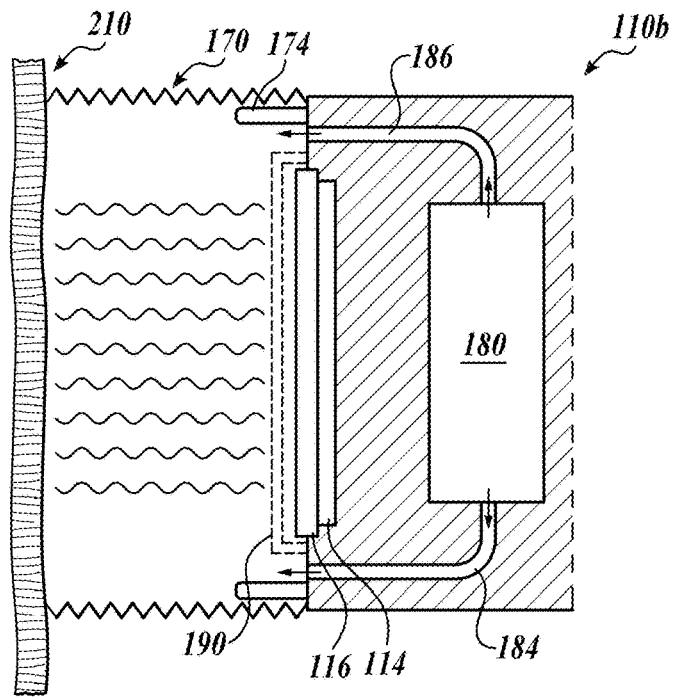
FIG. 11B
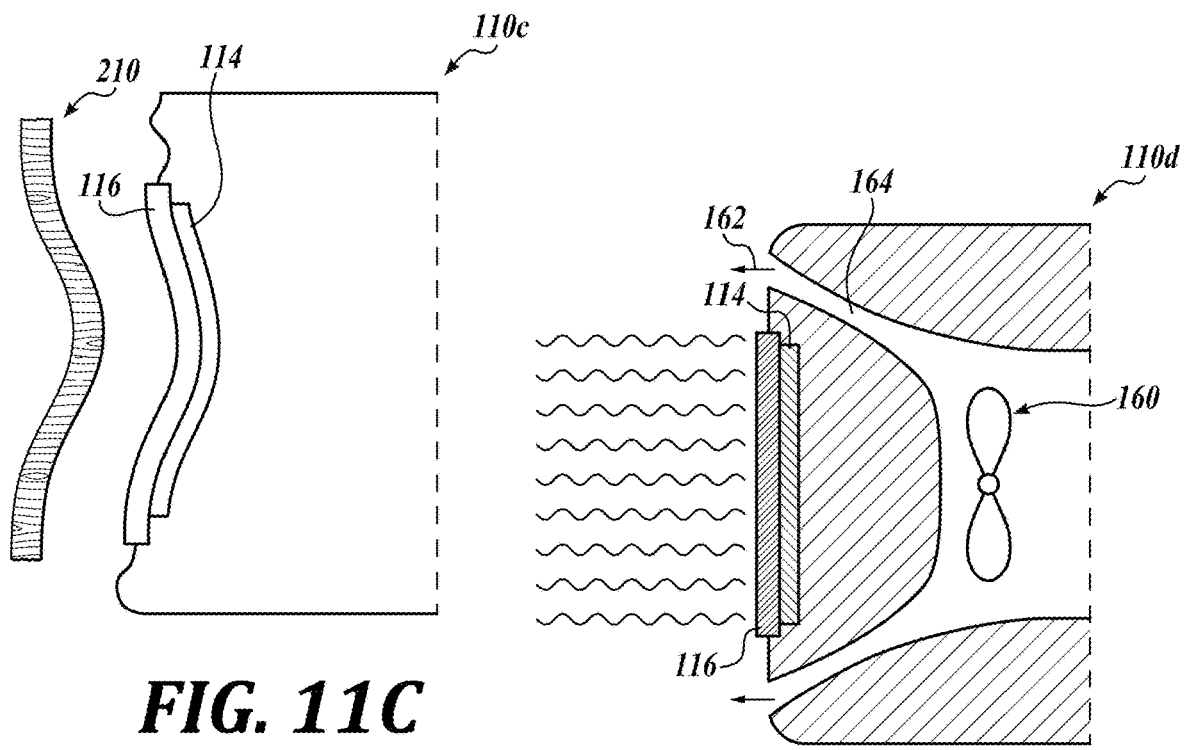
FIG. 11C
FIG. 11D

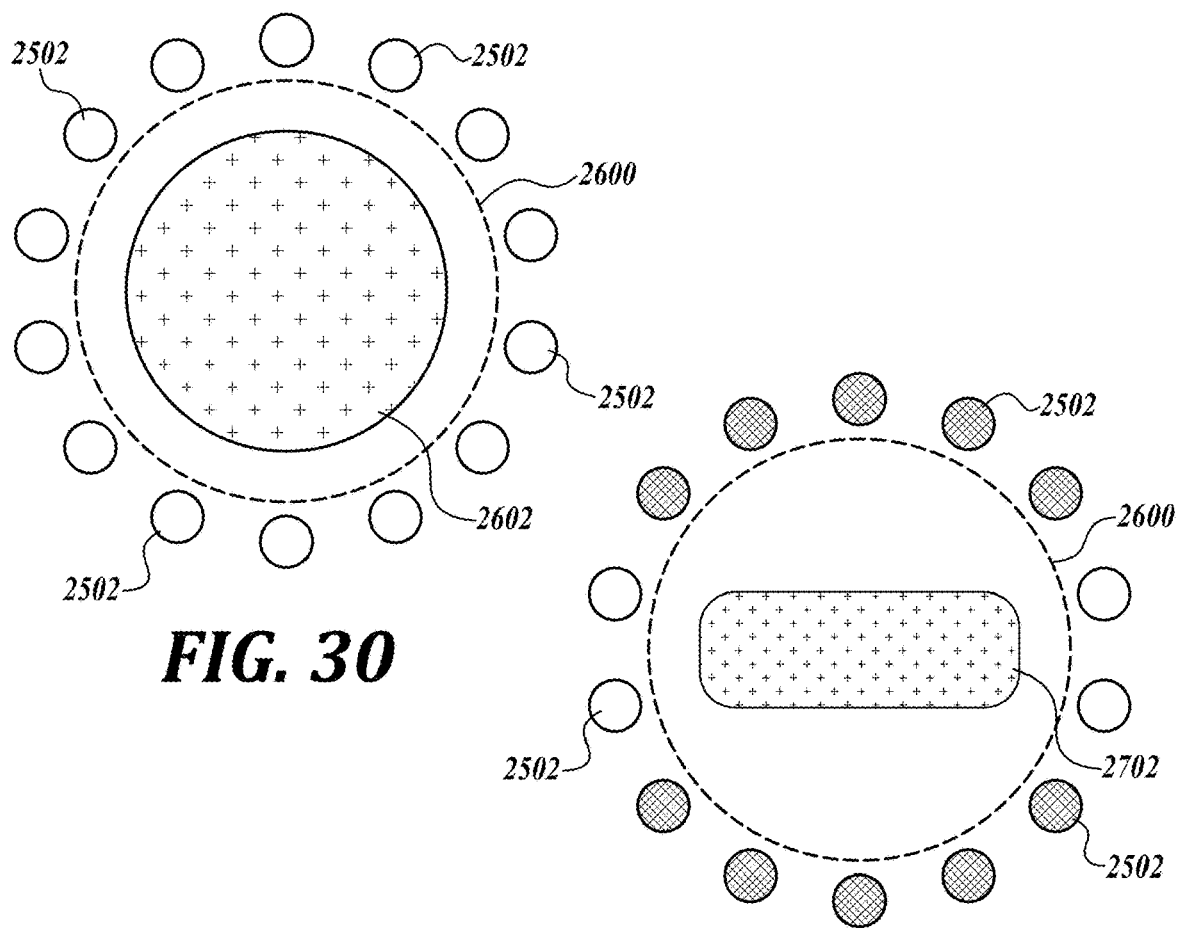
FIG. 30
FIG. 31
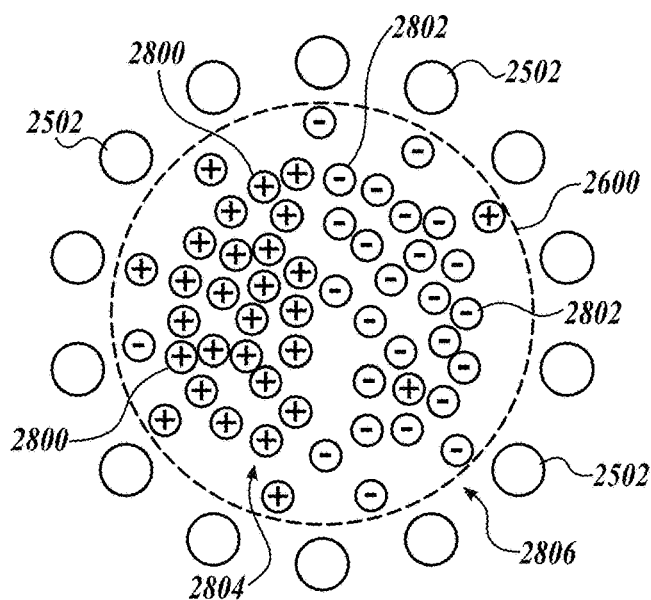
FIG. 32

GENERATING COLD PLASMA AWAY FROM SKIN, AND ASSOCIATED SYSTEMS AND METHODS

CROSS-REFERENCES TO RELATED APPLICATIONS

This application claims the benefit of U.S. Provisional Application No. 62/712,812, filed Jul. 31, 2018; U.S. Provisional Application No. 62/712,849, filed Jul. 31, 2018; U.S. Provisional Application No. 62/712,860, filed Jul. 31, 2018; U.S. Provisional Application No. 62/712,873, filed Jul. 31, 2018; U.S. Provisional Application No. 62/712,876, filed Jul. 31, 2018; U.S. Provisional Application No. 62/773,944, filed Nov. 30, 2018; U.S. Provisional Application No. 62/773,958, filed Nov. 30, 2018; U.S. Provisional Application No. 62/773,969, filed Nov. 30, 2018; U.S. Provisional Application No. 62/773,984, filed Nov. 30, 2018; each of which applications are expressly incorporated herein by reference in their entirety.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The application of a cold atmospheric plasma (also referred to as "cold plasma" or "plasma") to biological surfaces introduces challenges for skin treatment, arising from the complex biological system interactions. In practice, surface conditions and plasma parameters are coupled, where variation in one induces changes in the other. A sudden shift in surface moisture, for example, may affect electrical conductivity of the surface and lead to an increase in plasma intensity. Conversely, a sudden increase in plasma intensity may vaporize moisture from the surface, in turn changing the properties of plasma. This variability and multi-parameter coupling necessitates control of the plasma treatment device.

Complex interactions between light emission from the plasma, plasma generated species, and biological chemicals native to biological surfaces further complicates cold plasma therapy. In some cases, plasma generated species may acidify a biological surface, thereby aggravating preexisting conditions and outweighing any beneficial outcomes of plasma treatment, for example by light emission, or by exposure to plasma generated species that stimulate wound healing or that would otherwise denature harmful bacteria present in the biological surface.

In some applications, generating the cold plasma away from the biological surface (e.g., skin) may be advantageous in comparison to generating the cold plasma proximately to the biological surface. When the cold plasma is generated away from the biological surface, the concentration, temperature, pressure, and other properties of the plasma can be controlled less tightly than when the plasma is generated directly at the biological surface. For example, whereas the temperature of the air that carries the cold plasma toward the biological surface has to be within a relatively narrow range (to avoid discomfort to the user), the range of temperatures for the incoming air is wider when the plasma is generated away from the biological surface. Subsequent to generating the cold plasma, the temperature of the air may be lowered or raised to a more acceptable range while the plasma is still within the cold plasma generating device. In some embodiments, the concentration of the plasma species may also be higher for the plasma generated away from the biological surface, because the concentration of the plasma species can be reduced inside the device before the cold plasma reaches the biological surface. For example, the concentration of the plasma species and the temperature of the air will generally decrease with time elapsed from the creation of the plasma species.

Cold Plasma Therapy Devices

Non-thermal "cold" atmospheric plasma can interact with living tissue and cells during therapeutic treatment in multiple ways. Among the possible applications, cold atmospheric plasma may be used in biology and medicine for sterilization, disinfection, decontamination, and plasma-mediated wound healing.

Several commercialized devices are certified for medical treatment at the present time. These devices are not designed for home use by consumers. Instead, they are designed for use by medical technicians with expertise and training in medical treatment techniques. An example of such device is Rhytec Portrait®, which is a plasma jet tool for topical dermatological treatments. This device features complex power supplies with tightly regulated parameters, using radio-frequency power sources. In addition, the Bovie J-Plasma®, the Canady Helios Cold Plasma, and the Hybrid Plasma™ Scalpel are all available for use as medical treatment devices. In Germany, the kINPen®, also a plasma jet device, and the PlasmaDerm®, a dielectric barrier discharge (DBD) device, are both certified medical devices that have been introduced to the market within recent years. These devices aim at medical treatment of human tissues, either externally, as in the PlasmaDerm®, or internally. In contrast with the plasma devices for the medical use, the devices for the cosmetic use are geared for a generally intuitive use by consumers, resulting in cosmetic care and pleasant sensation, as opposed to well controlled and certifiable therapeutic effect.

FIG. 1 is a schematic diagram of a plasma generator 10 in accordance with prior art. As shown in FIG. 1, a cold plasma 18 forms through disparate excitation of electrons in a plasma gas by electric fields, relative to the milder excitation effect of the fields on the more massive nuclei of the plasma gas. The cold plasma 18 is formed between a live electrode 14 and a ground electrode 15, also called a counter-electrode, when the live electrode 14 is energized relative to the ground electrode 15 by a power source 12. The power source 12 is an alternating current source or an amplitude modulated direct current source. The cold plasma 18 is a dielectric barrier discharge if the plasma generator 10 includes a dielectric barrier 16 that is placed against the live electrode 14. The cold plasma 18 contains both high temperature electrons 19 and low temperature ions 19 and neutral species. In conventional systems, the plasma gas includes noble gases like helium or argon, and also oxygen and nitrogen containing gases to form reactive oxygen and nitrogen species (RONS). In some cases, as with the PlasmaDerm®, the plasma forms directly in air.

FIG. 2 is an image of dielectric barrier discharges 20 in operation in accordance with prior art. FIG. 2 was obtained as a plan view through a transparent electrode. The plasma 18 forms as multiple discrete filamentary discharges that individually form conductive bridges for ions and electrons 19 to migrate between the electrodes.

For topical treatment, several forms of plasma are used. The first is the gas jet plasma which provides a jet of ions and reactive species that can be directed to a target over varying distances, typically at distances greater than a few millimeters. The medical plasmas described in a preceding paragraph typically feature a gas jet plasma. A second form is the Floating Electrode Dielectric Barrier Discharge (FE-DBD) devices, in which the target substrate (often the human body) acts as a floating ground electrode. The third form is a DBD plasma wand, where the dielectric barrier is placed against a floating ground, instead of the live electrode, and may take the form of a fluorescent tube. The fourth form is a coordinated plurality of dielectric barrier discharge sources. In such an arrangement, a number of atmospheric FE-DBD plasma sources are incorporated into a handheld or flexible device, that is then used to treat one or more anatomical regions.

FIGS. 3A and 3B are two views of a cold plasma system in accordance with prior art. A skin treatment device 30 produces cold plasma 18 through a unitary structure that includes a head 31 and a body 34. The device includes one or more user controls, including a plasma power switch 32, and a light switch 33. The head 31 includes one or more light emitting diodes 35 (LEDs). The skin treatment device 30 further includes a plasma pulse control 37, configured to create the plasma 18 at the head 31 while the plasma pulse control 37 is pressed. The skin treatment device 30 includes a charging port 36 for charging an enclosed battery. The skin treatment device 30 includes internal electronic components that drive the plasma 18.

FIG. 4 is a block diagram of a cold plasma system in accordance with prior art. Electronic components 40 include a unitary structure having a DBD head 47 and body 42. The cold plasma 18 is produced between electrodes included in the DBD head 47, which serves as the treatment site. The DBD head 47 is electrically connected to a high voltage unit 45, providing power to the DBD head 47. The power needed to drive the plasma 18 is provided by a rechargeable battery pack 43 enclosed within the body 42. The system includes one or more LEDs 46, connected to the system through a main PC board and control circuitry 44. The main PC board and control circuitry 44 controls the flow of electricity to the LED 46 and the high voltage unit 45, and receives input from one or more user controls 48 and external power in 49 to charge the rechargeable battery pack 43.

Without being bound to theory, it is believed that the effect of cold atmospheric plasma therapy is due to some extent to interaction between RONS and biological systems. A non-exhaustive list of RONS includes: hydroxyl (OH), atomic oxygen (O), singlet delta oxygen ($O_2(^1\Delta)$), superoxide ($O_2^-$), hydrogen peroxide ($H_2O_2$), and nitric oxide (NO). Hydroxyl radical attack is believed to result in peroxidation of cell membrane lipids, in turn affecting cell-cell interaction, regulation of membrane-protein expression, and many other cellular processes. Hydrogen peroxide is a strong oxidizer, believed to have a harmful effect on biological systems. Nitric oxide is believed to play a role in cell-cell signaling and bio-regulation. At the cellular level, nitric oxide is believed to affect regulation of immune deficiencies, cell proliferation, phagocytosis, collagen synthesis, and angiogenesis. At the system level, nitric oxide is a potent vasodilator.

Cold atmospheric plasmas also expose biological surfaces to electric fields, on the order of 1-10 kV/cm. It is believed that cells respond to such fields by opening trans-membrane pores. Such electric-field induced cellular electroporation is believed to play a role in transfusion of molecules across cell membranes. Without being bound to theory, the efficacy of treatment is believed to be due at least in part to long-lived plasma-generated species, which in an air plasma will be a variety of RONS at concentrations particular to the operating parameters of the cold atmospheric plasma source.

While cold atmospheric plasma can also be used to ablate tissue or effect treatment in a very short time when operated at high power and intensity, such treatment is believed to harm surrounding tissue and to penetrate far beyond the treated area. Without being bound to theory, it is believed that cold atmospheric plasma treatment at low intensity avoids damaging cells.

Without being bound to theory, it is believed that an important parameter both for direct cold atmospheric plasma treatment and for indirect treatment using plasma-treated media is the dose of plasma species imparted to the treatment surface. In general, this is expressed as a concentration of a given plasma species produced by the cold atmospheric plasma source that is imparted to a unit area of the treated surface over a unit time.

Alternatively, the dose may be expressed as a simple length of time, if the treatment has been determined and the behavior of the cold atmospheric plasma source is well understood. For example, for a stable cold atmospheric plasma source and a uniform surface, a particular dose of a given RONS will be achieved after the cold atmospheric plasma has treated the uniform surface for a given length of time. In practice, surface conditions and plasma characteristics are coupled, where variation in one induces changes in the other. A sudden shift in surface moisture, for example, may affect the conductivity of the surface and lead to an increase in plasma intensity. Conversely, a sudden increase in plasma intensity may vaporize moisture from the surface, producing RONS and changes in the surface. This variability necessitates control of the plasma treatment device, as discussed in greater detail below.

Without being bound to theory, it is believed that cold atmospheric plasma treatment penetrates into the treatment surface through a synergistic effect of electroporation, permeability of plasma generated species, and cell-to-cell signaling. The so called "bystander effect" is thought to play a role in propagating plasma induced cellular changes away from the treatment surface and into a volume beneath it. The bystander effect is believed to occur through chemical signals passed between cells in response to the introduction of a biologically active chemical, potentially amplifying the magnitude of the treatment impact.

In experiments it has been shown that RONS include reactive nitrogen species (RNS) and reactive oxygen species (ROS) that are believed to interact in differing ways to diverse biological surfaces. In agarose films, for example, RONS permeate a volume beneath the film, while in living tissues, only RNS will do so. ROS do penetrate, however, into gelatin and other liquids. ROS, being more reactive than RNS are shorter-lived and are believed to be linked in some circumstances to aggressive or harmful effects on biological surfaces, as previously discussed with respect to hydrogen peroxide.

Generating Cold Plasma Away from Skin of User

In one embodiment, a cold plasma system for treating a region of a biological surface includes: a housing; an air conduit within the housing; a first electrode configured proximately along the air conduit; a second electrode configured proximately along the air conduit and opposite from the first electrode; and a source of alternating current (AC)

electrically connected with the first electrode. The source of alternating current may be configured to generate a cold plasma in the air conduit. The system also includes an air mover configured to transport the cold plasma outside of the cold plasma system.

In one aspect, the system also includes a reservoir configured within the housing. The reservoir is in a fluid communication with the air conduit, and the reservoir is configured for holding the cold plasma. The system also includes a cartridge containing a plasma precursor. The cartridge is in a fluid communication with the air conduit.

In one aspect, the air conduit is a first air conduit, and the system also includes: a first air mover configured to transport the cold plasma from the first air conduit toward the reservoir; a second air conduit in a fluid communication with the reservoir and the first air conduit; a second air mover configured to transport the cold plasma from the reservoir toward the cartridge; and a controller configured to control a speed of rotation of the first air mover and a speed of rotation of the second air mover based on a difference between a present concentration and a target concentration of the cold plasma in the reservoir. The target concentration is selected at least in part based on a half-life of the cold plasma.

In one aspect, the system also includes a third air mover configured to direct the cold plasma out of the cold plasma system, and toward the biological surface.

In one aspect, the cartridge is insertable.

In one aspect, the plasma precursor includes precursor components that generate reactive oxygen species or reactive nitrogen species (RONS) in the cold plasma that include at least one of hydroxyl (OH), atomic oxygen (O), singlet delta oxygen (O2(1Δ)), superoxide (O2-), hydrogen peroxide (H2O2), and nitric oxide (NO).

In one aspect, the system also includes means for controlling a flow of cold plasma. Such means may be: a compressible skirt configured to contain the cold plasma proximate to the biological surface; a face mask configured to contain the cold plasma proximate to the biological surface, where a mask intake is in fluid communication with the air conduit; and a plurality of electromagnetic field generator units configured to steer or bend a discharge direction of the cold plasma between a plasma barrier and the biological surface.

In one embodiment, a cold plasma system for treating a region of a biological surface includes a plasma generator having: an electrode; and a dielectric barrier disposed between the electrode and the biological surface to be treated. The plasma generator is configured to generate a first cold plasma. A plurality of electromagnetic field generator units are disposed between the plasma generator and the biological surface to be treated. The plurality of electromagnetic field generator units are configured to generate a second cold plasma based on the first cold plasma, and wherein the second cold plasma is provided to the biological surface.

In one aspect, the plurality of electromagnetic field generator units are configured to steer or bend a first direction of the first cold plasma to a second direction of the second cold plasma toward the biological surface.

In one aspect, the first cold plasma includes positively charged species and negatively charged species, and the second cold plasma includes the positively charged species segregated from the negatively charged species.

In one aspect, the second cold plasma has a different cross-sectional shape than the first cold plasma, and the second cold plasma has a higher plasma species concentration per cross-sectional unit area than the first cold plasma.

In one embodiment, a method of treatment of a region of a biological surface with cold plasma includes: generating a first cold plasma; modifying the first cold plasma using electromagnetic fields to generate a second cold plasma; and providing the second cold plasma to the region of the biological surface.

In one aspect, modifying the first cold plasma using the electromagnetic fields includes: generating first and second electromagnetic fields; simultaneously applying the first and second electromagnetic fields at first and second locations, respectively, proximate to the first cold plasma; and generating the second cold plasma based on the first and second electromagnetic fields applied to the first cold plasma, wherein the first and second electromagnetic fields differ from each other in one or more parameters.

In one aspect, modifying the first cold plasma includes modifying the first cold plasma to the second cold plasma having a higher plasma species concentration per cross-sectional unit area than that of the first cold plasma.

In one aspect, modifying the first cold plasma using the electromagnetic fields comprises steering or bending a first direction of the first cold plasma to a second direction of the second cold plasma toward the biological surface by the plurality of electromagnetic field generator units.

In one aspect, the method also includes: applying at least one of the first cold plasma and the second cold plasma to an initial formulation; changing the initial formulation to an activated formulation based on application of the at least one of the first cold plasma and the second cold plasma, where the activated formulation includes at least one compound absent in the initial formulation that is a plasma specie of the cold plasma, and where the at least one compound is configured to stabilize or increase the lifetime of short lived plasma species absorbed into the initial formulation; and applying formulation to the biological surface.

DESCRIPTION OF THE DRAWINGS

The foregoing aspects and advantages of the inventive technology will become more readily appreciated as the same become better understood by reference to the following detailed description, when taken in conjunction with the accompanying drawings, wherein:

FIG. 11B is a schematic diagram of a cold plasma treatment system in accordance with the present disclosure;

FIG. 11C is a schematic diagram of a cold plasma treatment system in accordance with the present disclosure;

FIG. 11D is a schematic diagram of a cold plasma treatment system in accordance with the present disclosure;

FIG. 18 depicts a flow diagram of an example process that may comprise an alternative to the process of FIG. 15 in accordance with the present disclosure;

FIGS. 30-32 depict simplified cross-sectional views of at least a portion of the device of FIG. 15 and various resulting plasma in accordance with the present disclosure;

DETAILED DESCRIPTION

While several embodiments have been illustrated and described, it will be appreciated that various changes can be made therein without departing from the spirit and scope of the inventive technology.

Cold Plasma System with Additional Treatment Devices

Figure 1:
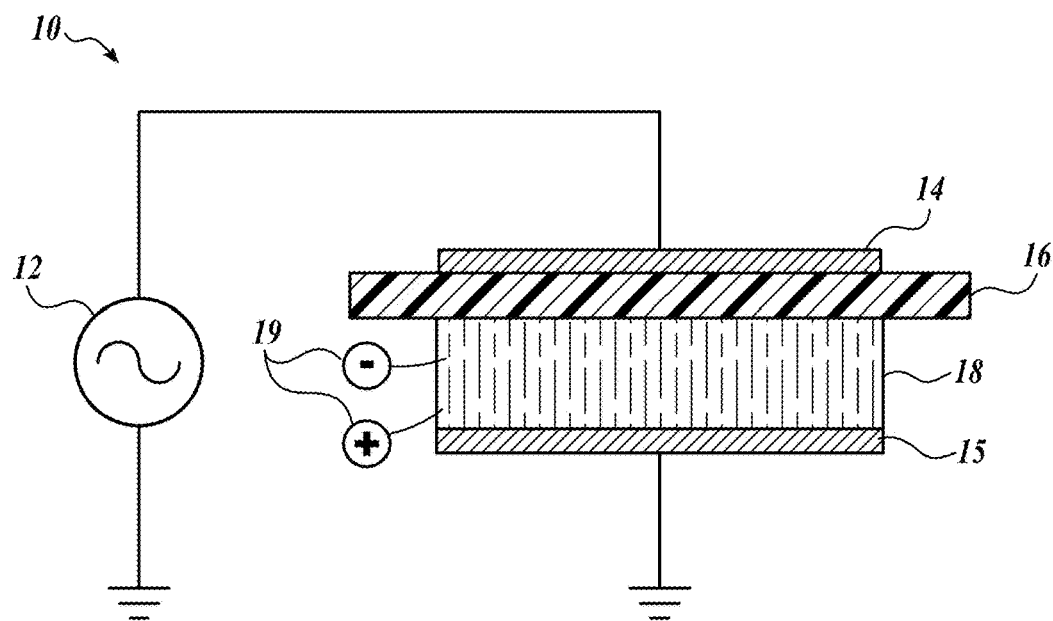
FIG. 1 is a schematic diagram of a plasma generator in accordance with prior art.
Figure 2:
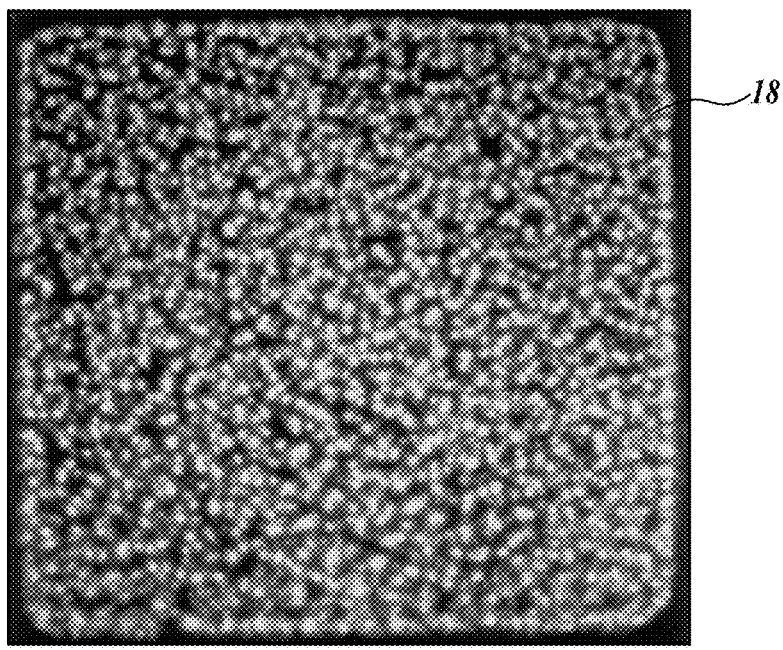
FIG. 2 is an image of a dielectric barrier discharge surface in operation in accordance with prior art.
Figures 3A, 3B:
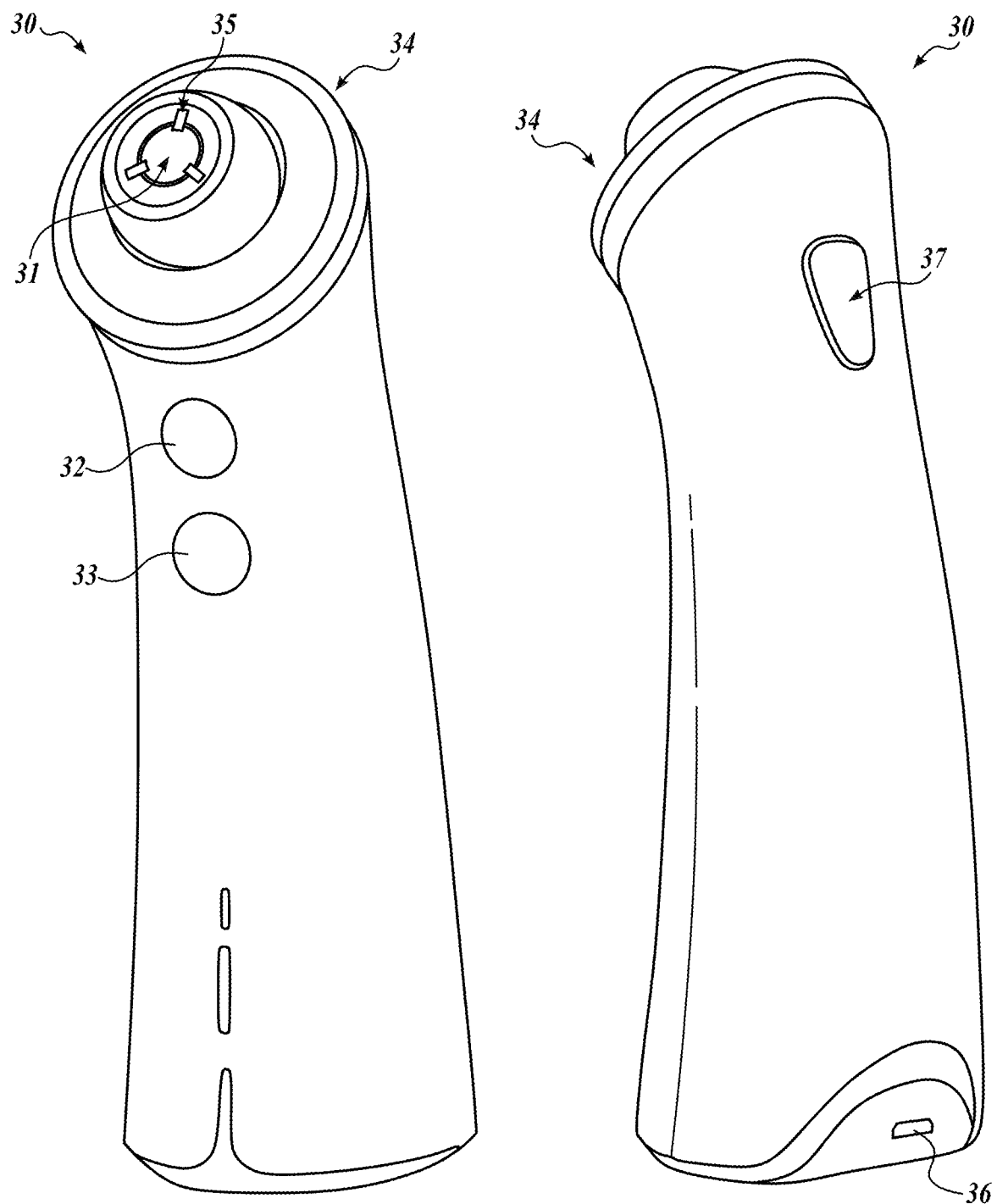
FIGS. 3A-3B are two views of a cold plasma system in accordance with prior art.
Figure 4:
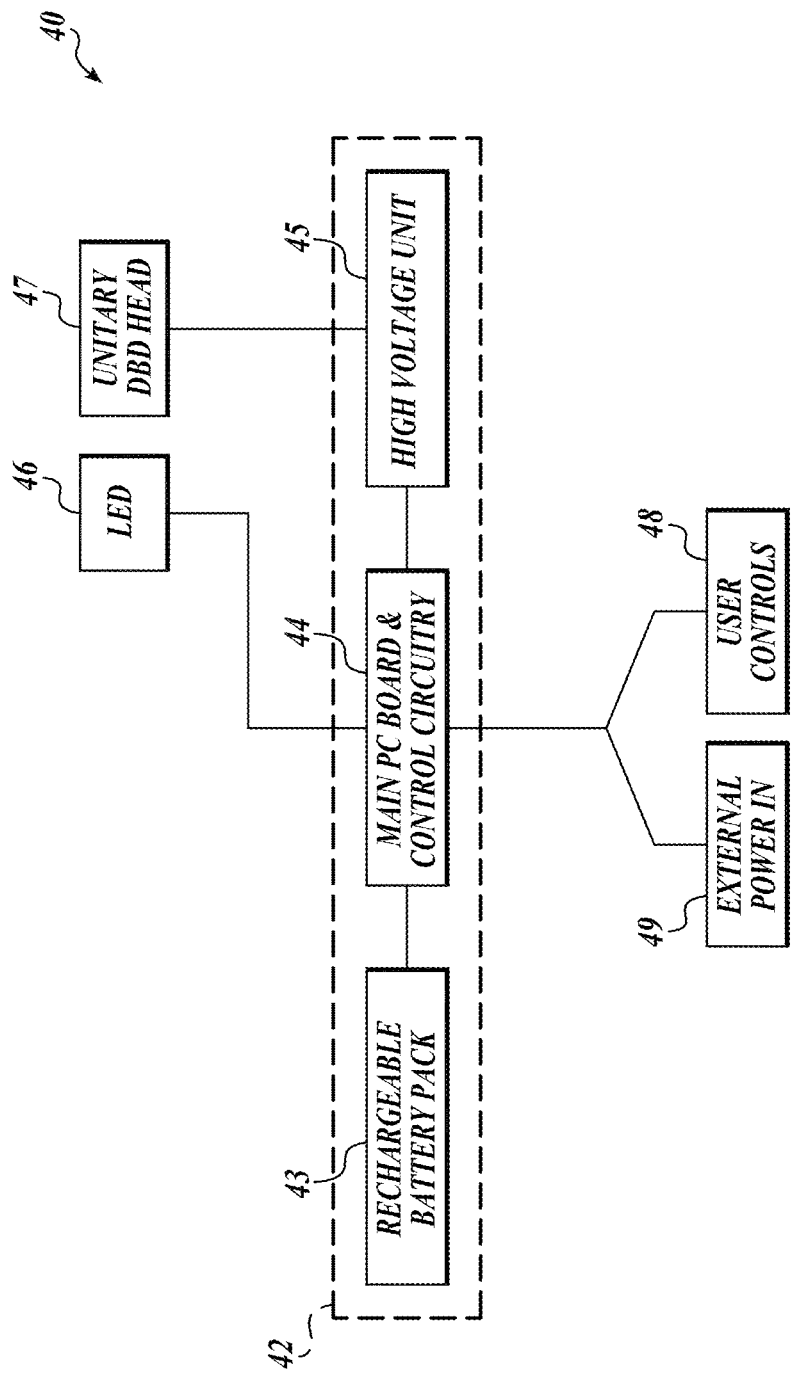
FIG. 4 is a block diagram of a cold plasma system in accordance with prior art.
Figure 5:
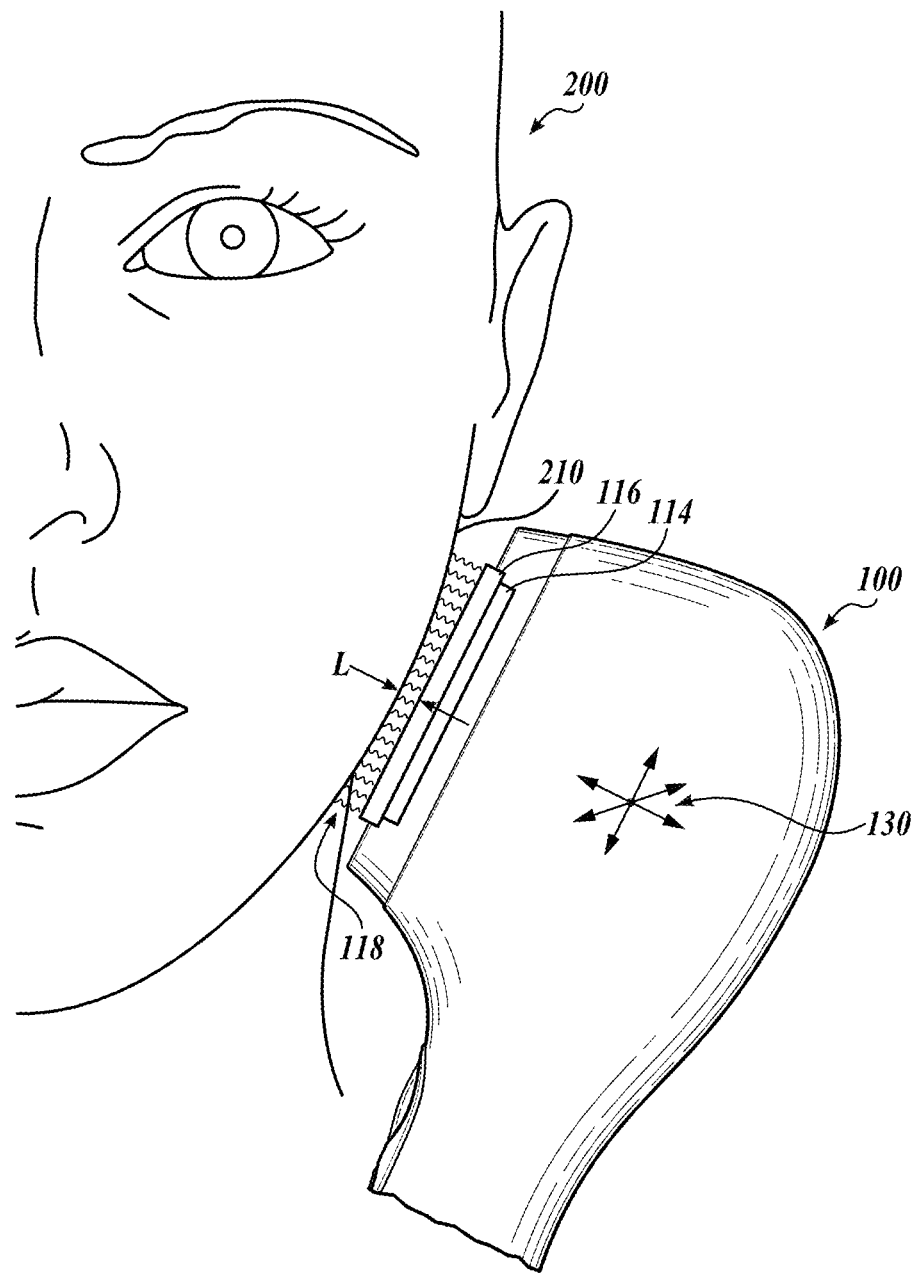
FIG. 5 is a schematic diagram of a cold plasma treatment system in accordance with the present disclosure.

FIG. 5 presents a schematic diagram of a cold plasma treatment system in accordance with the present disclosure. In some embodiments, the cold plasma treatment system provides cosmetic treatment of a region of a biological surface 210 of a consumer 200. In some embodiments, the system includes a cold atmospheric plasma treatment device 100 including a plasma generator having an electrode 114 and a dielectric barrier 116.

In some embodiments, the plasma treatment device 100 includes a vibration device 130. Without being bound to theory, it is believed that the actuation of the vibration device 130 provides the consumer 200 with an enhanced treatment experience, and improves treatment efficacy by mitigating plasma 118 non-uniformity over the region.

The vibration device 130 may vibrate the treatment device 100, thereby affecting the distance L between the second side of the dielectric barrier 116 and the biological surface 210. In some embodiments, the vibration device 130 vibrates the treatment device 100 in multiple axes simultaneously. In other embodiments, the vibration device 130 vibrates the treatment device 100 along only one axis. The vibration device 130 may vibrate the treatment device 100 such that the plasma 118 moves parallel to the biological surface 210 in one or two axes. It is believed that such movement distributes the plasma 118 across the region, thereby improving plasma 118 uniformity. The vibration device 130 may include one or more vibration sources, such as a piezoelectric actuator or a multi-axis eccentric mass vibrator.

Figure 5A:
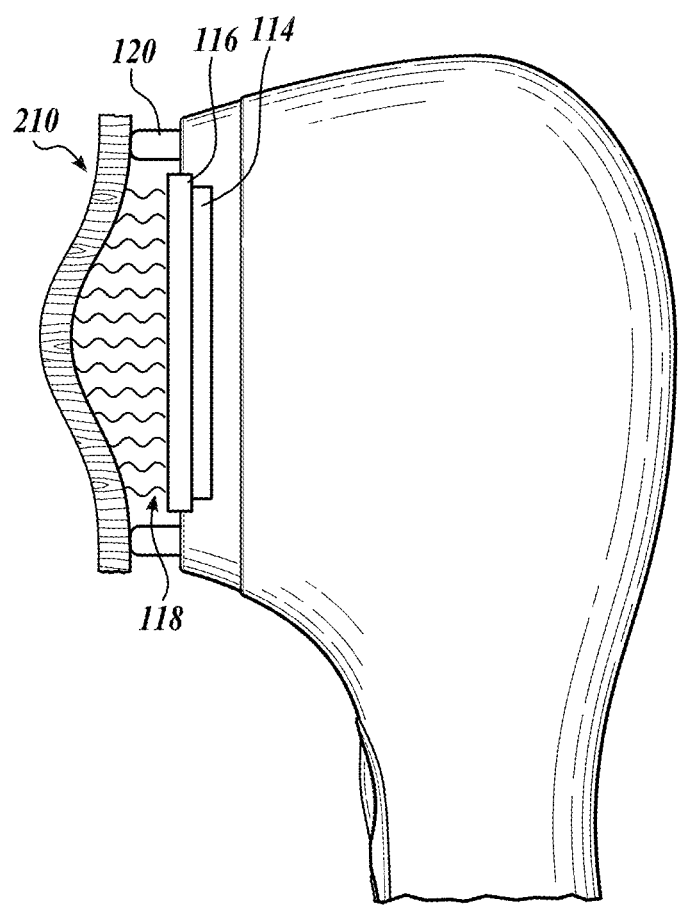
FIG. 5A is a schematic diagram of a cold plasma treatment system in accordance with the present disclosure.

FIG. 5A illustrates a cold plasma treatment system in accordance with the present disclosure. In some embodiments, the plasma treatment device 100 directly actuates the biological surface 210 by one or more actuating members 120. Without being bound to theory, it is believed that repeated tension and compression of the biological surface 210 enhances the efficacy of multimodal treatment by stimulating synergistic effects with permeability of plasma generated species and consumer 200 experience of the treatment. The actuating members 120 may be in direct contact with the biological surface 210 at or near the region. In some embodiments, the actuating members 120 move in opposite directions to each other, parallel to the biological surface 210. The actuating members 120 may move towards each other, in turn compressing and releasing the biological surface 210. The actuating members 120 may move away from each other, in turn stretching and releasing the biological surface 210. In some embodiments, the actuating members 120 move both towards and away from each other, thus both stretching and compressing the biological surface 210. In some embodiments, the plasma 118 is generated toward the region while the actuating members 120 actuate the biological surface 210. The actuating members 120 may actuate the surface without plasma 118 exposure, thereby providing a tactile experience to the consumer 200.

Figure 6:
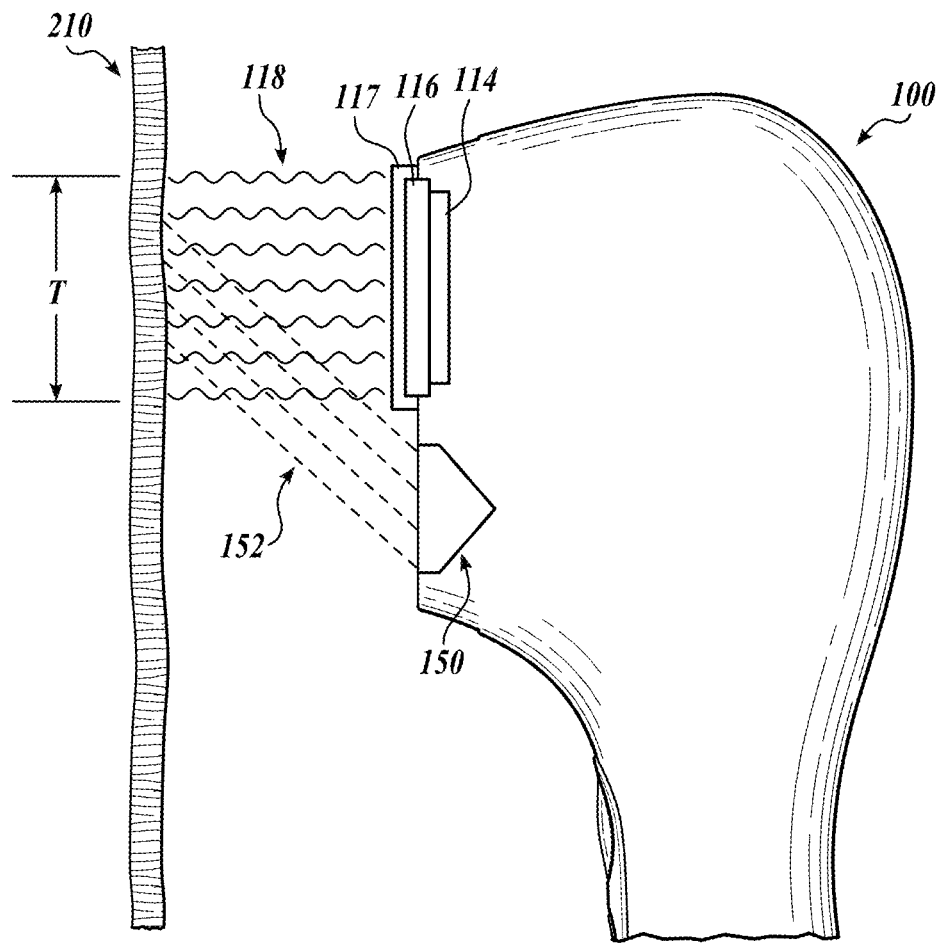
FIG. 6 is a schematic diagram of a cold plasma treatment system in accordance with the present disclosure.

FIG. 6 is a schematic diagram of a cold plasma treatment system in accordance with the present disclosure. In addition to treatment by the plasma 118, the plasma treatment device 100 may include a light source 150, configured to illuminate the region with light 152 within the area described by the characteristic dimension T. As previously described, it is believed that irradiation of the biological surface 210 with light having a wavelength in the range of 400-500 nm provides desirable therapeutic results for cosmetic treatment of blemishes. In some embodiments, the plasma treatment device 100 includes multiple light sources. The light source 150 may include one or more light emitting diodes, individually emitting light having a wavelength within a target range.

The light source 150 may include an infrared light element, providing radiative heating to the biological surface 210. Without being bound to theory, it is believed that radiative heating of the biological surface enhances the therapeutic effect of plasma treatment by triggering a response of the biological surface 210 to plasma generated species and by providing an enhanced experience for the consumer 200.

The plasma treatment device 100 may include a cover 117 disposed on or over the dielectric barrier 116. Non-exclusively, the cover 117 may include plastic, glass, or quartz, and may block plasma generated species from reaching the biological surface 210. Without being bound to theory, it is believed that the plasma 118 may emit ultraviolet photons under certain conditions. As such, it may be desirable to block the transmission of ultraviolet photons using a cover 117.

Figure 7:
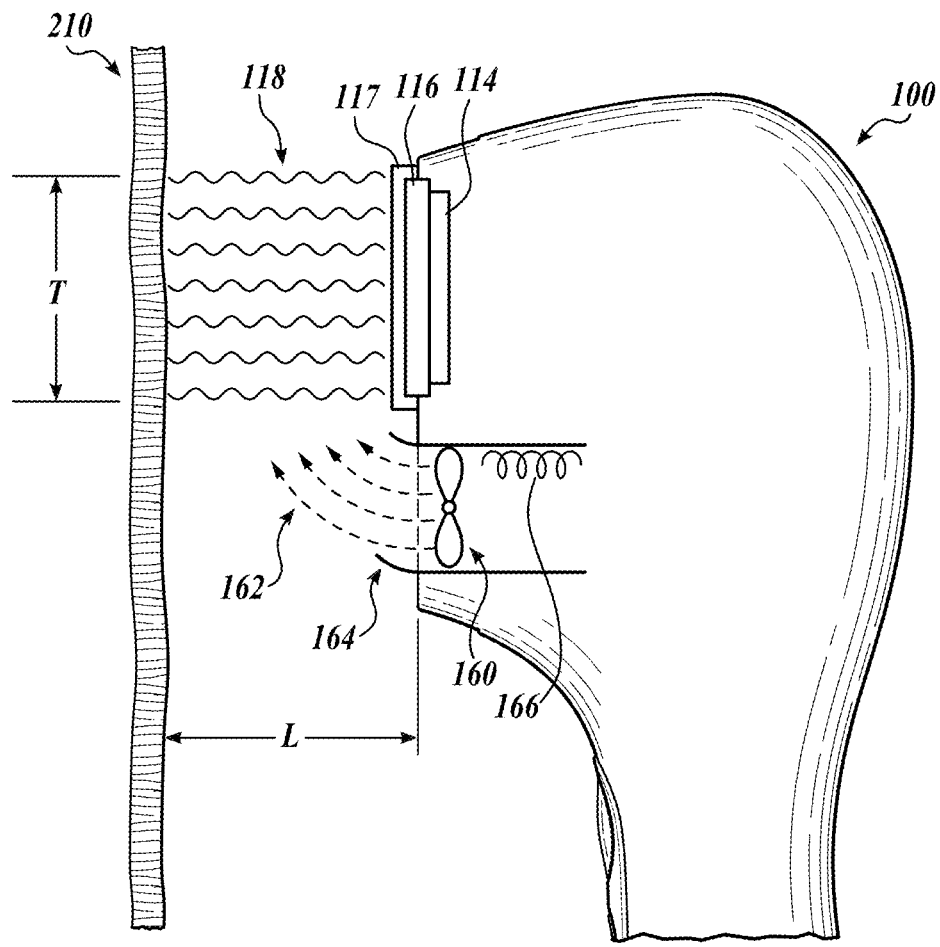
FIG. 7 is a schematic diagram of a cold plasma treatment system in accordance with the present disclosure.

FIG. 7 is a schematic diagram of a cold plasma treatment system in accordance with the present disclosure. In some embodiments, the plasma treatment device 100 includes a source of air that directs an air stream 162 to the region within the area described by the characteristic dimension T. The source of air may include an air mover 160, such as a fan or a blower, disposed within an air conduit 164 that is shaped to provide the air stream 162 at the surface of the region. Gas in the air conduit 164 may be air or other gas (e.g., oxygen, nitrogen or other inert gas, etc.). In some embodiments, one or more temperature control elements 168 disposed within the plasma treatment device 100 adjust the temperature of the air. Non-limiting examples of the temperature control elements 168 include thermoelectric cooling elements including Peltier coolers, electric heating elements including resistive heating coils, etc. In some embodiments, a volatile oil is disposed within the air conduit 164 that contains a fragrance such that, when the air mover 160 is active, the oil imparts a pleasant aroma to the region.

Small Size Device

Figure 8:
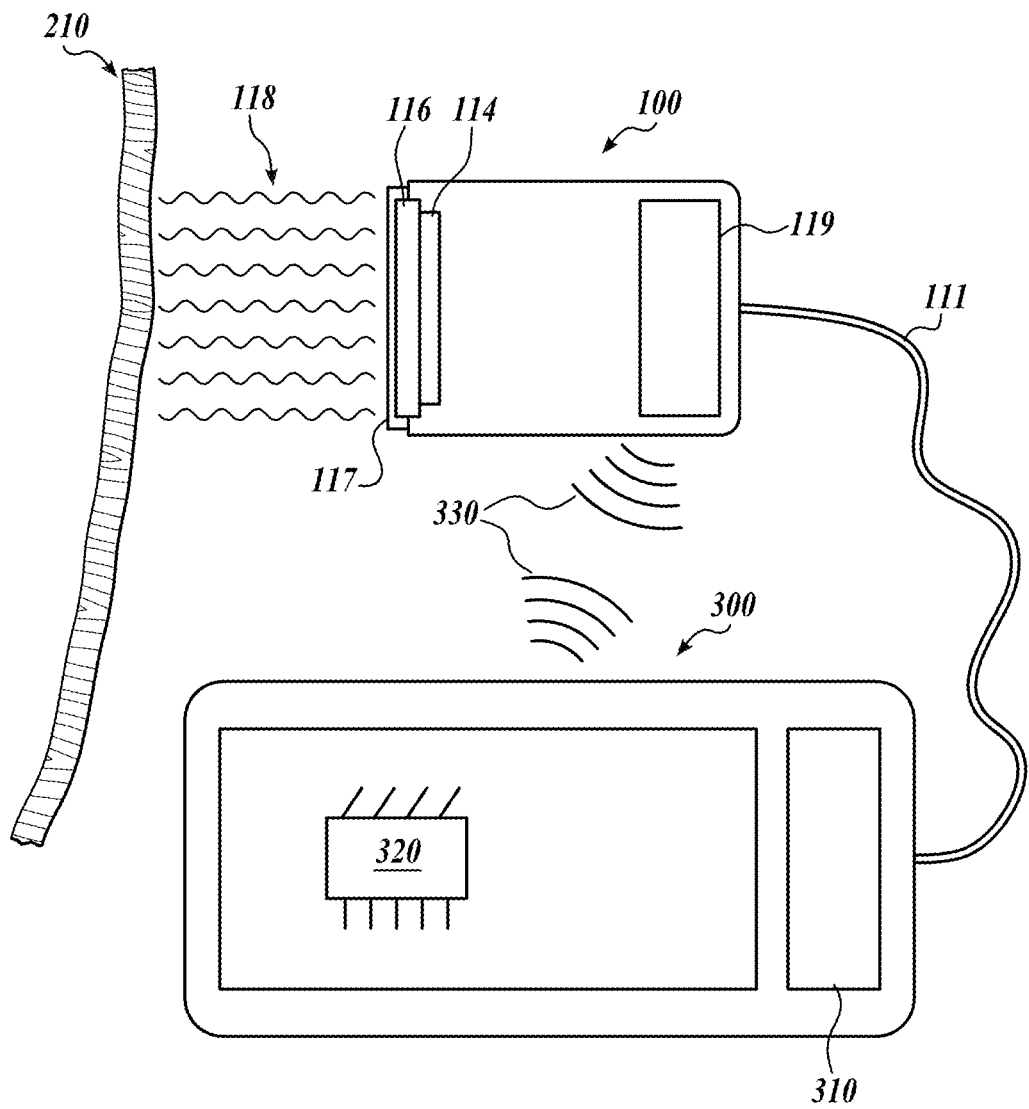
FIG. 8 is a schematic diagram of a cold plasma treatment system in accordance with the present disclosure.

FIG. 8 presents a schematic diagram of a cold plasma treatment system in accordance with the present disclosure. In some embodiments, the plasma treatment device 100 is electrically connected to an external device 300 having a power cell 310 and a controller 320. In some embodiments, the plasma treatment device 100 is electrically connected to the external device via a cable 111. In some embodiments, the cable 111 carries control inputs and electrical power to the plasma treatment device 100. In some embodiments, the cable 111 is detachable from the plasma treatment device 100, the external device 300, or both. The power cell 310 may be a rechargeable battery including, for example a lithium ion battery. The controller 320 may be capable of receiving data and sending control signals to the plasma treatment device 100.

In some embodiments, the plasma treatment device 100 includes a battery 119 electrically connected to the electrode 114. The battery 119 may be rechargeable, charged by connecting the cable 111 to the plasma treatment device 100 and to a power source. Some non-limiting examples of such power source are the external device 300, an adapter connected to a standard wall outlet providing electricity, a solar cell, etc. In some embodiments, the battery 119 charges wirelessly 330. In some embodiments, the battery 119 is a commercially available battery, such as a battery of one of the A-series types ("A," "AA," or "AAA").

In some embodiments, the external device 300 is a smart phone. In some embodiments, the external device 300 is a laptop or a tablet, configured to be compatible with the plasma treatment device 100 and to provide power and control inputs to the external device 300. In some embodiments, the external device 300 is a cosmetic tool, including but not limited to an electronic beard trimmer, a hair iron, a hair drier, an electronic epilator, etc. The external device 300 may be a large area plasma treatment device, as described previously, further including a charging dock for electrically connecting to the plasma treatment device 100. In some embodiments, the charging dock is configured to accept the plasma treatment device 100, which can be operably mounted into the large-area device for compact charging and operation as a plasma generator.

In some embodiments, the electrode 114 and the dielectric barrier 116 are disposed behind a cover 117. The cover 117 may be removable. The cover 117 may provide protection for the dielectric barrier 116 when the plasma treatment device 100 is not in use.

In some embodiments, the electrode 114 and the dielectric barrier 116 are disposed on a retractable support enclosed within the plasma treatment device 100. The retractable support may be configured such that when retracted, the dielectric barrier 116 and the electrode 114 are hidden from view and the plasma treatment device 100 cannot be activated. The retractable support may rotate through the action of a mechanism disposed at an end of the plasma treatment device 100 opposite to the dielectric barrier 116, such that the dielectric barrier 116 emerges from the opposite end of the plasma treatment device 100 in a manner resembling a lipstick. The plasma treatment device 100 may have a form factor similar or comparable to a retractable lipstick tube, such that it resembles the lipstick tube when inactive. In some embodiments, the retractable support is a linear slide that is configured to slide the electrode 114 and the dielectric barrier 116 behind the shield 119 when not in use.

In some embodiments, the plasma treatment device 100 is controlled via a user interface in the external device 300. In some embodiments, the external device 300 is any type of device including a battery, a general purpose computer, and computer readable memory with instructions stored thereon that, when executed by the computer implement a method of treatment of a region of a biological surface by cold atmospheric plasma.

In some embodiments, the plasma treatment device 100 includes one or more user controls including, but not limited to, a power switch, a plasma intensity selector, and a safety switch. The plasma treatment device 100 may be switched on and switched off using a power switch disposed on the plasma treatment device 100, and the plasma 118 is generated while the plasma treatment device 100 is on. In some embodiments, a safety switch prevents the plasma treatment device 100 from turning on until the safety switch is disengaged. In some embodiments, the safety switch is a fingerprint reader. In some embodiments, a plasma intensity selector permits smooth and continuous modulation of the plasma intensity, in terms of a power supplied to the electrode 114. In some embodiments, the plasma intensity selector limits the plasma treatment device 100 to one of a number of discrete intensity settings, in terms of incremental steps in the power supplied to the electrode 114.

In some embodiments, the plasma treatment device 100 includes one or more light emitting diodes (not shown), providing therapeutic light to the biological surface 210. In some embodiments, the light emitting diodes provide blue light, in the range of 400-500 nm.

Cold Plasma with Formulation Dispensing

Figure 9:
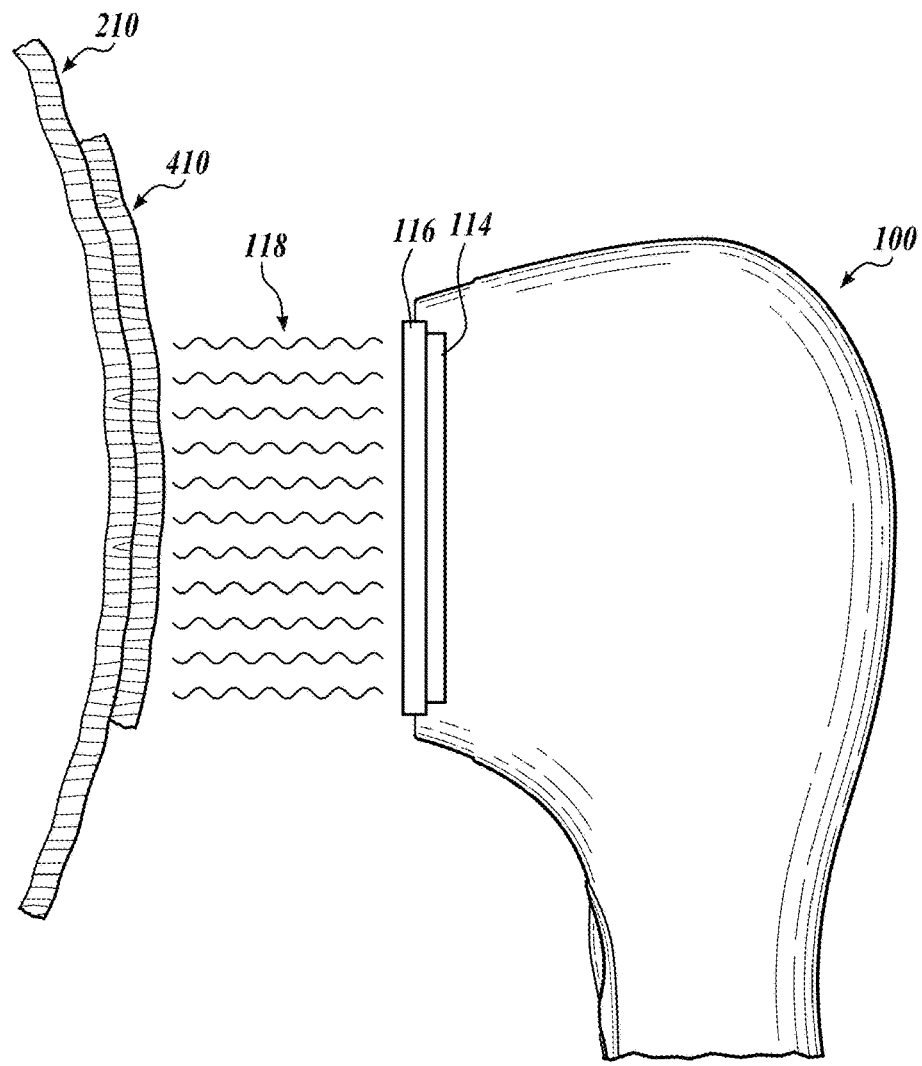
FIG. 9 is a schematic diagram of a cold plasma treatment system in accordance with the present disclosure.

FIG. 9 presents a schematic diagram of a cold plasma treatment system in accordance with the present disclosure. In some embodiments, the plasma treatment device 100, including the dielectric barrier 116 and the electrode 114, discharges the plasma 118 into the biological surface 210 through a formulation 410. The formulation 410 may include one or more active ingredients, including but not limited to anti-oxidants, radical scavenging compounds, ultraviolet absorbing compounds, rejuvenating compounds, etc. In some embodiments, the radical scavenging compound is an anhydrous, glycol-in-silicone formula with ascorbic acid and ascorbyl glucoside. In some embodiments, the radical scavenging compound is a water-in-silicone emulsion with a large internal aqueous phase incorporating water-soluble active ingredients. Without being bound to theory, it is believed that the aqueous phase will form encapsulations, containing active ingredients. Rejuvenating compounds may include collagen, elastin, and the like. The formulation may include inactive ingredients, such as dyes, pigments, fragrances, essential oils, emulsifiers, viscosity modifiers, etc. In some embodiments, the dye may be chemically reactive, and may respond to changes in pH induced by exposure to the plasma 118.

Figure 9A:
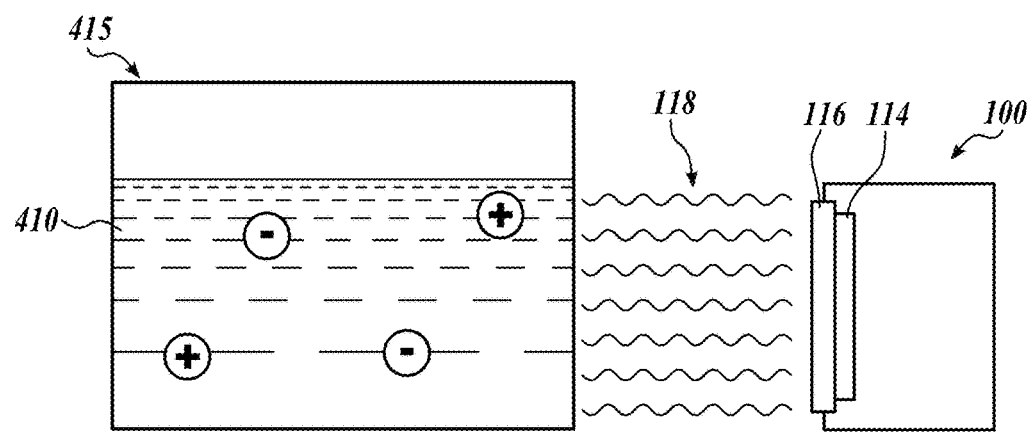
FIG. 9A is a schematic diagram of a cold plasma treatment system in accordance with the present disclosure.

As shown in FIG. 9A, in some embodiments the plasma 118 is discharged into the formulation 410 in a container 415, before application to the biological surface 210 at or near the region. Without being bound to theory, it is believed that the plasma 118 generates beneficial species in the plasma, including ions, radicals, and long-lived RONS. The plasma treatment device 100 may generate the plasma in proximity of the formulation 410, by placing the plasma treatment device 100 near the exposed surface of the formulation 410 while it is in the container 415.

In some embodiments, a pre-treatment formulation enhances the effects of exposure to the plasma 118 by including reagent compounds to generate RONS. In some embodiments, a post-treatment formulation reduces the potentially harmful effects of prolonged exposure to plasma generated species. For example, the post-treatment formulation may control the pH shift of the region after exposure to plasma generated species by including buffer compounds.

Figure 10:
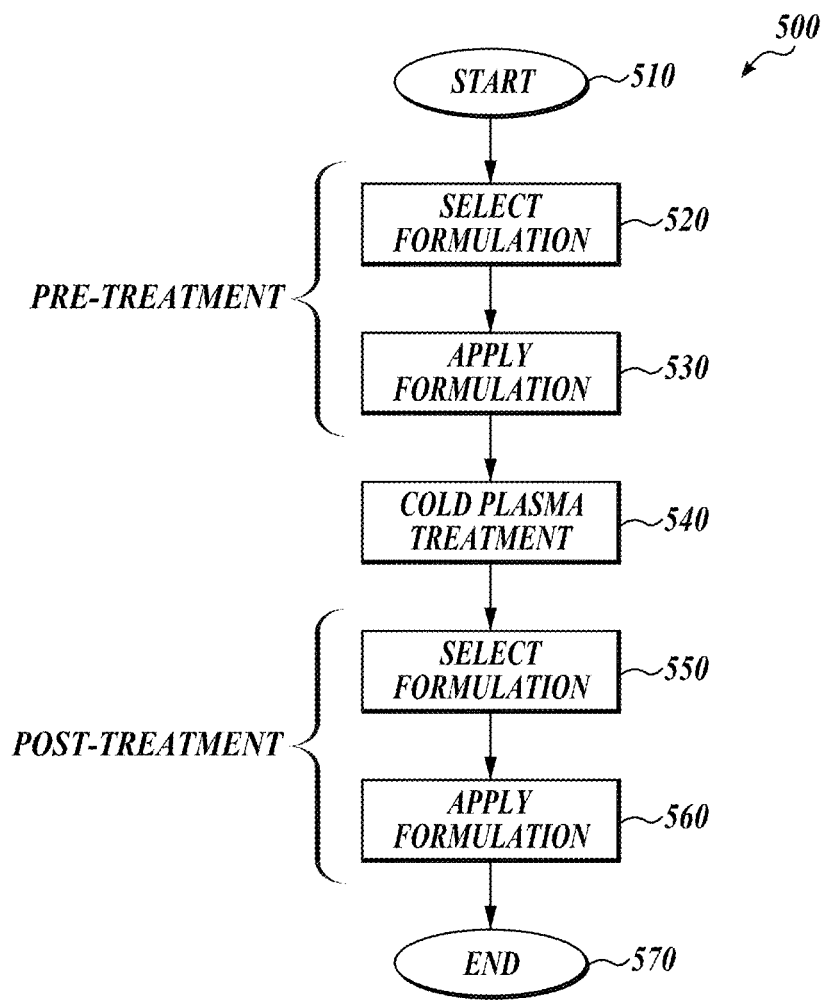
FIG. 10 is a flowchart of a method of cold plasma treatment according to the present disclosure.

FIG. 10 illustrates a method of treatment 500 using the plasma treatment device 100 to generate the plasma 118 between the plasma treatment device 100 and the biological surface 210 that includes at least one formulation 410. In some embodiments, the method may include additional steps or may be practiced without all steps illustrated in the flow chart.

The method starts in block 510, and proceeds to a pre-treatment phase, including selecting a formulation, as shown in block 520, and applying the formulation to the region, as shown in block 530. As previously described, the formulation 410 may have protective or enhancing properties that improve therapeutic results following exposure to the plasma 118. In some embodiments, the formulation 410 is selected for reducing exposure of the region to ultraviolet photons produced in the plasma, or for enhancing production of RONS, etc.

In some embodiments, a pre-treatment formulation is applied to the region before exposure to the plasma 118. The method then proceeds to block 540, which includes generating the plasma 118. The plasma treatment device 100 may generate the plasma 118 in proximity to the region. The plasma treatment in block 540 may continue until the plasma 118 turns off. In some embodiments, the method then proceeds to block 550, where a post-treatment formulation is selected. The post-treatment formulation may be applied to the region following exposure to the plasma 118. The pre-treatment formulation and the post-treatment formulation may be identical or different, and selected to provide different effects to the region. The method ends in block 570. In some embodiments, the method includes removing the pre-treatment formulation following plasma treatment 540. In some embodiments, the method includes removing the post-treatment formulation after applying the post-treatment formulation 560.

Modular Cold Plasma Generating Device

Figure 11:
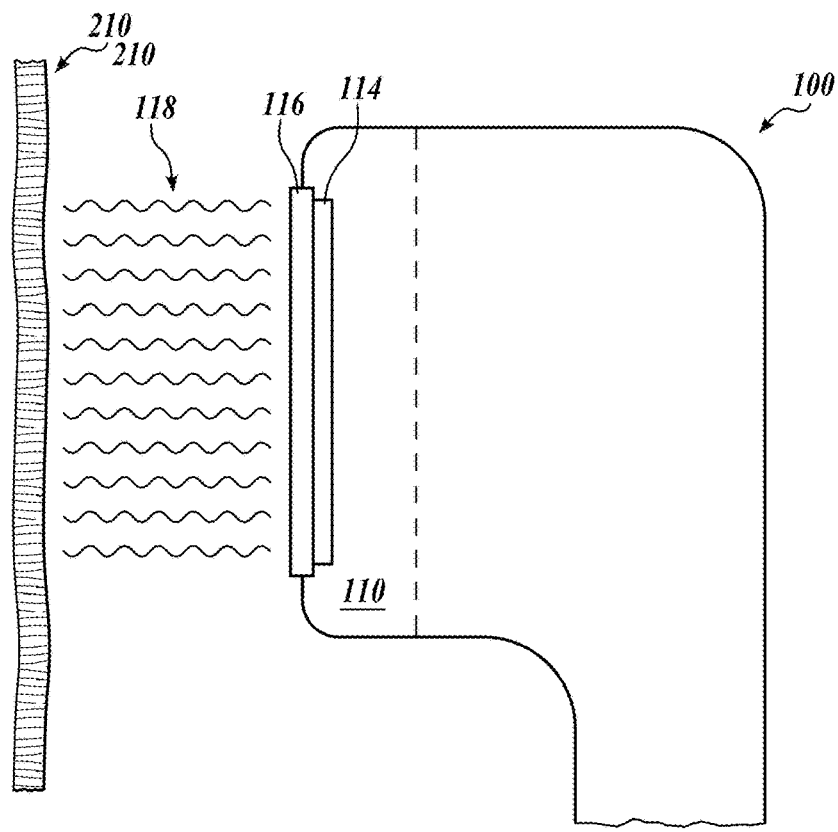
FIG. 11 is a schematic diagram of a cold plasma treatment system in accordance with the present disclosure.

FIG. 11 is a schematic diagram of a cold plasma treatment system 100 in accordance with the present disclosure. In some embodiments, the system includes a treatment device body 100 and a head 110 that is removeably attached to the treatment device body 100. The illustrated head 110 has a mounting side facing the treatment device body 100 and an application side carrying an electrode 114, and a dielectric barrier 116 has a first side facing the electrode 114 and a second side facing away from the electrode 114. The cold plasma system 100 may include a plurality of attachable heads 110 for cosmetic treatment over a region of a biological surface 210. The biological surface 210 includes, but is not limited to, skin, hair, fingernails, etc.

In some embodiments, a head 110-$x$ is selected to produce the cold plasma 118 to execute a particular treatment. For example, when treating a relatively small region on the biological surface 210, a size of plasma 118 may be selected to avoid exposing the non-target portion of the biological surface 210 to plasma-generated species. Here, the term "size of plasma" refers to a characteristic or a descriptive dimension of the plasma. For example, for a plasma generated by a round electrode 114, the characteristic dimension of the plasma is related to a diameter of the electrode 114.

Figure 11A:
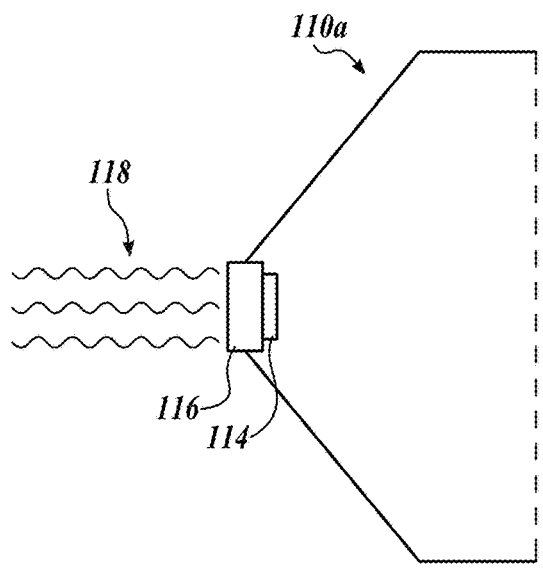
FIG. 11A is a schematic diagram of a cold plasma treatment system in accordance with the present disclosure.

As illustrated in FIG. 11A, a head 110a may be selected and attached to the treatment device body 100. The head 110a tapers from a larger size at the mounting side to a smaller size at the application side. Therefore, the illustrated head 110a generates the plasma 118 having a characteristic size that differs from the diameter of the mounting side of the head 110a. While FIG. 11A illustrates the head 110a having the application side that is smaller than the attachment side, it should be understood that the reverse is also possible. For example, the head 110a may have its application side larger than the attachment side to cause a low intensity treatment over a region of the biological surface 210.

As illustrated in FIG. 11B, a head 110b may include a formula reservoir 180 and an exuding surface 186 on the application side of the head 110b. The exuding surface 186 may be connected to the formula reservoir 180 via one or more conduits 184. In some embodiments, the formula exuding surface 186 includes one or more nozzles on the application side of the head 110b. In some embodiments, the formula exuding surface 186 is a porous material having a void volume to buffer the flow of formula from the formula exuding surface. The porous material may include a cured gel, a soft plastic foam, a rigid plastic foam, a natural porous material such as pumice, etc. In some embodiments, the formula exuding surface 186 may include a vent barred by one or more grills, a wire mesh screen, a patterned perforated screen, etc.

In some embodiments, the formula reservoir 180 is compressed by pressure when the application side of the head 110b is applied to the biological surface 210. In some embodiments, the formula reservoir 180 is compressed by a mechanism enclosed within the head 110b including, but not limited to an electric actuator, a servo, a manually operated lever, a roller, a pair of rollers, etc. In some embodiments, the formula reservoir 180 is removable and interchangeable, and contains a prepared formula tailored to a desired therapeutic or cosmetic result.

In some embodiments, the formula includes one or more cosmetic ingredients. Cosmetic ingredients may include a fragrance, a pigment, a cream, an oil, a natural extract, a moisturizer, etc. In some embodiments, the formula includes one or more medicaments, for example, astringents, pharmaceutically active compounds, acid neutralizing creams, anti-oxidants, etc. In some embodiments, the formula includes one or more protective compounds to protect the biological surface from potentially harmful effects of exposure to the plasma 118. Some non-limiting examples of such protective compounds are an anti-oxidant, a moisturizer, a clarifying cream, an acidity buffering cream, etc.

In one embodiment, the head 110b includes a flexible skirt 170 at the application side of the head 110b. In some embodiments, the flexible skirt 170 is made from corrugated plastic or soft rubber, and attached to the application side of the head 110b. In some embodiments, the flexible skirt 170 is compressed by contacting the biological surface 210. In some embodiments the flexible skirt 170 includes a rigid spacer 174, restricting the compression of the skirt 170, thereby defining a minimum spacing between the head 110b and the biological surface 210. In some embodiments the flexible skirt 170 is impermeable to gases and, when compressed, creates a contained environment for the plasma 118 to form therein. The rigid spacer 174 may be enclosed by the flexible skirt 170 or may be external to it, and may be added or removed. In some embodiments, the rigid spacer 174 includes a conductive material including but not limited to a metal. In some embodiments, the rigid spacer 174 including a conductive material is biased at a voltage greater than or equal to zero. Without being bound to theory, it is believed that the rigid spacer 174 thus biased may allow the plasma to form between the head 110b and the rigid spacer 174, thereby reducing the dose of ions and electrons directed to the biological surface 210. In some embodiments, the plasma 118 discharging into the rigid spacer 174 produces RONS that are contained in the volume defined by the flexible skirt 170.

In one embodiment, the head 110b includes a filter 190 for filtering the plasma 118. The filter 190 may be placed between the head 110b and the biological surface 210, e.g., on a path of the plasma 118 applied to the biological surface.

In some embodiments, the filter 190 is an ultraviolet filter, placed at least partially to block the path of ultraviolet photons from the plasma 118 to the biological surface 210. In some embodiments, the filter 190 blocks ultraviolet photons because the filter is made of UV absorbent or UV scattering material, including, but not limited to, plastic, glass or quartz treated with a UV-blocking film, etc.

In some embodiments, the filter 190 is a chemical filter designed to sequester or convert one or more plasma generated species that would otherwise reach the biological surface 210. In some embodiments, the filter 190 includes a carbonaceous material, non-limiting examples of which include graphene, carbon nanotubes, activated carbon paper, carbon fiber, etc. In another embodiment, the filter 190 includes a catalytic material, non-limiting examples of which include metal particles embedded in a porous matrix. In some embodiments, the filter 190 includes radical scavenging materials, for example, antioxidants, including catalases, glutathione peroxidase, superoxide dismutase (SOD), α-tocopherol (Vit. E), ascorbic acid (Vit. C), β carotene (Vit. A), selenium, etc. In some embodiments, the filter includes a pH sensitive polymer that responds to changes in proton concentration by changing its porosity, surface properties, dimensions, etc. Some non-limiting examples of such pH sensitive polymers include polyacids and polybases, chitosan, hyaluronic acid, and dextran. In some embodiments, the filter responds to changes in pH by opening pores and releasing one or more of the previously described radical scavenging materials.

In some embodiments, the filter 190 includes a liquid formula that is applied to the biological surface 210 upon contact. The liquid formula may include any of the previously mentioned filter materials, carried in a liquid emulsion including but not limited to a cream or an oil. In some embodiments, the liquid formula filter 190 includes additional materials such as cosmetic ingredients, medical ingredients, etc. In some embodiments, the liquid formula includes an indicator material that provides a colorimetric indicator of exposure to plasma generated species. In some embodiments, the indicator material is a pH sensitive dye that will change color when the biological surface 210 has been exposed to a concentration of plasma-generated acidifying or alkalizing species that is sufficient to alter the molecular structure of the dye. Non limiting examples of pH sensitive dye include Gentian violet, Methyl yellow, Methyl red, Cresolphthalein, Indigo carmine, etc.

In some embodiments, the filter 190 includes a charged particle filter placed between the plasma 118 and the biological surface 210 that attracts and neutralizes charged particles present in the plasma 118. In some embodiments, the charged particle filter includes one or more conductive elements, individually biased at a nonzero voltage. Non-limiting examples of a conductive element include a metal screen, a metal probe, a metal ring, etc., placed near or around the dielectric material 116 on the application side of the head 110b. In some embodiments, the charged particle filter selectively filters out positive ions by having a negative polarity, therefore neutralizing the positive ions that approach the surface of the filter 190. In some embodiments, the charged particle filter filters out all charged particles by combining multiple conductive elements, e.g., at least one conductive element carrying a negative polarity and at least one conductive element carrying a positive polarity.

As illustrated in FIG. 11C, the biological surface 210 includes contours that may affect the uniformity of exposure of the region to the plasma 118. Non-limiting examples of contoured biological surfaces 210 include regions on a face and body, including but not limited to convex surfaces such as the cheekbones, the chin, the eyebrows, the nose, the jaw, knuckles, ankles, elbows, knees, etc. Similarly, contoured biological surfaces 210 may include concave surfaces, as in the area beneath the jaw, around the ears, along the neck, etc. In some embodiments, a head 110c includes a conformable material on the application side. The conformable material is configured to reversibly conform to the contours of the region. Non-limiting examples of the conformable material include gel, cured foam, rubber, plastic, etc. In some embodiments, the conformable material on the head 110c includes a consumable material, for example a dry solid, a moisturizing gel, a water soluble cream, etc.

In some embodiments, the application side of the head 110c is reversibly conformable with respect to the biological surface 210. In some embodiments, the dielectric barrier 116 includes a flexible surface, including but not limited to a woven dielectric cloth, such as a glass cloth, a ceramic cloth, etc. In some embodiments, the electrode 114 includes a flexible conductive surface, such as a woven metal cloth, copper mesh, stainless steel mesh, etc. In some embodiments, the flexible surface included in the dielectric barrier 116 is sealed to prevent accumulation of material abraded from the biological surface 210 during the plasma treatment. The flexible surface may be sealed with a coating including, but not limited to, Teflon, $SiO_x$ film, graphene, etc.

As illustrated in FIG. 11D, a head 110d may provide an air cushion between the head 110d and the biological surface 210. In some embodiments, the head 110d includes a plurality of air conduits 164 that at least partially surround the electrode 114 and the dielectric barrier 116. In operation, the air mover 160 provides air to the air conduits 164 (e.g., nozzles, vents, etc.) that direct a vectored flow of air away from the head 110d. The flow of air may create an air cushion that prevents or at least minimizes a contact between the head 110d and the biological surface 210. In some embodiments, the air mover 160 is an electric fan, located within the head 110d. The air mover may operate independently from the electrode 116 and may be turned on and turned off without altering the state of the plasma 118.

Cold Plasma Device with Sensors

Figure 12:
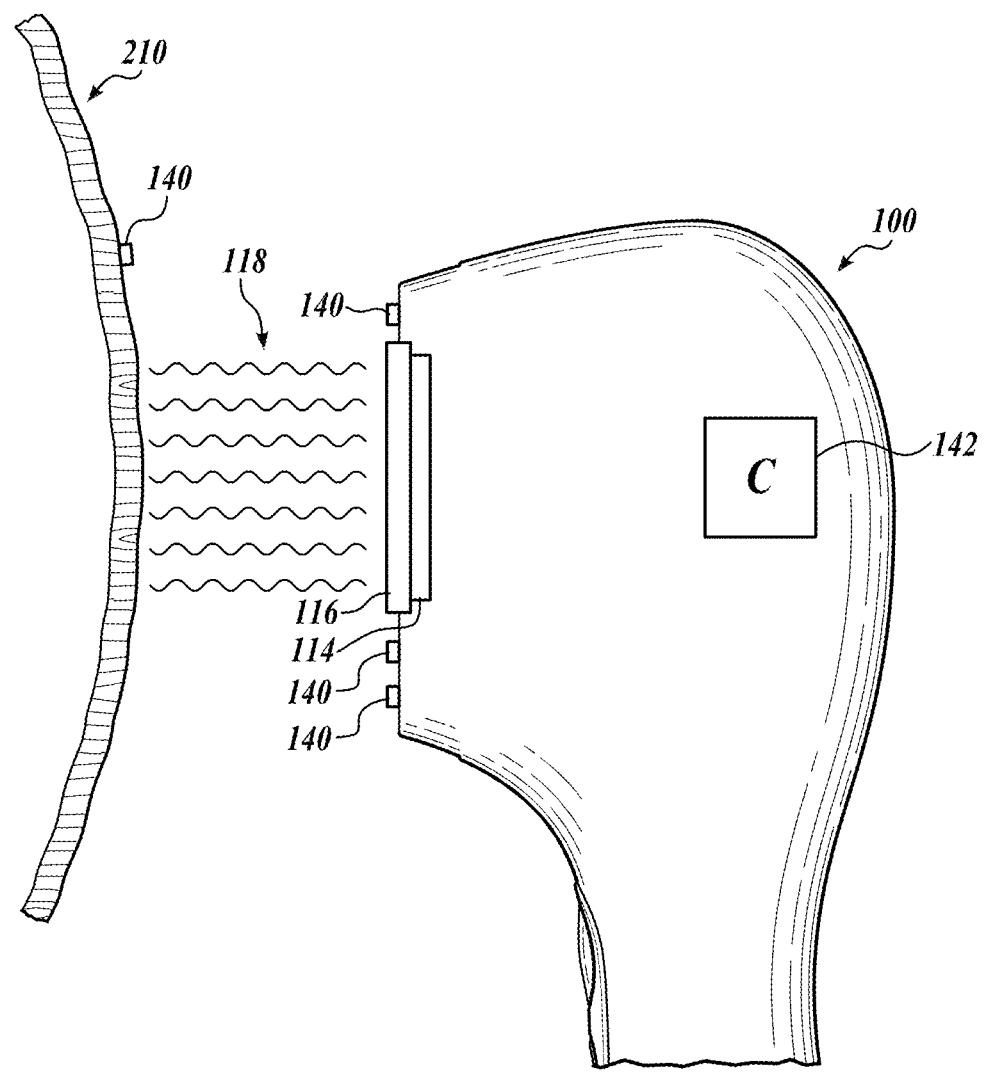
FIG. 12 is a schematic diagram of a cold plasma treatment system in accordance with the present disclosure.

FIG. 12 is a schematic diagram of a cold plasma treatment system in accordance with the present disclosure. In some embodiments, the cold plasma treatment device 100 includes one or more sensors 140 to measure plasma parameters. Based on the measured plasma parameters, a controller 142 may control the cold atmospheric plasma 118 and maintain a predetermined cosmetic treatment over a region of a biological surface 210.

As previously described, in some embodiments, the cold atmospheric plasma 118 is formed using the biological surface 210 as a floating reference electrode. Without being bound to theory, it is believed that such an arrangement is sensitive to non-uniform distribution of water and ion concentrations over the biological surface 210. It is believed that a localized region that is relatively rich in ions, such as a sweat gland, may provide a preferred conductive path for plasma-generated charged species, and the cold atmospheric plasma 118 may form preferentially at such a site on the biological surface 210. In turn, plasma preference for a particular location over another on a biological surface 210 introduces poorly controlled non-uniformity in treatment and variability in plasma dosage over the region treated by the plasma 118. It is believed that uniformity is an important criterion in the operation of a cold atmospheric plasma source. Therefore, in at least some embodiments, the design of the plasma treatment device 100 takes into account the sensitivity of the cold atmospheric plasma 118 to variations in properties of the surface 210.

Uniformity of the plasma 118 is defined in terms of a variability of one or more plasma parameters, for example, discharge power, discharge volume, the concentrations of plasma generated species, etc. In a highly variable system, for example, where the treatment region contains many discrete sub-regions of disparate properties, the plasma treatment device 100 may exhibit discontinuities in the discharge current or discharge voltage as the plasma treatment device 100 translates between ion-rich and ion-poor sub-regions of the surface 210. Without being bound to theory, it is believed that a plasma source, passing over a conductive sub-region may exhibit a spike in discharge current and a corresponding drop in discharge voltage.

In some embodiments, the controller 142 actuates an electronic ballast circuit, connected to the electrode 114. Without being bound to theory, it is believed that an electronic ballast circuit may permit the controller 142 to regulate the current to electrode 142, thereby preventing thermal runaway of the plasma 118 and constriction of the plasma 118 at one or more localized spots on the biological surface 210.

As illustrated in FIG. 12, which demonstrates an embodiment of the inventive technology, the plasma source 100 incorporates one or more sensors 140 to measure parameters of a cold atmospheric plasma 118 and a biological surface 210. In some embodiments, the plasma treatment device 100 includes sensors 140 that measure plasma parameters. The plasma parameters may include measurements of the electric current discharged into the biological surface 210, the voltage drop between the dielectric barrier 116 and the surface 210. The plasma parameters may include one or more parameters indicative of the energy density of the plasma 118, such as the spectrum of light emitted by the plasma 118, the ion-density in the plasma 118, or variation in time of the prior-mentioned parameters that would indicate non-uniform surface treatment. Without being bound to theory, it is believed that one or more short-lived discontinuities in the discharge voltage or discharge current indicates a non-uniformity in the form of preference of the cold atmospheric plasma 118 for one or more highly localized ion-rich regions on the surface.

In some embodiments, one or more sensors 140, placed on the surface 210 at or near the treatment region, measure parameters of the plasma 118 or of the biological surface 210. For example, the plasma treatment device 100 may include ion sensors, such as pH sensors or chloride sensors, light sensors, reactive oxygen sensors, a surface temperature sensor, a distance sensor, humidity sensors, etc.

In some embodiments, sensors 140 placed either on the surface 210 or on the plasma treatment device 100 measure the ambient environment. Such sensors 140 may include ion sensors, light sensors, reactive oxygen sensors, temperature sensors, humidity sensors, etc.

In some embodiments, a position reference sensor placed on the plasma treatment device 100 is operably coupled to a distance sensor on the biological surface 210. The position reference sensor may determine the distance of the dielectric barrier 118 from the surface 210. In some embodiments, a distance sensor, such as a laser rangefinder included in the plasma treatment device 100, measures the distance from the dielectric barrier 118 to the surface 210.

In some embodiments, the sensors 140 communicate with the controller 142, as part of the plasma source 110. The controller 140 may be operably coupled to the plasma treatment device 100, and may receive input from the sensors 140 and process that input to determine control data for the plasma treatment device 100. In some embodiments, the control data includes, but is not limited to, signals sent to electronic components of the plasma treatment device 100 to modulate the current or the voltage provided to the electrode 116, and signals sent to other components of the plasma treatment device 100 to produce a perceptible signal. In some embodiments, the perceptible signal is a haptic feedback or an audible or visible indicator. In some embodiments, the controller 142 sends control data in response to an unsafe dose of energy or reactive species produced by the plasma 118.

As previously described, without being bound to theory, a plasma dose is believed to determine exposure to one or more plasma generated species such as, reactive chemical species, energetic species including ions and electrons, photons, etc.

In some embodiments, a plasma dose is a concentration of a given species imparted to a given region on the biological surface 210 over a period of time, expressed as a number per unit-area, per unit-time (such as "per square-centimeter seconds"). In some embodiments, the controller 142 determines a treatment duration and control data to send to the plasma treatment device 100, by integrating the plasma dose over the area of the dielectric barrier 116, to provide a plasma dose per unit time.

In some embodiments, when the plasma treatment device 100 remains over a given region on the biological surface 210 for a length of time such that the plasma 118 is likely to harm the surface 210, the plasma treatment is considered unsafe. Conversely, in some embodiments, if the treatment device 100 remains over the given region for a length of time such that the plasma 118 is unlikely to have the desired effect, the plasma treatment is considered to have provided an ineffective dose. In some embodiments, these doses are not unique values, but rather are thought to occur in ranges. As such, a controller 142 may determine an unsafe range or an ineffective range of doses, wherein it will send control data to the plasma treatment device 100 to produce a perceptible signal or to modulate the plasma 118, or both.

In some embodiments, the plasma 118 may be applied for a given period of time such that, for example, the application time corresponds to a half-life of the plasma. In other embodiments, the strength of the plasma 118 that is applied to the biological surface may be controlled by limiting the application of the plasma to a period of time after a certain decay of the plasma strength. For example, the plasma 118 may be applied after the half-life of the plasma has already passed.

In some embodiments, the controller 142 responds to an unsafe dose by sending a signal for the source to be moved away from the region on the biological surface 210 toward a second region. The controller 142 may respond to an unsafe dose by sending control data to the electronic components of the plasma treatment device 100 to turn off the plasma 118, or to modulate the power provided to the electrode 114 to diminish the generation of energetic species and reactive species in the plasma 118.

Figure 13:
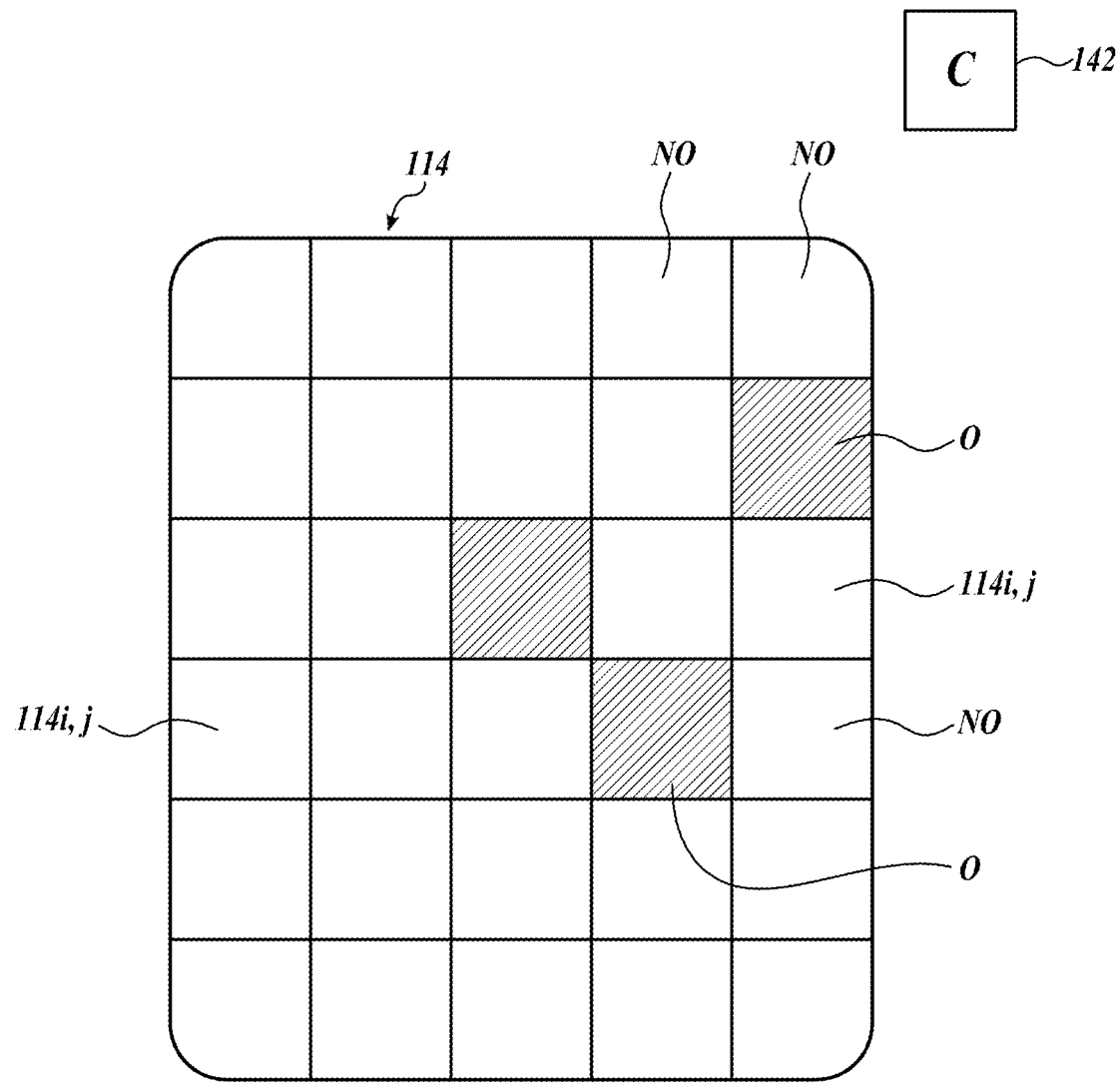
FIG. 13 is a schematic diagram of a cold plasma electrode system in accordance with the present disclosure.

In some embodiments the plasma 118 is generated by a plurality of pixelated electrodes 114$i,j$ arranged in a matrix, as shown in FIG. 13. The pixelated electrodes may be individually addressable by the controller 142, where the controller determines a discharge power for a given pixelated electrode 114. In some embodiments, the controller uses input from current and voltage sensors 140 for the pixelated electrodes 114$i,j$ to counteract non-uniform plasma 118 constriction or localization. In some embodiments, when the plasma 118 localizes to a spot on the biological surface 210 having disparate chemical or physical properties, the controller 142 receives input indicating which pixelated electrodes 114$i,j$ are drawing a disproportionate rate of electrical power, relative to the average for the matrix 114. The controller 142 may modulate the plasma 118 by turning off the electrodes 114$i,j$ that are drawing excess power, thereby distributing plasma energy to operational electrodes O, and diminishing the undesirable effects of plasma non-uniformity near the non-operational electrodes NO.

The components of the cold plasma system 100 may communicate directly through wired and powered connections. These components may communicate to each other via a network (not shown), which may include suitable communication technology including, but not limited to, wired technologies such as DSL, Ethernet, fiber optic, USB, and Firewire; wireless technologies such as WiFi, WiMAX, 3G, 4G, LTE, and Bluetooth; and the Internet.

Figure 14:
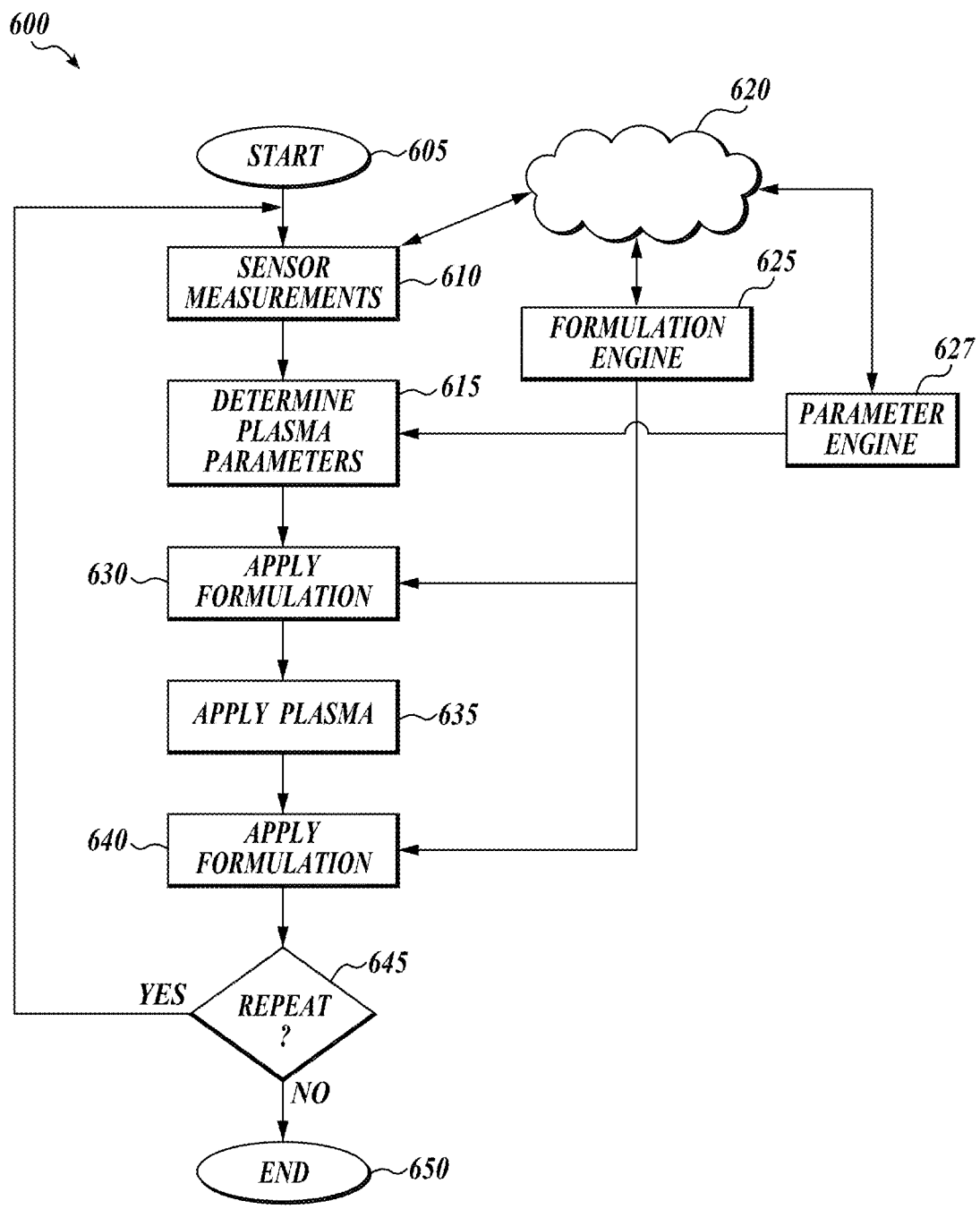
FIG. 14 is a flowchart of a method of cold plasma treatment according to the present disclosure.

In some embodiments, the controller 142 includes a non-transitory computer readable medium having computer executable instructions and data stored thereon that cause, in response to execution by one or more processors of a computing device, the computing device to implement a method of treatment 600 as described herein and illustrated in FIG. 14.

FIG. 14 is a flowchart of a method of cold plasma treatment according to the present disclosure. In some embodiments, the method of treatment 600 of the region of the biological surface 210 with the cold atmospheric plasma 118 includes generating the cold plasma between the plasma treatment device 100 and the region. The method of treatment 600 may include measuring one or more treatment parameters with one or more sensors 140 and determining a plasma dose from the treatment parameters. In some embodiments, the method of treatment 600 includes modulating one or more of the treatment parameters to adjust the plasma dose, and switching off the cold atmospheric plasma 118.

In some embodiments, the method may include additional steps or may be practiced without all steps illustrated in the flow chart. The method starts at block 605, and proceeds to block 610 where one or more sensors 140 measure treatment parameters, for example, ambient parameters and surface parameters. In some embodiments, prior to generating the plasma 118, the method 600 includes placing at least one sensor 140 onto the biological surface 210 at or near the region. As previously described, the sensors 140 may be operably coupled to the controller 142, and may provide sensor input to the controller 142 to be used in block 615 to determine plasma parameters necessary for effective treatment. In some embodiments, the plasma parameters are defined by default values, and the controller 142 does not act until the plasma 118 has been turned on. In some embodiments, the plasma parameters include a discharge voltage as a function of time, a discharge current as a function of time, a plasma temperature as a function of time, or a gas temperature near the region as a function of time. In some embodiments, the sensor measurements are provided to a data storage system 620, which may aggregate the measurements with other sensor data. In some embodiments, a parameter engine communicates parameter information to the controller 142 as shown in block 627. The parameter engine determines a treatment dose based on aggregate sensor inputs accumulated and stored in a data storage system 620, and further determines a set of plasma parameters that are provided to the controller 142.

In block 630, a cosmetic formulation is applied to the treatment region. In some embodiments, the cosmetic formulation enhances plasma treatment. In some embodiments, the cosmetic formulation protects the biological surface 210 from harmful aspects of the plasma 118. A formulation engine, shown in block 625, may determine the formulation, which may receive input from the data storage system 620. In some embodiments, the formulation engine applies machine learning to optimize the components of the formulation for a given purpose such as radical scavenging, UV absorption, electrical conductivity, thermal conductivity, etc.

In block 635, the plasma treatment device 100 applies the cold atmospheric plasma 118 to the biological surface 210 at the treatment region. In block 640, a post-plasma formulation is applied to the treatment region of the biological surface 210. As in block 630, the formulation may be determined by a formulation engine as shown in block 625. In some embodiments, the post-plasma formulation may be the same as the formulation of block 630. In some embodiments, the post-plasma formulation may be different from the formulation of block 630. In some embodiments, the post-plasma formulation neutralizes ions and moisturizes the biological surface 210. In some embodiments, the post-plasma formulation counteracts possible oxidative effects of plasma treatment by including anti-oxidant ingredients.

In block 645, the treatment may be repeated. In some embodiments, the controller 142 determines whether the treatment dose has been met at block 645. Where the treatment dose has not been met, the controller 142 may repeat the sensor measurements, determine new plasma parameters, and modulate the plasma to provide an effective and safe dose of plasma generated species. In some embodiments, the treatment is not repeated, and the method ends in block 650.

The controller 142 may determine plasma parameters from a group including a current provided to the electrode 114, a driving frequency, a voltage waveform, a peak to peak voltage, a root mean square voltage, a plasma temperature, a gas temperature, optical emission from the plasma 118, etc.

In some embodiments, the controller determines an indicator of uniformity of the cold atmospheric plasma 118. As previously described, uniformity describes the spatial distribution of plasma 118 between the second side of the dielectric barrier 116 and the biological surface 210, as well as whether a time-averaged flow of current between the two surfaces is evenly spread across the treated region on the biological surface 210. In some embodiments, the controller sends control data to the plasma treatment device 100 to modulate one or more of the plasma parameters in response to changes in the indicator of uniformity. The controller may determine the indicator of uniformity intermittently, based on sensor inputs provided to the controller 142.

As understood by one of ordinary skill in the art, a "data storage system" as described herein may be any suitable device configured to store data for access by a computing device. An example of the data storage system 620 is a high-speed relational database management system (DBMS) executing on one or more computing devices and being accessible over a high-speed network. However, other suitable storage techniques and/or devices capable of providing the stored data in response to queries may be used, and the computing device may be accessible locally instead of over a network, or may be provided as a cloud-based service. The cloud storage system 620 may also include data stored in an organized manner on a computer-readable storage medium.

In general, the word "engine," as used herein, refers to logic software and algorithms embodied in hardware or software instructions, which can be written in a programming language, such as C, C++, COBOL, JAVA™, PHP, Perl, HTML, CSS, JavaScript, VBScript, ASPX, Microsoft-.NET™, PYTHON, and/or the like. An engine may be compiled into executable programs or written in interpreted programming languages. Software engines may be callable from other engines or from themselves. Generally, the engines described herein refer to logical modules that can be merged with other engines, or can be divided into sub engines. The engines can be stored in any type of computer readable medium or computer storage device and be stored on and executed by one or more general purpose computers, thus creating a special purpose computer configured to provide the engine or the functionality thereof.

Generating Cold Plasma Away from Skin of User

Figure 15:
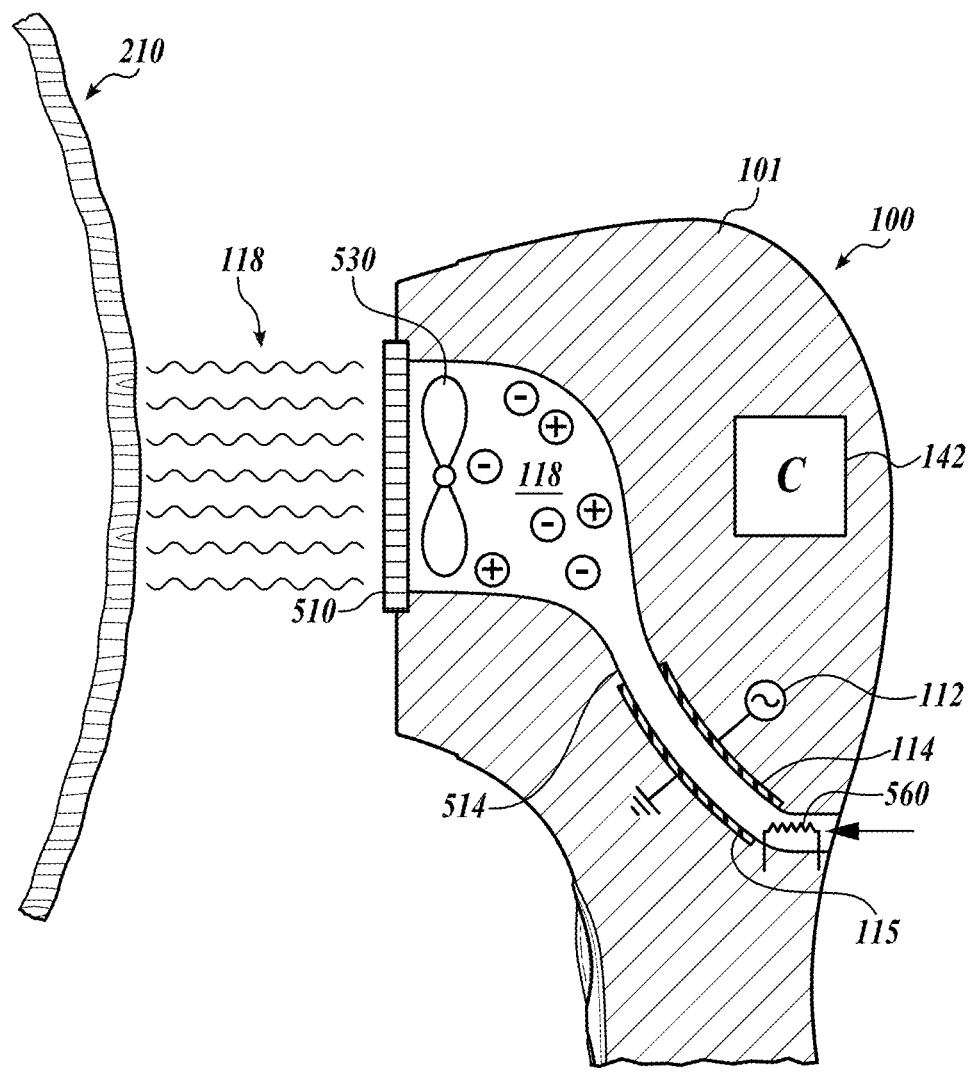
FIG. 15 is a schematic diagram of a cold plasma treatment system in accordance with the present disclosure.

FIG. 15 is a schematic diagram of the cold plasma treatment system in accordance with the present disclosure. In some embodiments, the cold plasma treatment device 100 houses the electrodes 114 and 115 in a housing 101. In some embodiments, the electrodes 114 and 115 are disposed along an air conduit 514, such that the electrodes 114 and 115 are on the opposite sides of the air conduit 514. In different embodiments, the air conduit 514 may contain other gases, not just air, that are flown by the electrodes 114 and 115. Therefore, reference to the "air conduit" encompasses other gases flowing through the conduit 514. In operation, an air mover 530 (e.g., an air fan, a blower, an ionic wind blower, a source of compressed air, a source of compressed gas, etc.) can move air from the outside environment through the air conduit 514 and out of the cold plasma treatment device 100.

Moving the air along the air conduit 514 subjects the air to the electromagnetic field generated by the electrodes 114 and 115 of the cold plasma generator. When the electrodes 114 and 115 are properly energized, for example using an alternate current (AC) source which may be a radio frequency (RF) source 112, cold plasma is generated within the air conduit 514. Thus generated cold plasma 118 can be expelled from the cold plasma treatment device 100 by the air mover 530.

In some embodiments, the RF source 112 is adjusted such the plasma 118 is applied over the target biological surface for a given period of time such that, for example, the application time corresponds to a half-life of the plasma. In other embodiments, the RF source 112 is adjusted such the plasma 118 is adjusted such that the plasma 118 is applied after the half-life of the plasma has already passed (e.g., by taking the travel time of the plasma into account).

In some embodiments, there is a no single half-life that characterizes the cold-plasma; each compound in the plasma may have different half-life. Therefore, target concentration is affected by half-life of each compound, residence time between passes, etc. Therefore, in some embodiments, the term "half-life" corresponds to a "half-life" of a component or components of choice. In other embodiments, the term "half-life" refers to an average or collective half-life of the mixture of components. Moreover, half-life itself will also depend on the available decay reactions which can depend on the local microenvironment (including concentration and composition of other species).

The cold plasma treatment device 100 may include a plasma barrier 530. In some embodiments, the plasma barrier 510 may be perforated to, for example limit and/or regulate the flow of the cold plasma 118 toward the biological surface 210. The plasma barrier may be a vent barred by one or more grills, a wire mesh screen, a patterned perforated screen, etc. The perforation size of the plasma barrier 510 may be selected based on the target flow rates of the cold plasma 118. In different embodiments, the plasma barrier 510 may be made of different materials, for example metals or plastics.

In some applications, generating the cold plasma away from the biological surface 210 (e.g., away from the skin of the user) may be advantageous in comparison to generating the cold plasma proximately to the biological surface 210. When the cold plasma is generated away from the biological surface 210, the concentration, temperature, pressure, etc., of the plasma does not have to be as tightly controlled as with the plasma that is generated directly at the biological surface 210. For example, whereas the temperature of the air that carries the cold plasma toward the biological surface 210 has to be within a relatively narrow range (to avoid discomfort to the user), the available range of temperatures for the incoming air is wider when the plasma is generated away from the biological surface. After the plasma has been generated, the temperature of the air may be lowered or raised to a more acceptable range while the plasma is still contained within the housing 101. Analogously, in some embodiments, the concentration of the RONS or other plasma species may be higher for the plasma generated away from the biological surface 210, because the concentration of the plasma species can be reduced inside the housing 101 before the cold plasma reaches the biological surface 210. For example, the concentration of the plasma species and the temperature of the air will generally decrease with time elapsed from the creation of the plasma species. Therefore, by controlling a speed of the air mover 530, a length of the air conduit 514, and/or a voltage of the AC source 112 the concentration or the temperature of the plasma species can also be controlled.

In some embodiments, the concentration of the plasma species is a function, at least in part, of the temperature of the incoming air. The temperature may be controlled by a heater 560. In some embodiments, the controller 142 may control different parameters that affect generating the cold plasma (e.g., voltage of the AC source 112, speed of the air mover 530, voltage at the heater 560, etc.).

Figure 16:
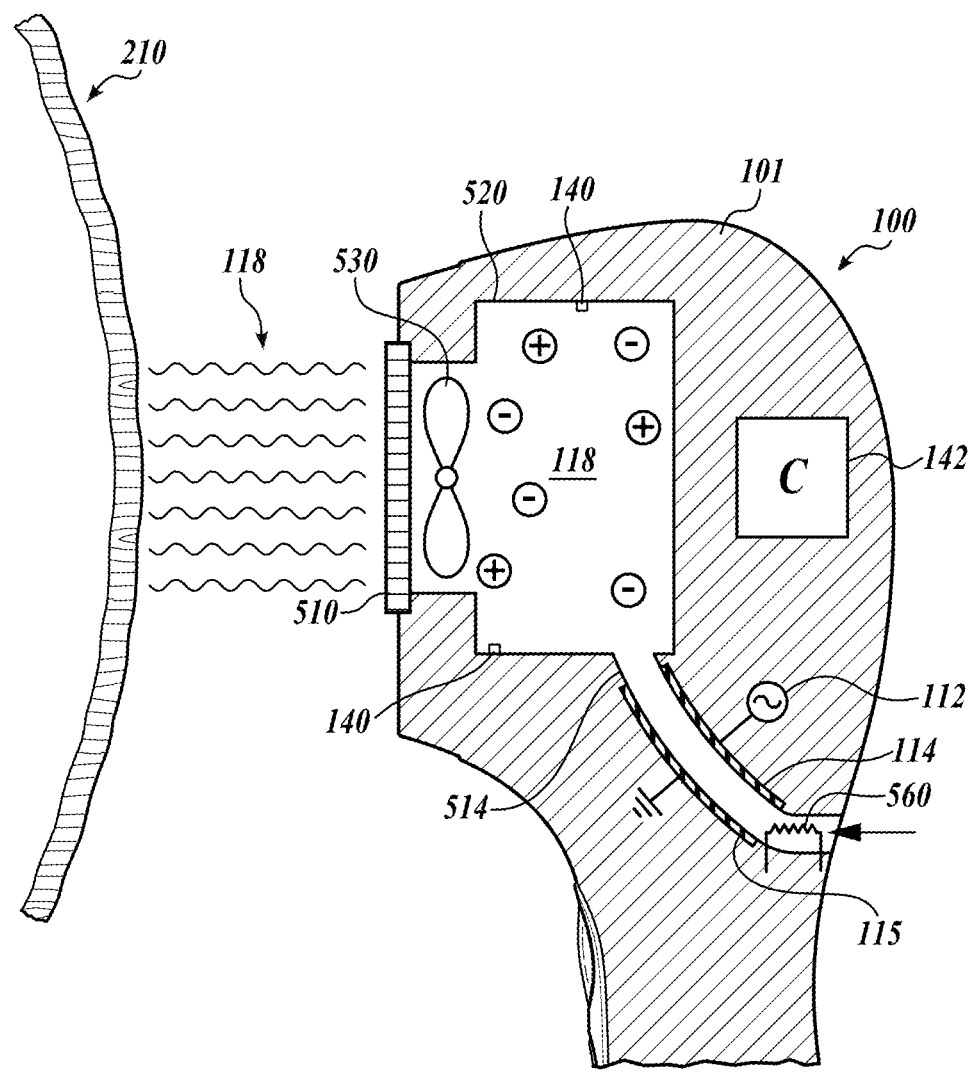
FIG. 16 is a schematic diagram of a cold plasma treatment system in accordance with the present disclosure.

FIG. 16 is a schematic diagram of the cold plasma treatment system 100 in accordance with the present disclosure. The illustrated cold plasma treatment system 100 includes a reservoir 520 for temporary storage of the cold plasma before exhausting the cold plasma toward the biological surface 210. By storing the cold plasma in the reservoir 520, the time elapsed from generating the cold plasma till exhausting the cold plasma from the system 100 may be better controlled. As a result, in at least some embodiments, the concentration and/or temperature of the cold plasma species may also be better controlled.

In some embodiments, the reservoir 520 may have one or more sensors that sense the state of the cold plasma. For example, the sensors 140 may sense concentration of the cold plasma, temperature, pressure, composition, etc. In operation, the controller 142 may adjust parameters for generating the cold plasma (e.g., voltage of the AC source 112, speed of the air mover 530, temperature of the heater 560) to achieve desired parameters of the cold plasma 118 at the biological surface 210.

Figure 17:
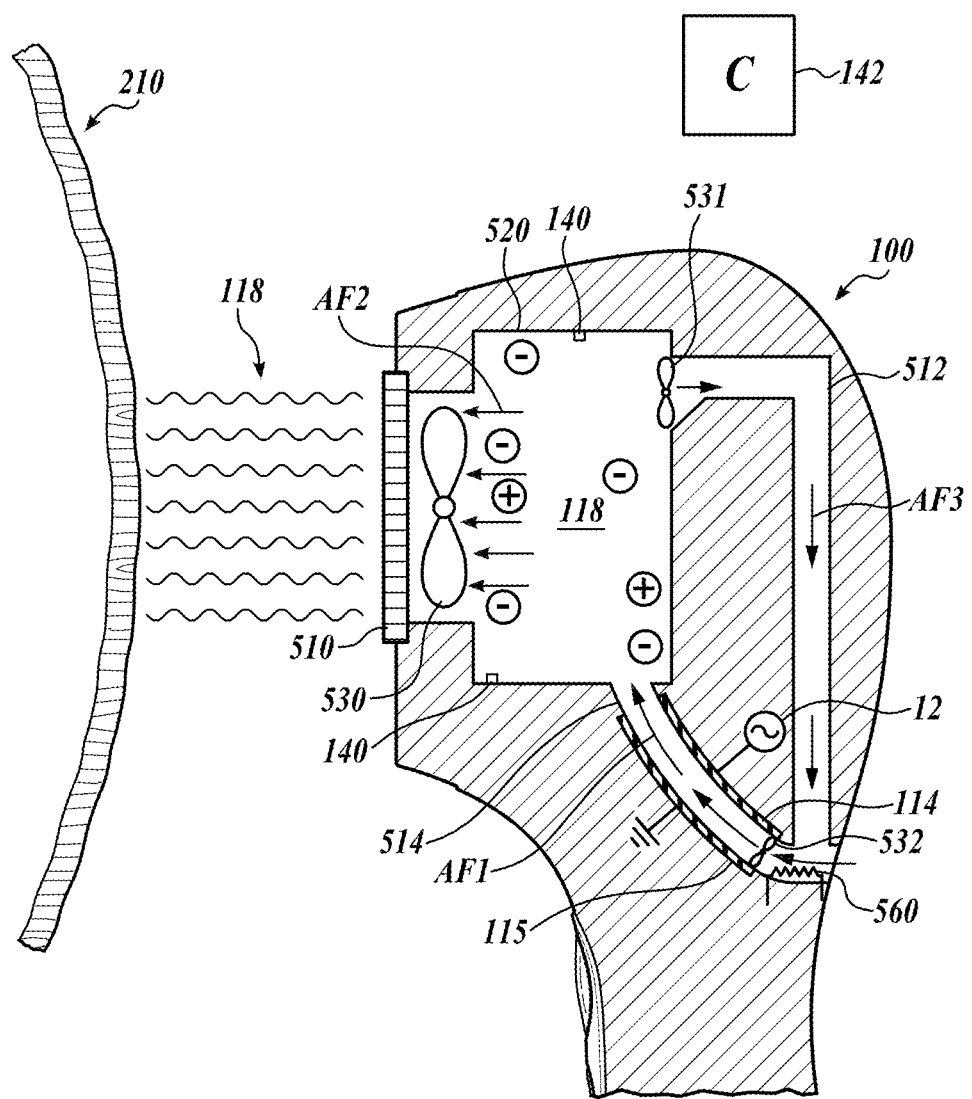
FIG. 17 is a schematic diagram of a cold plasma treatment system in accordance with the present disclosure.

FIG. 17 is a schematic diagram of the cold plasma treatment system 100 in accordance with the present disclosure. In the illustrated embodiment, an additional air conduit 512 connects the reservoir 520 with the air conduit 514, therefore providing a return path for the plasma species back toward the electrodes 114 and 115. In some embodiments, the air conduit 512 provides for better control of the concentration and/or temperature of the cold plasma in the reservoir 520. For example, if the sensors 140 detect that the concentration of the plasma species in the reservoir 520 is insufficient, the controller 142 may increase the rotational speed of the air mover 531, therefore routing more air and plasma back to the electrodes 114 and 115 to generate additional plasma species in the stream of air entering reservoir 520. Furthermore, the speed of the air mover 732 may be adjusted to control flow of air and plasma to the reservoir 520. In some embodiments, the speed of the air mover 530 may be adjusted to vary the outflow of the plasma species out of the reservoir 520. The controller 142 may additionally control the heater 560 to control the temperature of the air and the cold plasma species inside the reservoir 520. A reflow (recirculation) of the plasma species can also increase the concentration of plasma species. In some embodiments, this reflow processing of the same stream increases concentrations of species with each processing pass, while reducing the amount of unstable species that decay during each reflow. In some embodiments, these additional control mechanisms improve the control of the cold plasma concentration, temperature, types of the cold plasma species (e.g., ROS-dominated, RNS-dominated), pressure in the reservoir 520, and other parameters of the cold plasma.

Figure 18:
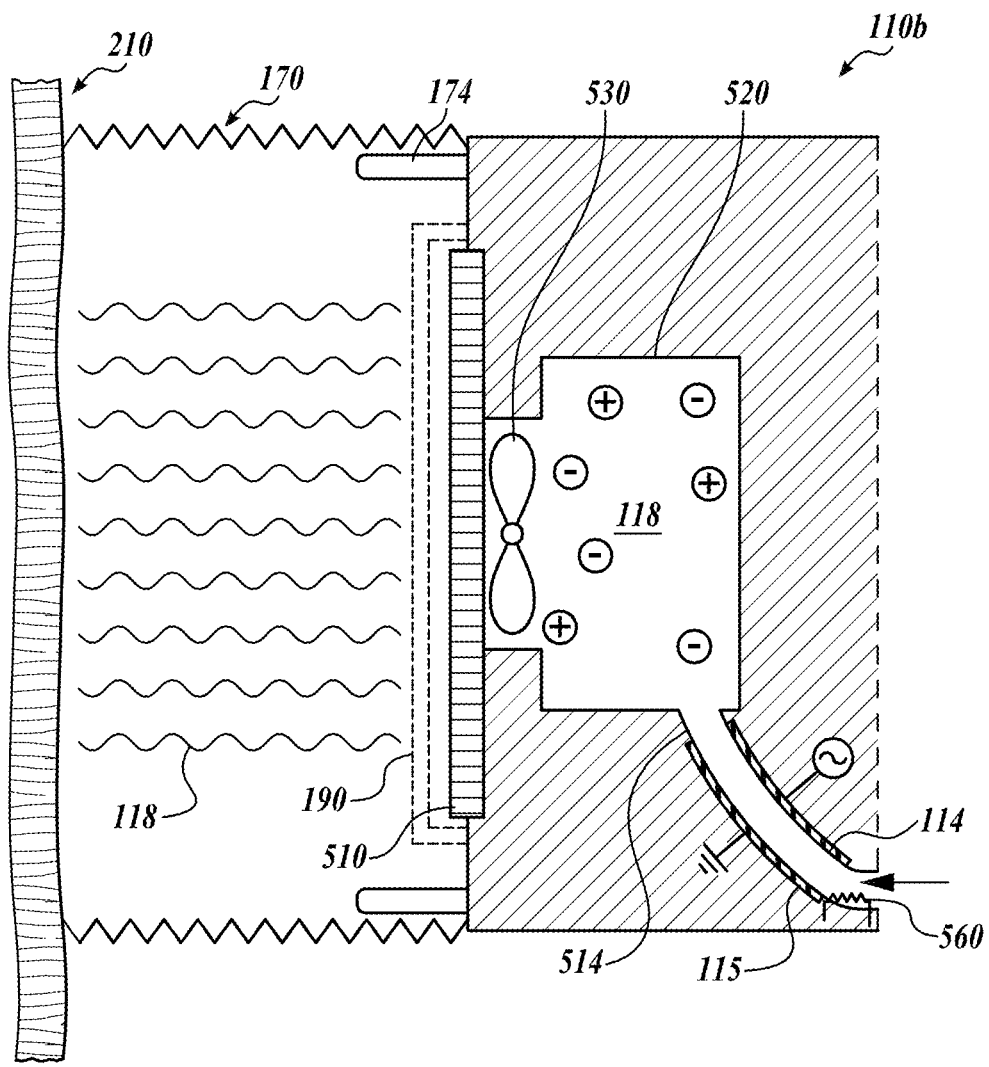
FIG. 18 is a schematic diagram of a cold plasma treatment system in accordance with the present disclosure.

FIG. 18 is a schematic diagram of the cold plasma treatment system 100 in accordance with the present disclosure. In some embodiments, the cold plasma treatment system 100 includes a flexible skirt 170. The flexible skirt 170 may be made from corrugated plastic or soft rubber, and attached around the plasma barrier 510 to contain the cold plasma 118 proximate to the biological surface 210. For example, the flexible skirt 170 may be impermeable to gases and, when compressed, may create a contained environment for the plasma 118. In some embodiments, the flexible skirt 170 is compressed by contacting the biological surface 210.

In some embodiments, the cold plasma treatment system 100 includes a rigid spacer 174, restricting the compression of the flexible skirt 170, thereby defining a minimum spacing between the plasma barrier 510 and the biological surface 210. The rigid spacer 174 may be enclosed by the flexible skirt 170 or may be external to it, and may be removable. In some embodiments, the rigid spacer 174 includes a conductive material including but not limited to a metal. In some embodiments, the rigid spacer 174 including a conductive material is biased at a voltage greater than or equal to zero. Without being bound to theory, it is believed that the rigid spacer 174 thus biased may electromagnetically shape the space for the plasma containment between the plasma barrier 510 and the biological surface 210, thus controlling the contact between the cold plasma and the biological surface. The rigid spacer 174 can have adjustable length for different applications. All else being the same, longer rigid spacers apply "older" plasma to skin, whereas shorter rigid spaces apply "fresher" plasma.

In one embodiment, the cold plasma treatment system 100 includes a filter 190 for filtering the plasma 118. The filter 190 may be placed between the plasma barrier 510 and the biological surface 210. In some embodiments, the filter 190 is a charged particle filter placed between the plasma 118 and the biological surface 210 that attracts and neutralizes charged particles present in the plasma 118. In some embodiments, the charged particle filter includes one or more conductive elements, individually biased at a nonzero voltage. Non-limiting examples of a conductive element include a metal screen, a metal probe, a metal ring, etc., placed near or around the plasma barrier 510. In some embodiments, the charged particle filter selectively filters out positive ions by having a negative polarity, therefore neutralizing the positive ions that approach the surface of the filter 190. In some embodiments, the charged particle filter filters out all charged particles by combining multiple conductive elements, e.g., at least one conductive element having a negative polarity and at least one conductive element having a positive polarity.

Figure 19:
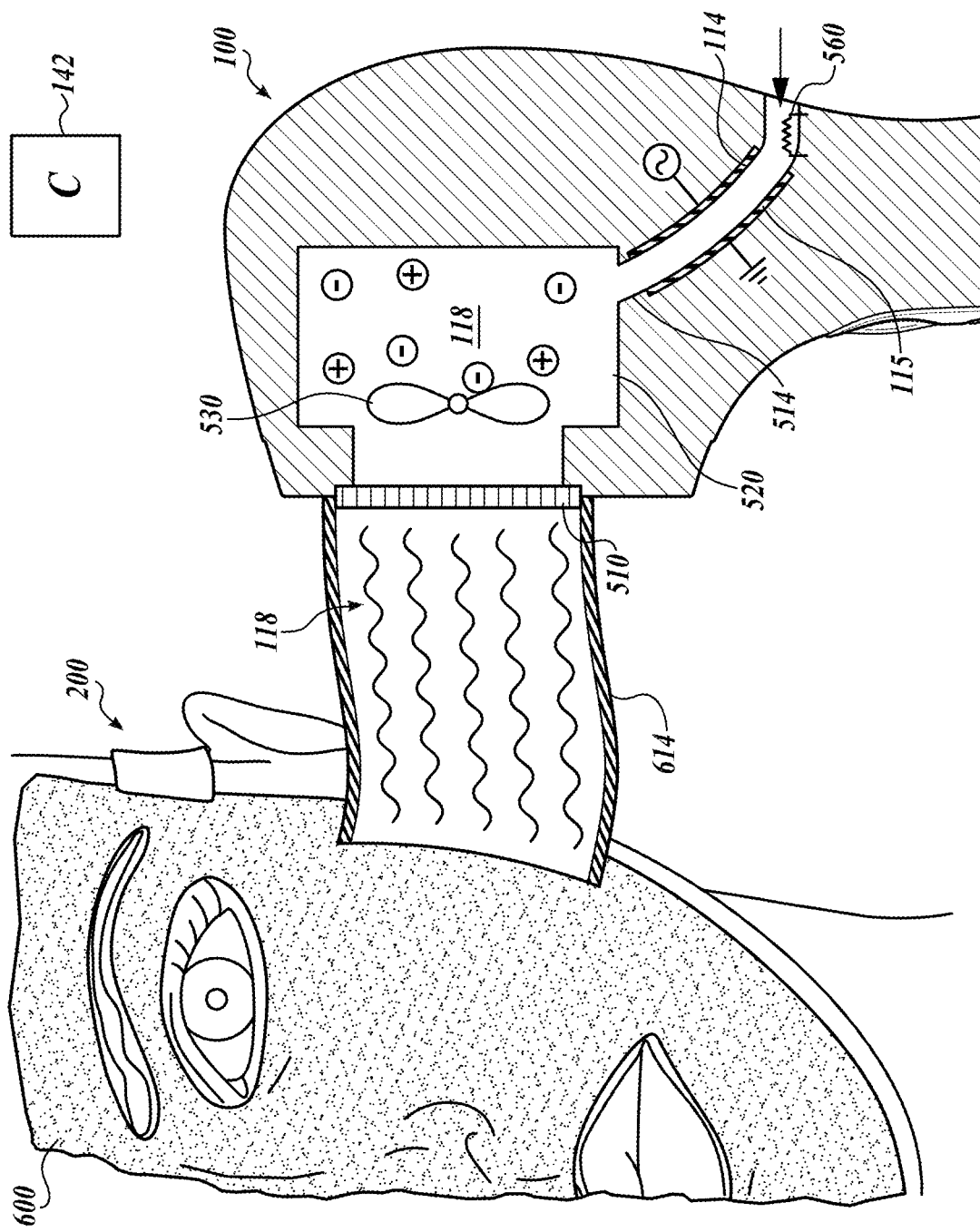
FIG. 19 is a schematic diagram of using a cold plasma treatment system in conjunction with a face mask in accordance with the present disclosure.

FIG. 19 is a schematic diagram of using the cold plasma treatment system 100 in conjunction with a face mask in accordance with the present disclosure. In the illustrated embodiment, a face mask 600 covers the face of the subject under the treatment (e.g., a consumer 200). The cold plasma that is directed from the cold plasma treatment system 100 enters the space between the face mask 600 and the biological surface 210 through a mask intake 614. In some embodiments, the face mask 600 provides a containment boundary that prevents or at least reduces the escape of the cold plasma 118 away from the biological surface (e.g., the person's skin). As a result, the cold plasma may stay in contact with the biological surface for longer time, therefore having a greater effect. In some embodiments, the cold plasma may be propelled through the mask intake 614 and toward the face mask 600 by the air mover 530.

Generating Cold Plasma from Cartridge Containing Plasma Precursor

Figure 20:
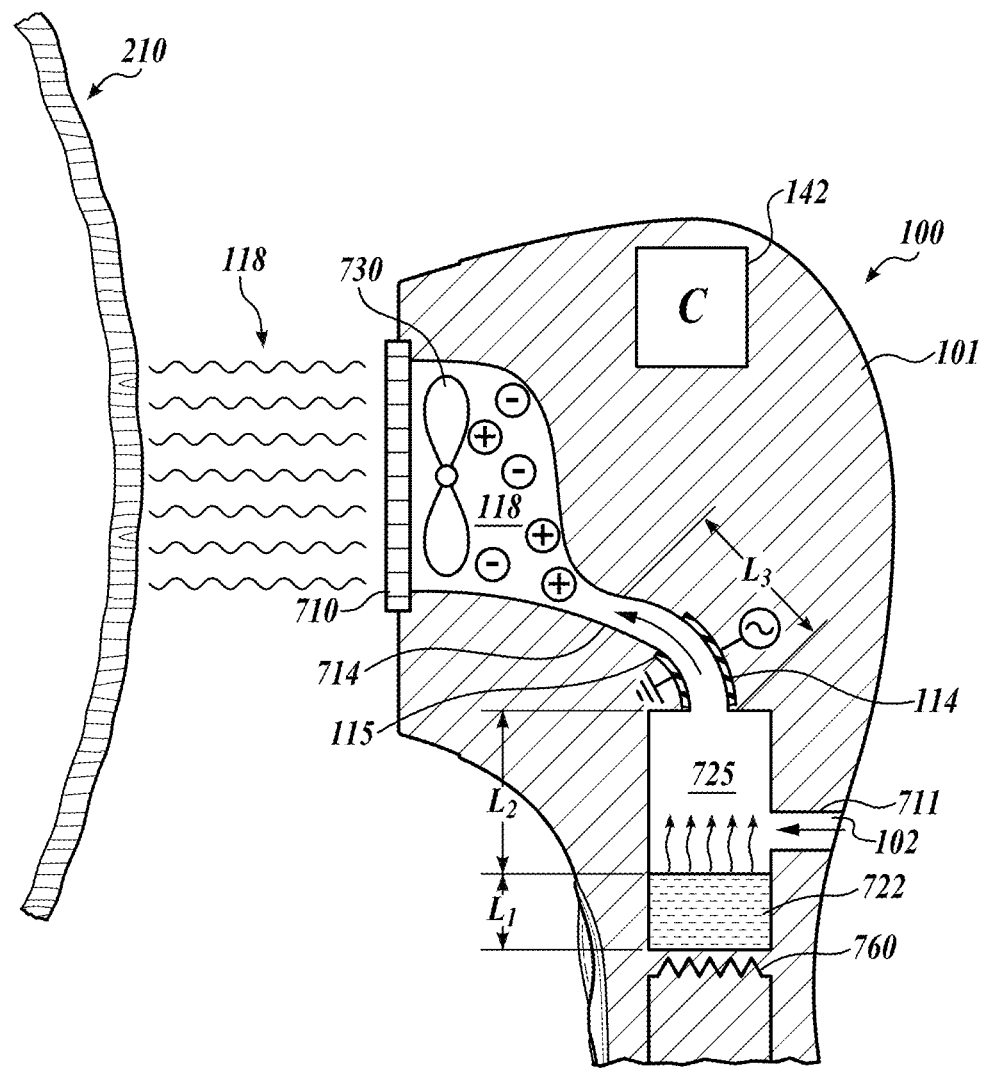
FIG. 20 is a schematic diagram of a cold plasma treatment system in accordance with the present disclosure.

FIG. 20 is a schematic diagram of the cold plasma treatment system in accordance with the present disclosure. In some embodiments, the cold plasma treatment system 100 houses a precursor cartridge 725 in a housing 101. The cartridge 725 contains the cold plasma precursor 722 that is transported toward the electrodes 114 and 115 that generate cold plasma by an electromagnetic field. The cartridge 725 may also include components that are not direct precursors to the plasma components, but, instead, enhance or augment the activity of plasma. For example, the cartridge 725 may include compounds that stabilize (increase half-life) of desirable plasma components. Such compounds may enhance the effect of plasma components by, for example, lowering the pH on the skin surface. Conversely, precursor components may, upon incorporation into the plasma stream, scavenge the undesirable plasma compounds (such as ozone) or otherwise transform these plasma components into inert forms.

In some embodiments, the electrodes 114 and 115 are disposed along an air conduit 714, such that the electrodes 114 and 115 are on the opposite sides of the air conduit 714. In one embodiment, the electrodes 114 and 115 are energized by an alternate current (AC) source 112.

In some applications, generating the cold plasma from the precursor(s) 722 may improve selectivity of generating the target species in the plasma, resulting in more specific target species. For example, the precursor 722 may be an oxygen-rich or a nitrogen-rich compound that, after ionization by the electrodes 114 and 115, produces a reactive oxygen species (ROS) or a reactive nitrogen species (RNS) in the cold plasma 118. Collectively, the ROS and RNS are referred to as the reactive oxygen and nitrogen species (RONS).

RONS are typically generated in the plasma from the precursor formulas, because RONS are usually not shelf stable. However, the precursor formula may include stable compounds (e.g., oxygen reach or nitrogen reach components) that can give rise to RONS and/or a different composition of RONS as the plasma is generated. The RONS are believed to interact in differing ways with the biological surfaces, therefore causing different effects on the biological surfaces. A non-exhaustive list of RONS includes: hydroxyl (OH), atomic oxygen (O), singlet delta oxygen (O2(1Δ)), and superoxide (O2-). In some embodiments, the precursors 725 that produce the RONS may include hydrogen peroxide ($H_2O_2$) and nitric oxide (NO). Conversely, in some embodiments, the precursor 722 may cause suppression of certain (e.g., undesired) plasma species. In different embodiments, the precursor 722 can be tailored for treating acne, wrinkles, improving skin rejuvenation, and causing other desired effects at the biological surface 210.

In some embodiments, the precursor 722 is a liquid that evaporates into a gas (vapor), and flows toward the electrodes 114 and 115. In some embodiments, the flow of the precursor gas is improved by an incoming air that is drawn through an opening 102, via an air conduit 711 and into the precursor cartridge 725. The mixture of the precursor gas and air may be further drawn into the air conduit 714, and subjected to the electromagnetic field of the electrodes 114 and 115. In some embodiments, a heater 760 may improve evaporation of the precursor 722, therefore increasing availability of the precursor at the electrodes 114 and 115. In some embodiments, the precursor 722 may be a solid or gel substance that evaporates faster when the heater 760 operates.

After flowing through the air conduit 714, the cold plasma 118 may be exhausted from the cold plasma treatment device 100 by an air mover 730 (e.g., an air fan, an air blower, an ionic wind blower, etc.). The cold plasma treatment device 100 may include a plasma barrier 730. In some embodiments, the plasma barrier 710 may be perforated to, for example limit and/or regulate the flow of the cold plasma 118 toward the biological surface 210. The plasma barrier may be a vent barred by one or more grills, a wire mesh screen, a patterned perforated screen, etc. The perforation size of the plasma barrier 710 may be selected based on the target flow rates of the cold plasma 118. In different embodiments, the plasma barrier 710 may be made of different materials, for example metals, ceramics or plastics.

In some applications, generating the cold plasma away from the biological surface 210 (e.g., away from the skin of the user) may be advantageous in comparison to generating the cold plasma proximately to the biological surface 210. When the cold plasma is generated away from the biological surface 210, the concentration, temperature, pressure, etc., of the plasma does not have to be as tightly controlled as when the plasma is generated directly at the biological surface 210. For example, whereas the temperature of the air that carries the cold plasma toward the biological surface 210 has to be within a relatively narrow range (to avoid discomfort to the user); the available range of temperatures for the incoming air is wider when the plasma is generated away from the biological surface.

In some embodiments, control of the plasma species concentration is improved by selecting the precursors 722 in the cartridge 725. Furthermore, the geometry, and the thermofluid parameters of the cold plasma treatment system 100 may also control the concentration of the plasma species. For example, the concentration of the plasma species and the temperature of the air will generally decrease with time elapsed from the creation of the plasma species. Therefore, a length L3 of the air conduit 714 scales inversely with the concentration of the plasma species, because the length L3 delays arrival of the plasma species at the biological surface, at least in the first approximation. Furthermore, the concentration of the plasma species may also scale inversely with a length L2 of the space above the precursor (above space L1 of the cartridge). Additionally, the concentration of the plasma species may also be controlled through a speed of the air mover 730, and/or a voltage of the AC source 112. In operation, the controller 142 may adjust the parameters for generating the cold plasma (e.g., voltage of the AC source 112, speed of the air mover 730, temperature of the heater 760).

Figure 21:
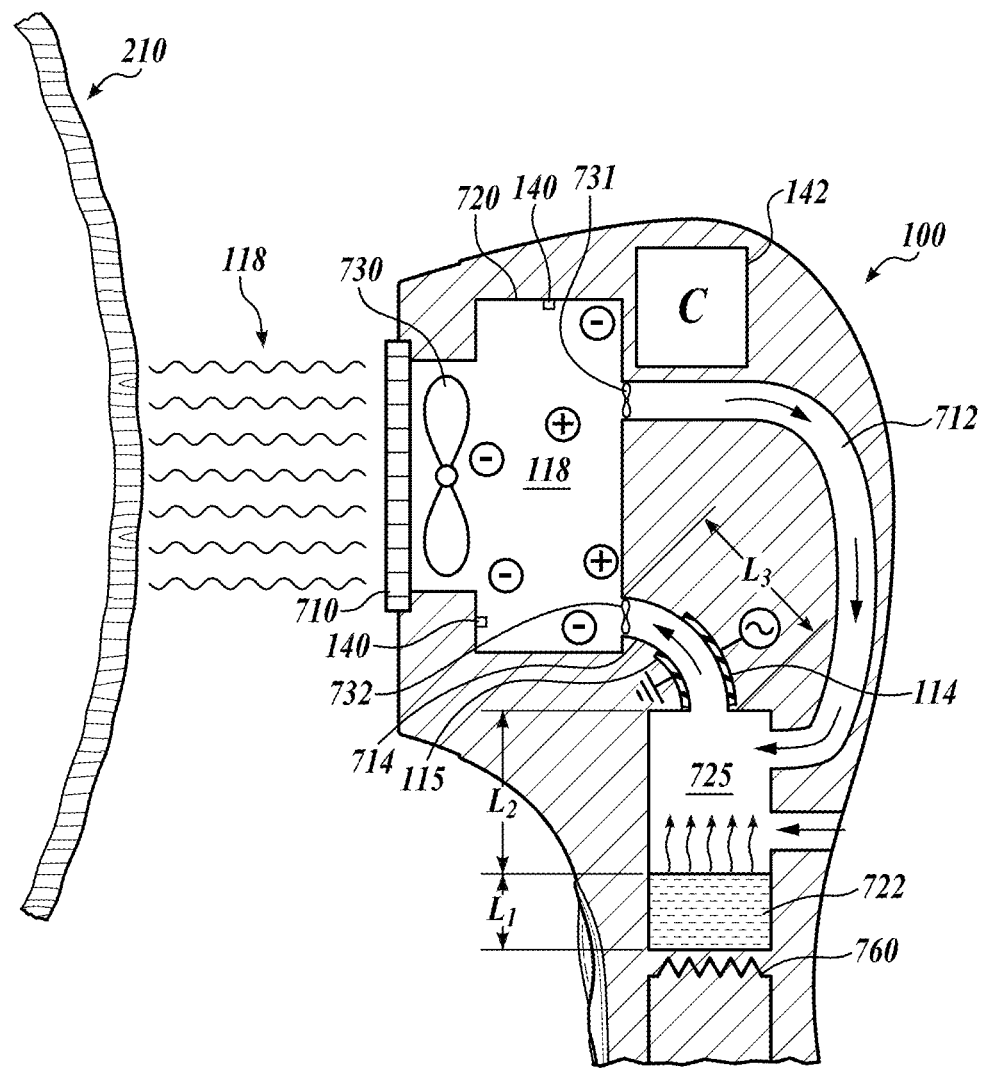
FIG. 21 is a schematic diagram of a cold plasma treatment system in accordance with the present disclosure.

FIG. 21 is a schematic diagram of the cold plasma treatment system 100 in accordance with the present disclosure. The illustrated cold plasma treatment system 100 includes a reservoir 720 for temporary storage of the cold plasma 118 before exhausting the cold plasma toward the biological surface 210. By storing the cold plasma in the reservoir 720, the time elapsed from generating the cold plasma to exhausting the cold plasma from the system 100 may be better controlled. As a result, in at least some embodiments, the concentration and/or temperature of the cold plasma species may also be better controlled. In some embodiments, the reservoir 720 may have one or more sensors that sense the state of the cold plasma. For example, the sensors 140 may sense concentration of the cold plasma, temperature, pressure, composition, etc.

In the illustrated embodiment, an additional air conduit 712 connects the reservoir 720 with the air conduit 714, therefore providing a return path for the plasma species back toward the electrodes 114 and 115. In some embodiments, the air conduit 712 provides for better control of the concentration and/or temperature of the cold plasma in the reservoir 720. For example, if the sensors 140 detect that the concentration of the plasma species in the reservoir 720 is insufficient, the controller 142 may increase the rotational speed of the air mover 731, therefore routing more air and plasma back to the electrodes 114 and 115 to generate additional plasma species in the stream of air entering reservoir 720. Furthermore, the speed of the air mover 732 may be adjusted to control the flow of air and plasma to the reservoir 720. In some embodiments, the speed of the air mover 730 may be adjusted to vary the outflow of the plasma species out of the reservoir 720. The controller 142 may additionally control the heater 760 to control the temperature and concentration of the gaseous precursor 722 at the inlet to the air conduit 714. In some embodiments, these additional control mechanisms improve the control of the cold plasma concentration, temperature, types of the cold plasma species (e.g., ROS-dominated, RNS-dominated), pressure in the reservoir 720, and other parameters of the cold plasma.

Figure 22A:
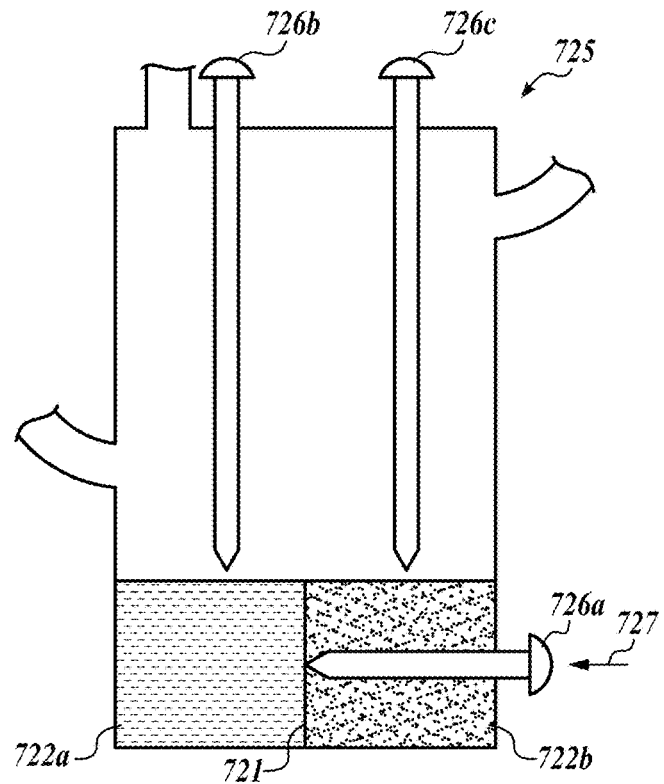
FIGS. 22A and 22B are schematic diagrams of a precursor cartridge in accordance with the present disclosure.
Figure 22B:
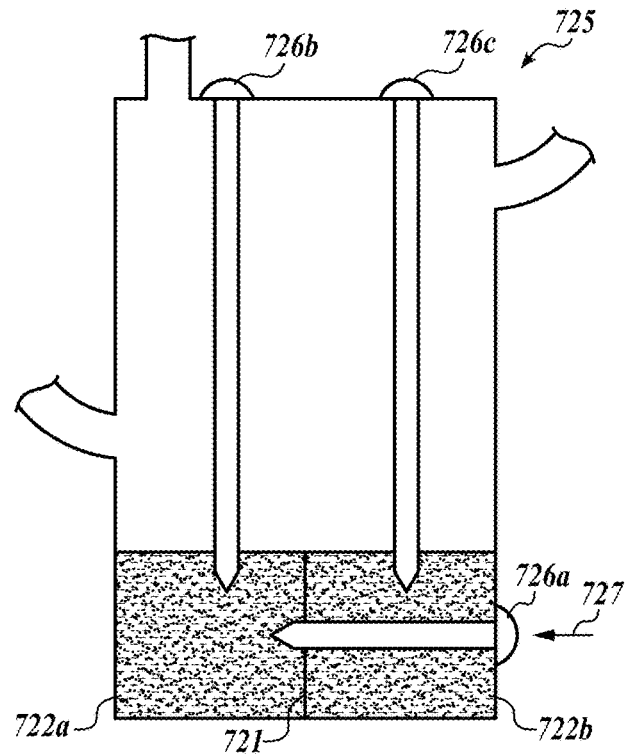

FIGS. 22A and 22B are schematic diagrams of a precursor cartridge in accordance with the present disclosure. In some embodiments, the precursor 722 may include two precursor components 722a and 722b. In different embodiments, the precursor 722 may have other numbers of the precursor components, for example, three or more components. In some embodiments, the precursor components are separated by a cartridge barrier 721. When separated from each other, the precursor components may remain relatively stable, therefore possessing relatively long shelf life. Conversely, mixing the precursor components may initiate a relatively short period during which the mixture generates the precursors for the cold plasma. In some embodiments, the mixture may generate the gaseous precursors during a period of several minutes (e.g., 1-10 minutes), such that this period of time generally coincides with the predicted duration of the skin treatment.

FIGS. 22A and 22B illustrate the components 722a and 722b in their pre-mixed and mixed state, respectively. In the pre-mixed state shown in FIG. 22A, the two precursor components 722a and 722b are separated by the cartridge barrier 721. In some embodiments, the cartridge barrier 721 may be a relatively thin diaphragm that can be punctured. In other embodiments, the cartridge barrier 721 may be removable by other means, for example, by applying heat or by electromechanical removal.

FIG. 22A illustrates the cartridge 725 before its insertion into the cold plasma treatment device 100. Before the insertion, activators 726a-726c may be in their retracted state away from the cartridge barrier 721.

FIG. 22B illustrates the cartridge 725 after its insertion into the cold plasma treatment system 100. In some embodiments, the insertion of the cartridge 725 pushes the activators 726a-726c (e.g., pins) toward the cartridge barrier 721, thus breaching the cartridge barrier, and initiating mixing of the components 722a and 722b. As explained above, when mixed, the components 722a and 722b generate the precursor 722. In some embodiments, the activators 726a-726c may be pushed by the user (direction 727), may be configured to be pushed by the act of inserting the cartridge 725, or may be moved electromechanically or with other suitable means.

Figure 23:
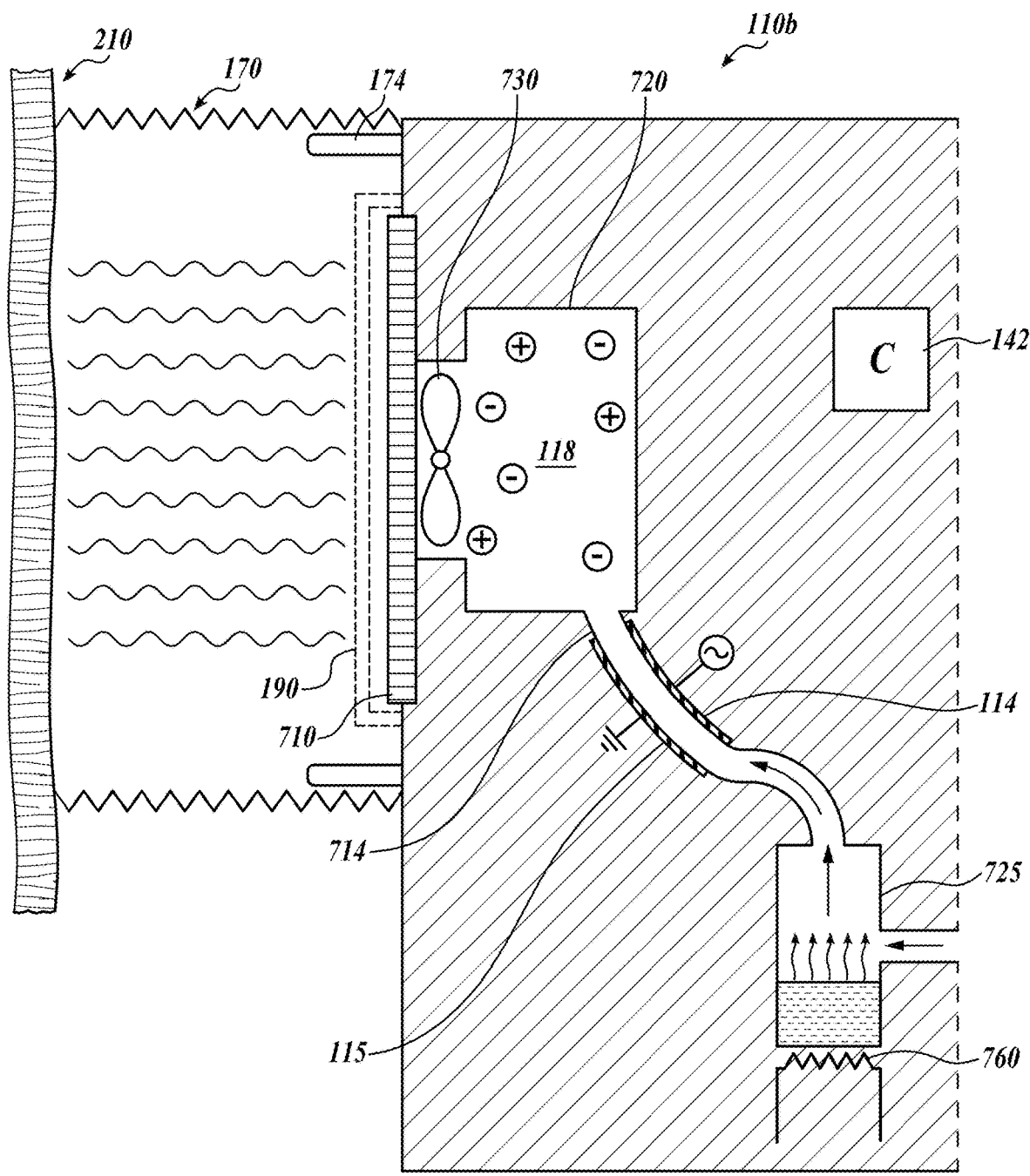
FIG. 23 is a schematic diagram of a cold plasma treatment system in accordance with the present disclosure.

FIG. 23 is a schematic diagram of the cold plasma treatment system 100 in accordance with the present disclosure. In some embodiments, the cold plasma treatment system 100 includes a flexible skirt 170. The flexible skirt 170 may be made from corrugated plastic or soft rubber, and attached around the plasma barrier 710 to contain the cold plasma 118 proximate to the biological surface 210. For example, the flexible skirt 170 may be impermeable to gases and, when compressed, may create a contained environment for the plasma 118. In some embodiments, the flexible skirt 170 is compressed by contacting the biological surface 210.

In some embodiments, the cold plasma treatment system 100 includes a rigid spacer 174, restricting the compression of the flexible skirt 170, thereby defining a minimum spacing between the plasma barrier 710 and the biological surface 210. The rigid spacer 174 may be enclosed by the flexible skirt 170 or may be external to it, and may be removable. In some embodiments, the rigid spacer 174 includes a conductive material including but not limited to a metal. In some embodiments, the rigid spacer 174 includes a conductive material that is biased at a voltage greater than or equal to zero. Without being bound to theory, it is believed that the rigid spacer 174 thus biased may electromagnetically shape the space for plasma containment between the plasma barrier 710 and the biological surface 210, thus controlling the contact between the cold plasma and the biological surface.

In one embodiment, the cold plasma treatment system 100 includes a filter 190 for filtering the plasma 118. The filter 190 may be placed between the plasma barrier 710 and the biological surface 210. In some embodiments, the filter 190 is a charged particle filter placed between the plasma 118 and the biological surface 210 that attracts and neutralizes charged particles present in the plasma 118. In some embodiments, the charged particle filter includes one or more conductive elements, individually biased at a nonzero voltage. Non-limiting examples of a conductive element include a metal screen, a metal probe, a metal ring, etc., placed near or around the plasma barrier 710. In some embodiments, the charged particle filter selectively filters out positive ions by having a negative polarity, therefore neutralizing the positive ions that approach the surface of the filter 190. In some embodiments, the charged particle filter filters out all charged particles by combining multiple conductive elements, e.g., at least one conductive element having a negative polarity and at least one conductive element having a positive polarity.

Cold Plasma Activated Formulations for Application to Skin

Figure 24:
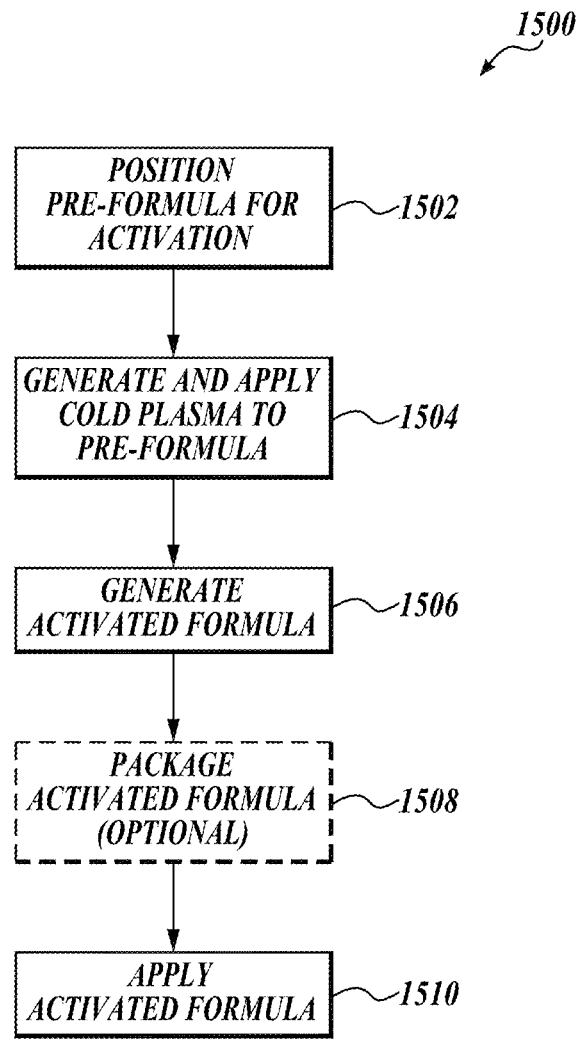
FIG. 24 depicts a flow diagram of an example process for activation of a formulation using cold plasma, in which the cold plasma-activated formulation is to be applied to a biological surface (e.g., skin, nails, hair, etc.) in accordance with the present disclosure.
Figure 25:
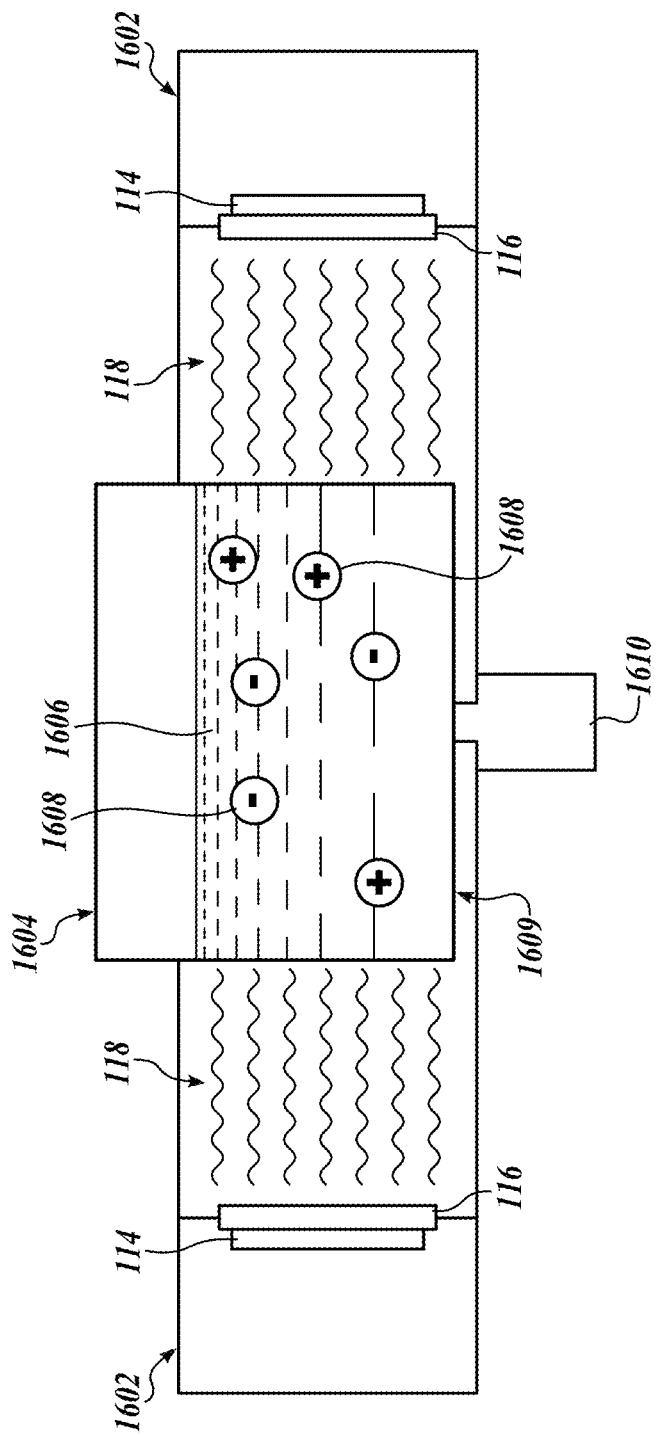
FIG. 25 depicts a cross-sectional view of an example system configured to perform at least a portion of the process of FIG. 15 in accordance with the present disclosure.

FIG. 24 depicts a flow diagram of an example process 1500 for activation of a formulation using cold plasma, in which the cold plasma-activated formulation is to be applied to a biological surface (e.g., skin, nails, hair, etc.) in accordance with some embodiments of the present disclosure. FIG. 25 depicts a cross-sectional view of an example system 1600 configured to perform at least a portion of the process 1500 in accordance with some embodiments of the present disclosure. FIGS. 24-25 are described below in conjunction with each other.

At block 1502 of FIG. 24, a formula or formulation to be activated by (or otherwise exposed to) cold plasma—also referred to as a pre-formula, pre-formulation, pre-treatment formulation, first formula, first formulation, initial formula, or initial formulation—is positioned within system 1600 to undergo cold plasma activation. In some embodiments, pre-formula 1606 is provided within a container 1604, and system 1600 includes a receptacle (e.g., well, indentation, cavity, container holder, etc.) configured to receive, hold, and position the container 1604 for exposure to cold plasma 118 discharged by a plasma generation device 1602 included in system 1600. Container 1604 may comprise any of a variety of materials conducive for generation of cold plasma 118 and/or transmission of cold plasma 118 to the pre-formula 1606. For instance, without limitation, container 1604 may comprise a glass material, a ceramic material, or the like.

In some embodiments, pre-formula 1606 comprises an aqueous solution (e.g., liquid, serum, oil, gel, cream, lotion, media, medium, carrier, etc.) configured to be a medium or carrier to absorb one or more of the plasma species or compounds of the cold plasma 118. Pre-formula 1606 can also include one or more compounds that stabilize and/or increase the lifetime of various short lived plasma species absorbed into it. Alternatively or in addition to, pre-formula 1606 comprises an aqueous solution that includes one or more pre-cursor compounds to be modified or activated by the presence of one or more of the plasma species or compounds of the cold plasma 118. Pre-formula 1606 can also include one or more other compounds not associated with cold plasma, such as compound(s) that may be shelf stable and need not be generated "fresh" using plasma (e.g., antioxidants, moisturizers, exfoliants, etc.). Without limitation, at least a portion of pre-formula 1606 may be similar to formulation 410.

Pre-formula 1606 thus comprises a formulation or media capable of retaining at least some of the relatively longer lived plasma species, continue to exhibit some plasma activity if applied to, for example, on biological surface 210 in the absence of plasma, and/or (chemically) modify compound(s) already present in the formulation in the presence of plasma. The effect of plasma on the pre-formula 1606 may disappear over time, such as over the course of hours, days, or weeks, which makes the plasma activated formulation difficult to make and provide to users as a shelf stable product. For this reason, plasma activated formulations can be generated "fresh" prior to topical application, as described herein.

Next, at block 1504, system 1600 is configured to generate and apply cold plasma 118 to the pre-formula 1606. Depending on the lifespan of the plasma activated formulation relative to when the plasma activated formulation is to be topically applied, the user may actuate system 1600 to generate cold plasma 118 on a timely basis (or block 1504 may automatically be performed upon placement of the container 1604 within system 1600 at block 1502). For example, if a plasma activated formulation will be stable or remain active for a week, then block 1504 may be performed within a week prior to use of the activated formulation.

In some embodiments, system 1600 may comprise a system that makes it difficult or impossible for use on biological tissue directly (e.g., prevents plasma discharge directly on biological surface 210). System 1600 can instead be optimized for application of plasma to pre-formulas without electrical, temperature, dosage, and/or other safety constraints associated with plasma application on biological tissue. Plasma 118 can have a higher dosage or concentration for application to pre-formula 1606 than if applied to biological surface 210.

Referring to FIG. 25, plasma generation device 1602 included in system 1600 is configured to discharge cold plasma 118 to one or more sides of the container 1604. Plasma generation device 1602 comprises one or more continuous or discrete devices. In some embodiments, plasma generation device 1602 includes an electrode 114 and a dielectric barrier 116. Dielectric barrier 116 is disposed between electrode 114 and container 1604. Dielectric barrier 116 and electrode 114, comprising a cold plasma generator, are configured to discharge cold plasma 118 in a direction generally toward container 1604.

Plasma generation device 1602 may also include a cover (not shown) disposed between the dielectric barrier 116 and container 1604. The cover may comprise plastic, glass, quartz, or the like, and be configured to block certain plasma generated species from reaching the pre-formula 1606. For example, plasma 118 may emit ultraviolet photons under certain conditions and it may be desirable to block the transmission of such ultraviolet photons using the cover. In an embodiment, the cover may be optional if undesirable plasma generated species are not generated, only a minimal amount are generated, or if they do not adversely affect the pre-formula 1606.

In some embodiments, at least some of the plasma species or compounds 1608 (e.g., reactive species, charged species, relatively longer lived species, relatively short lived species, etc.) included in the cold plasma 118 are transmitted to be present within the pre-formula 1606.

Plasma species/compounds 1608 (or plasma 118 overall) cause the pre-formula 1606 to be converted to an activated formula 1609 (also referred to as an activated formulation, second formulation, topical formulation, final formulation, or the like), at block 1506. The activated formula 1609 comprises the pre-formula 1606 with the addition of plasma species or compounds 1608, pre-formula 1606 with one or more of compounds within pre-formula 1606 changed based on exposure to cold plasma 118, a formula different from pre-formula 1606, and/or the like. In some embodiments, activated formula 1609 includes one or more reactive or active compounds or ingredients not present in pre-formula 1606. The one or more reactive or active compounds/ingredients may be associated with exposure to plasma 118. The one or more reactive or active compounds/ingredients may provide short term benefits, long term benefits, cause biological surface 210 to become biologically reactive or active (e.g., cause skin peeling, reduce melanin production, promote collagen production, etc.), and/or be efficacious to biological surface 210 (e.g., increase hydration level, etc.). The activated formula 1609 may comprise a non-shelf stable product.

Because a higher dose of plasma, plasma exposure for a longer period of time, plasma of different species/compounds, and/or any particular plasma configuration may be provided to the pre-formula 1606 at block 1504, in comparison to plasma that may be safely discharged to a biological surface 210, a higher concentration of plasma species in general and/or particular plasma species of interest can be provided to the biological surface 210 via topical application of activated formula 1609 than may be possible via direct application of plasma to the biological surface 210. In an embodiment, plasma 118 may be applied to a given pre-formula 1606 for several hours or days, as desired, even though such a time period may be harmful or impractical for application to the biological surface 210.

Figure 26:
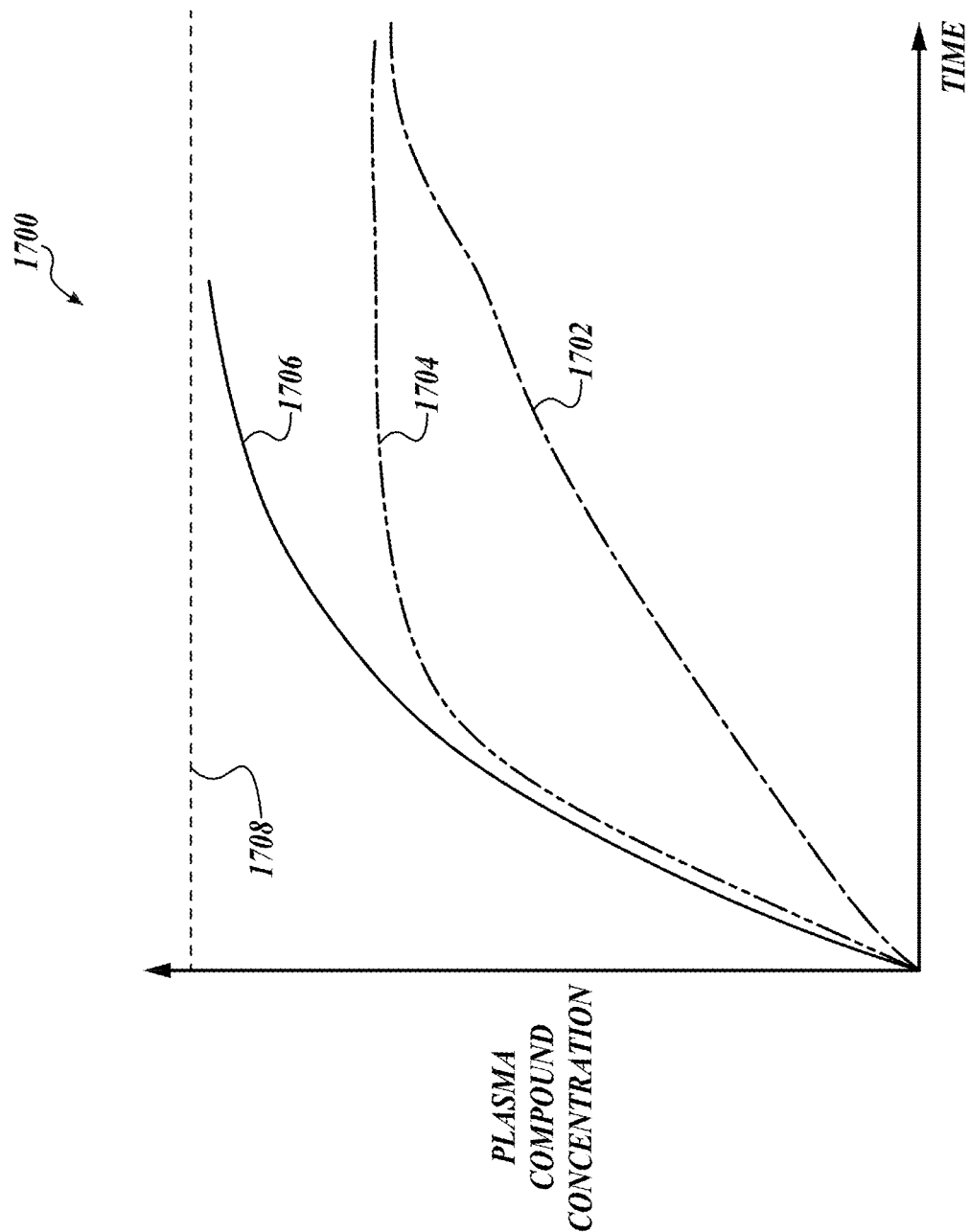
FIG. 26 depicts an example graph showing various example plots of different plasma species/compound concentration levels as a function of time in accordance with the present disclosure.

FIG. 26 depicts an example graph 1700 showing various example plots of different plasma species/compound concentration levels as a function of time in accordance with some embodiments of the present disclosure. Plasma species/compound concentration levels at the biological surface 210 as a function of time, in which plasma is discharged directly to the biological surface 210, is represented by a plot 1702. Plasma species/compound concentration levels at a pre-formula (e.g., pre-formula 1606) as a function of time, in which plasma at a first dosage level is discharged directly to the pre-formula, is represented by a plot 1704. Plasma species/compound concentration levels at a pre-formula (e.g., pre-formula 1606) as a function of time, in which plasma at a second dosage level is discharged directly to the pre-formula, is represented by a plot 1706. The second dosage level may be a higher dosage than the first dosage level.

Higher levels of plasma species/compound concentration may be injected into pre-formulas in a shorter period of time (see plots 1704, 1706) than may be possible discharged directly to a biological surface 210 (see plot 1702). Plot 1706 shows that a plasma species/compound concentration level closer to a maximum possible concentration level, as indicated by line 1708, may be achieved via use of a pre-formula than if discharged directly to the biological surface 210 (see plot 1702).

Returning to FIG. 20, at block 1508, activated formula 1609 may be transferred from container 1604 to a different container 1610 suitable for dispensing activated formula 1609 for topical application. Container 1610 can attach to an outlet valve included in system 1600 proximate to the container 1604 (e.g., bottom of container 1604). Container 1604 may comprise a container suitable to transport/maintain (e.g., air tight container) pre-formula 1606 and activate it via cold plasma 118 but which is not suitable to contain or dispense the activated formula 1609. For example, container 1604 may not be ergonomically shaped for a user to use some of the activated formula 1609, preserve activated formula 1609 over a plurality of dispensing of the activated formula 1609, and/or the like. Only a portion of the activated formula 1609 may be transferred to container 1610 at any given time. Container 1610 may comprise, for instance, a (disposable) single dosing dispenser of the activated formula 1609, with the remainder of the activated formula 1609 remaining in the container 1604 to preserve its active state and prevent contamination or deterioration. Or container 1610 may be configured to receive all of the activated formula 1609 and include a cap or other sealing mechanisms associated with repeat dispensing of the activated formula 1609.

In embodiments where container 1604 is suitable to retain the activated formula 1609 and provide the requisite dispensing and/or contamination prevention requirements, transference to container 1610 may be omitted and block 1508 is optional.

Lastly, at block 1510, the activated formula 1609 (in the suitable container 1604 or 1610) can be applied to the biological surface 210. In this manner, a relatively short lived formulation can be formulated on-demand on an as needed basis that may not otherwise be possible to provide to a user as an off-the-shelf product. Such on-demand formulation may include a (higher) level of active or reactive compound(s) that are realized via exposure to particularly configured plasma. Such on-demand formulation may also serve as a carrier to provide a higher concentration and/or certain plasma species to the biological surface 210 than otherwise would be possible via a direct discharge of plasma to the biological surface 210.

Figure 27:
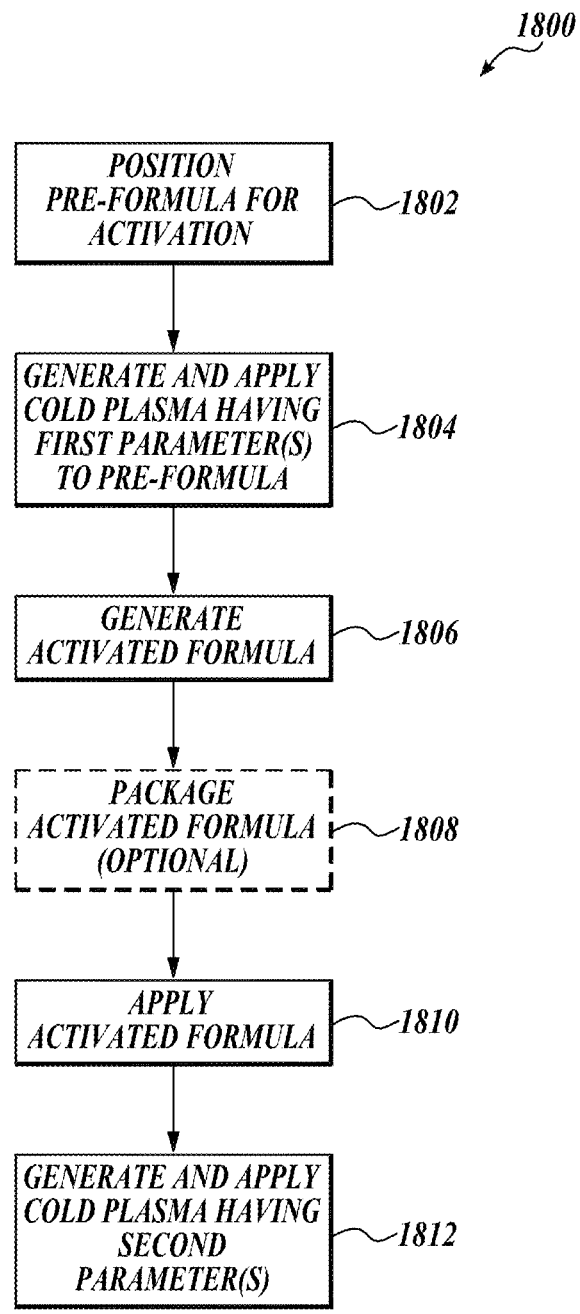
FIG. 27 depicts a flow diagram of an example process that may comprise an alternative to the process of FIG. 15
Figure 28A:
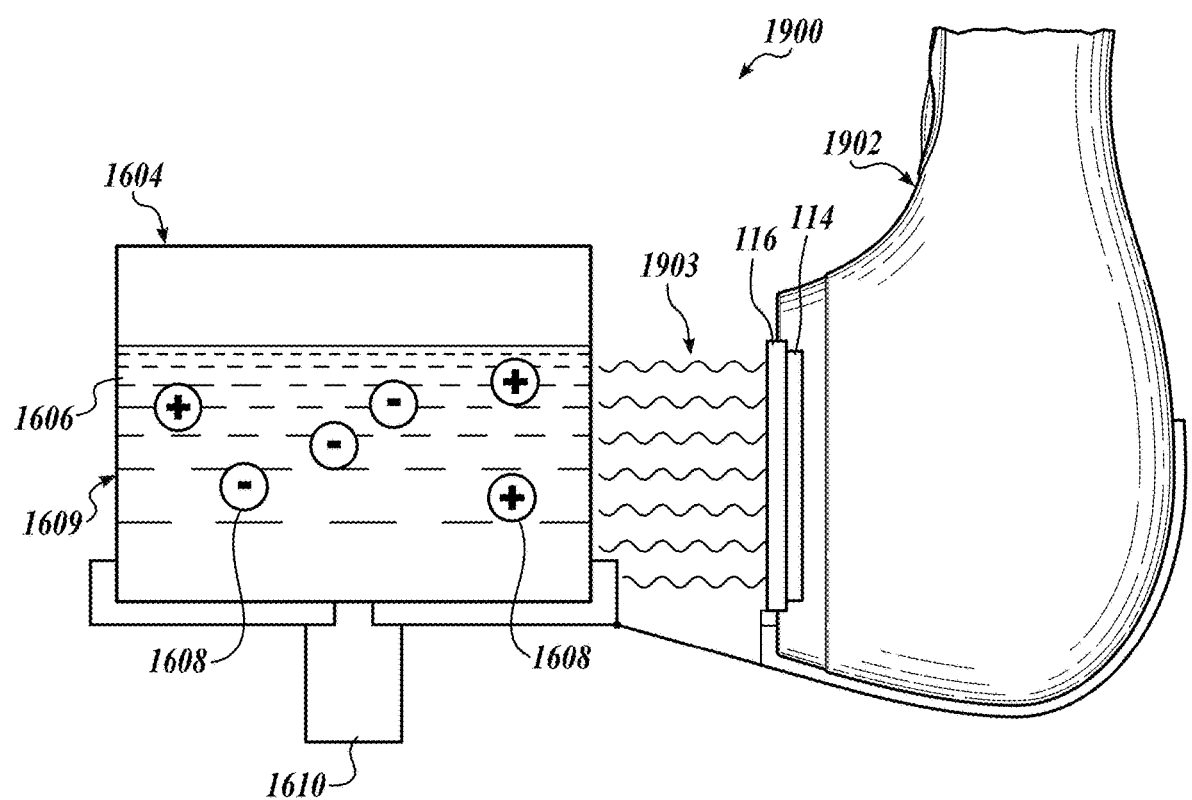
FIGS. 28A-28B depict views of an example system configured to perform at least a portion of the process of FIG. 18 in accordance with the present disclosure.
Figure 28B:
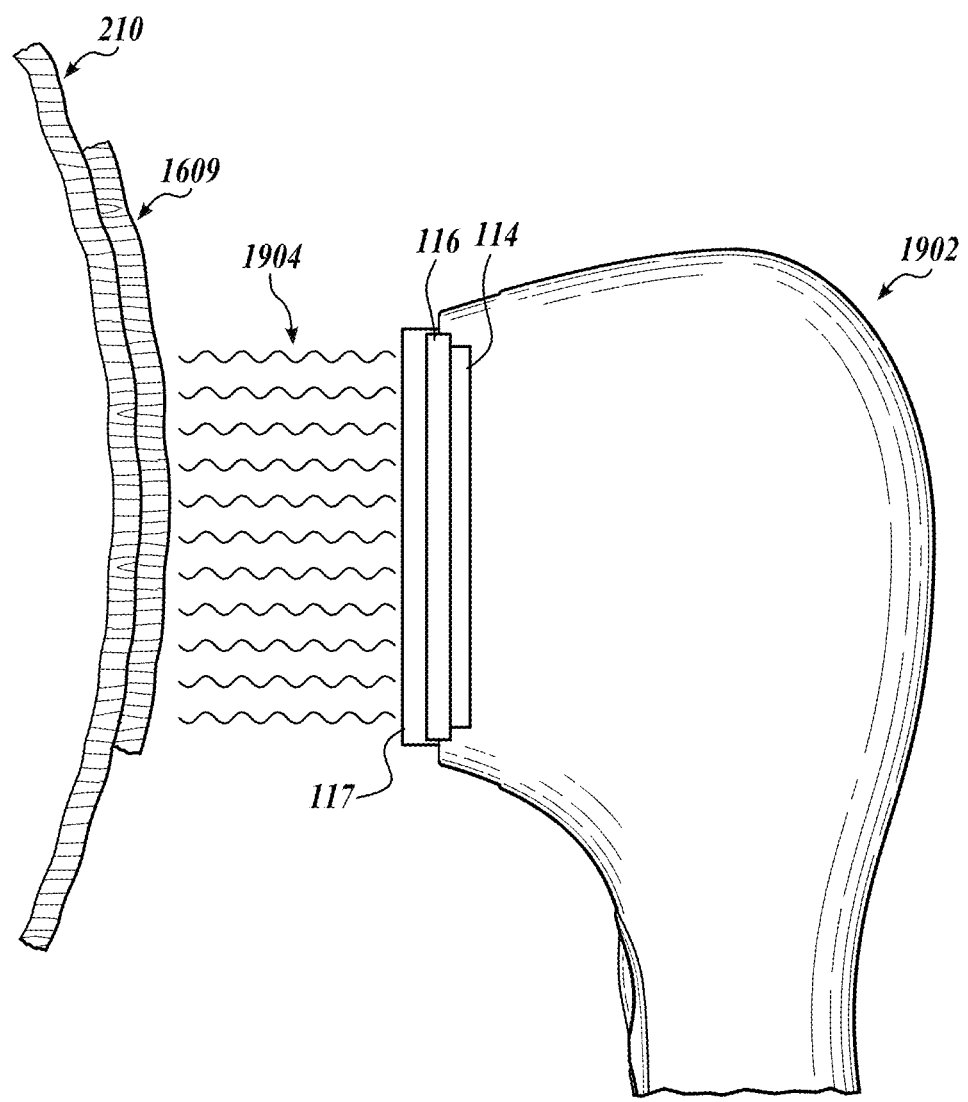

In an embodiment, plasma may be provided to the biological surface 210 both indirectly via the activated formula 1609 and directly via exposure to cold plasma. FIG. 27 depicts a flow diagram of an example process 1800 that may comprise an alternative to process 1500 of FIG. 20. FIGS. 28A-28B depict views of an example system 1900 configured to perform at least a portion of the process 1800 in accordance with some embodiments of the present disclosure.

In some embodiments, blocks 1802-1810 of process 1800 are similar to respective blocks 1502-1510 of process 1500, except blocks 1802-1810 may be performed in association with system 1900. Moreover, the parameters associated with cold plasma 1903 generated and applied to the pre-formula 1606 (also referred to as the first parameters) in system 1900, at block 1804, comprises one or more parameters that may be the same or different from parameters associated with cold plasma 118 discharged to the pre-formula 1606 in system 1600. One or more parameters of cold plasma 1903 may differ from those of cold plasma 118 because, among other things, cold plasma 1904 is to be sequentially provided to the biological surface 210 after the formulation activated using cold plasma 1903 is topically applied to the biological surface 210.

System 1900 may comprise a system similar to system 1600 except a plasma generation device 1902 included in the system 1900 is configured to be selectively removable from the system 1900 and can also be used alone as a plasma treatment device proximate the biological surface 210 (see FIG. 19B).

After the activated formula 1609 has been applied to the biological surface 210 (see FIG. 19B), at block 1810, plasma generation device 1902 can be detached from system 1900 and configured to provide cold plasma 1904 to the region of the biological surface 210 overlaid with topically applied activated formula 1609, at block 1812. In FIG. 19B, an optional cover 117 is also illustrated.

In some embodiments, the plasma generation device 1902 is operable in a plurality of different operational states. Plasma generation device 1902 may be configured to operate in a first operational state when located in the system 1900 to activate the pre-formula 1606. The first operational state may comprise generating cold plasma 1903 having first parameter(s). When the plasma generation device 1902 is removed from its cradle or cavity included in system 1900, and thus able to discharge plasma to biological tissue, device 1902 may operate in a second operational state that generates cold plasma 1904 having second parameter(s). The first and second operational states and respective first and second parameters may differ from each other. The first parameters associated with cold plasma 1903 may be optimized for activation of the pre-formula 1606 while the second parameters associated with cold plasma 1904 may be optimized for safely discharging plasma to the biological surface 210 and/or treatment of the biological surface 210 in conjunction with activated formula 1609. As an example, dosage level of cold plasma 1903 may be higher than the dosage level of cold plasma 1904. As another example, dosage duration of cold plasma 1903 may be a longer period of time than the time period for cold plasma 1904.

In an embodiment, system 1600 may be used to generate the activated formula 1609 and plasma generation device 1902 may be used for applying plasma directly to biological surface 210. In other embodiments, plasma generation device 1602 or 1902 need not be seated within system 1600 or 1900, respectively, in order to convert pre-formula 1606 to activated formula 1609. Container 1604 containing pre-formula 1606 may be located on a table and plasma generation device 1602 or 1902 alone may be positioned proximate to container 1604 and actuated to generate cold plasma 118 or 1903, respectively, to generate activated formula 1609. In still other embodiments, plasma discharge directly to biological surface 210 may occur prior to application of a plasma activated formula to the biological surface 210 (e.g., block 1812 may be performed before block 1810). In yet still other embodiments, one or more of blocks 1802-1810 may be performed concurrently with block 1812.

A variety of pre-formulas can be activated by system 1600 or 1900 in accordance with some embodiments of the present disclosure. Different pre-formulas may be formulated to address different skin concerns or treatment benefits, for instance. A first pre-formula may comprise a formation that is a carrier for one or more plasma species; a second pre-formula may comprise a formation that is a pre-cursor that is to chemically activate in the presence of cold plasma; a third pre-formula may comprise a formation that carries one or more plasma species, chemically activates, and includes one or more beneficial compounds unaffected by the presence of cold plasma; and/or the like.

In an embodiment, plasma generation device 1602 or 1902 may comprise devices that generate plasma using mechanisms other than dielectric barrier discharge. A variety of other plasma generation mechanisms can be implemented in system 1600 or 1900 such as, but not limited to, plasma jets.

Electromagnetic Field Confinement of Cold Plasma Applied to Skin

Figure 29:
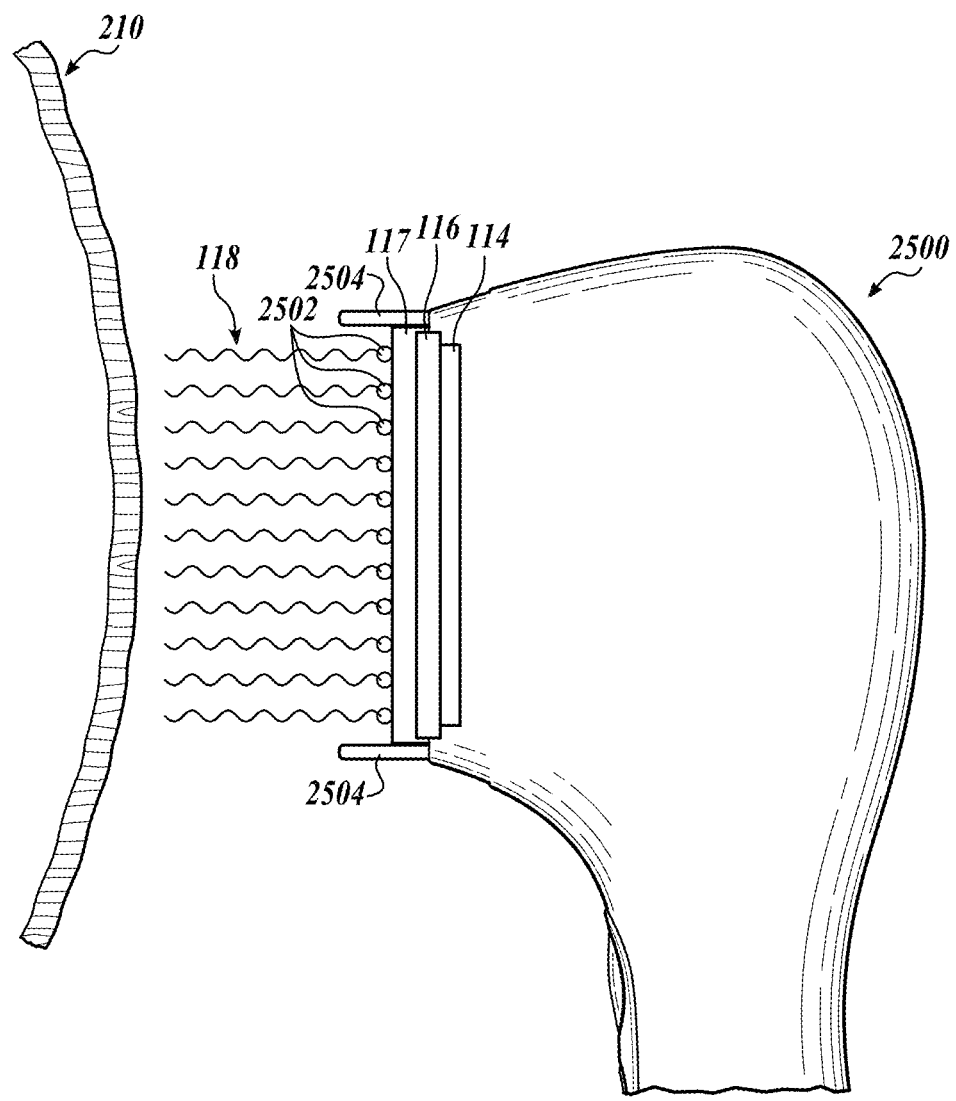
FIG. 29 depicts a side view of a schematic diagram of a cold plasma treatment system in accordance with the present disclosure.

FIG. 29 depicts a side view of a schematic diagram of a cold plasma treatment system in accordance with some embodiments of the present disclosure. In some embodiments, a plasma treatment device 2500 includes an electrode 114, a dielectric barrier 116, a cover 117, a plurality of electromagnetic field generator units 2502, and one or more spacers 2504. Dielectric barrier 116 is disposed between electrode 114 and cover 117. Cover 117 is disposed between the plurality of electromagnetic field generator units 2502 and the dielectric barrier 116.

In an embodiment, a plurality of electromagnetic field generator units 2502 comprises an array of electromagnetic field generator units. In an embodiment, an electromagnetic field generator units' array comprises a plurality of electromagnetic field generator units arranged in regular or irregular geometric patterns. In an embodiment, the electromagnetic field generator units are distributed over a two- or three-dimensional space and/or a two- or three-dimensional surface element. In an embodiment, the electromagnetic field generator units are distributed over the surface of a regular or irregular geometric structure.

In an embodiment, each electromagnetic field generator unit of the plurality of electromagnetic field generator units 2502 is located coplanar to each other, in which the plane associated with the plurality of electromagnetic field generator units 2502 is parallel to a major plane associated with one or more of the electrode 114, dielectric barrier 116, and cover 117. In an embodiment, one or more of the electromagnetic field generator units of the plurality of electromagnetic field generator units 2502 can be distributed non-coplanar with each other.

One or more of spacers 2504 is located at the periphery of the plasma treatment device 2500. In an embodiment, one or more of the cover 117 and the plurality of electromagnetic field generator units 2502 is disposed between the spacers 2504, along a plane substantially parallel to a major plane associated with the electrode 114, dielectric barrier 116, and/or cover 117.

Dielectric barrier 116 and electrode 114, comprising a cold plasma generator, are configured to discharge cold plasma 118 in a direction generally toward biological surface 210 (e.g., skin). Cover 117 is disposed on or over the dielectric barrier 116. The cover 117 may comprise plastic, glass, quartz, or the like, and be configured to block certain plasma generated species from reaching the biological surface 210. For example, plasma 118 may emit ultraviolet photons under certain conditions and it may be desirable to block the transmission of such ultraviolet photons using the cover 117. In an embodiment, cover 117 may be optional if undesirable plasma generated species are not generated or only a minimal amount are generated or if, for instance, the plurality of electromagnetic field generator units 2502 is configured to prevent undesirable plasma generated species from reaching the biological surface 210, as will be described in detail below.

In an embodiment, the plurality of electromagnetic field generator units 2502 is located downstream of the nominal or initial plasma exiting area of the plasma treatment device 2500. In an embodiment, the plurality of electromagnetic field generator units 2502 is configured to form a continuous or non-continuous ring of units encircling the plasma stream exiting the plasma treatment device 2500. In an embodiment, each electromagnetic field generator unit of the plurality of electromagnetic field generator units 2502 is configured to generate a fixed or variable electromagnetic field having particular parameter(s). The electromagnetic field generated by each of the electromagnetic field generator units can be the same or different from each other. As will be discussed below, the plurality of electromagnetic field generator units 2502 is configured to control, confine, modify, steer, and/or otherwise manipulate the plasma nominally outputted by the device 2500 so that the resulting plasma received by the biological surface 210 can differ from the nominally outputted plasma.

In some embodiments, spacers 2504 are configured to define a minimum spacing or separation distance between the device 2500 and the biological surface 210. Spacers 2504 may be continuous or discrete structures (e.g., a flexible skirt, rigid spacers or bars, etc.). Spacers 2504 thus prevent device 2500 from being located too close to the biological surface 210; facilitates easily maintaining a desirable distance between device 2500 and the biological surface 210; reduces getting dirt on or making contact with one or more components of the device 2500 (e.g., the plurality of electromagnetic field generator units 2502); and/or the like. In alternative embodiments, spacers 2504 may be optional.

Figure 33:
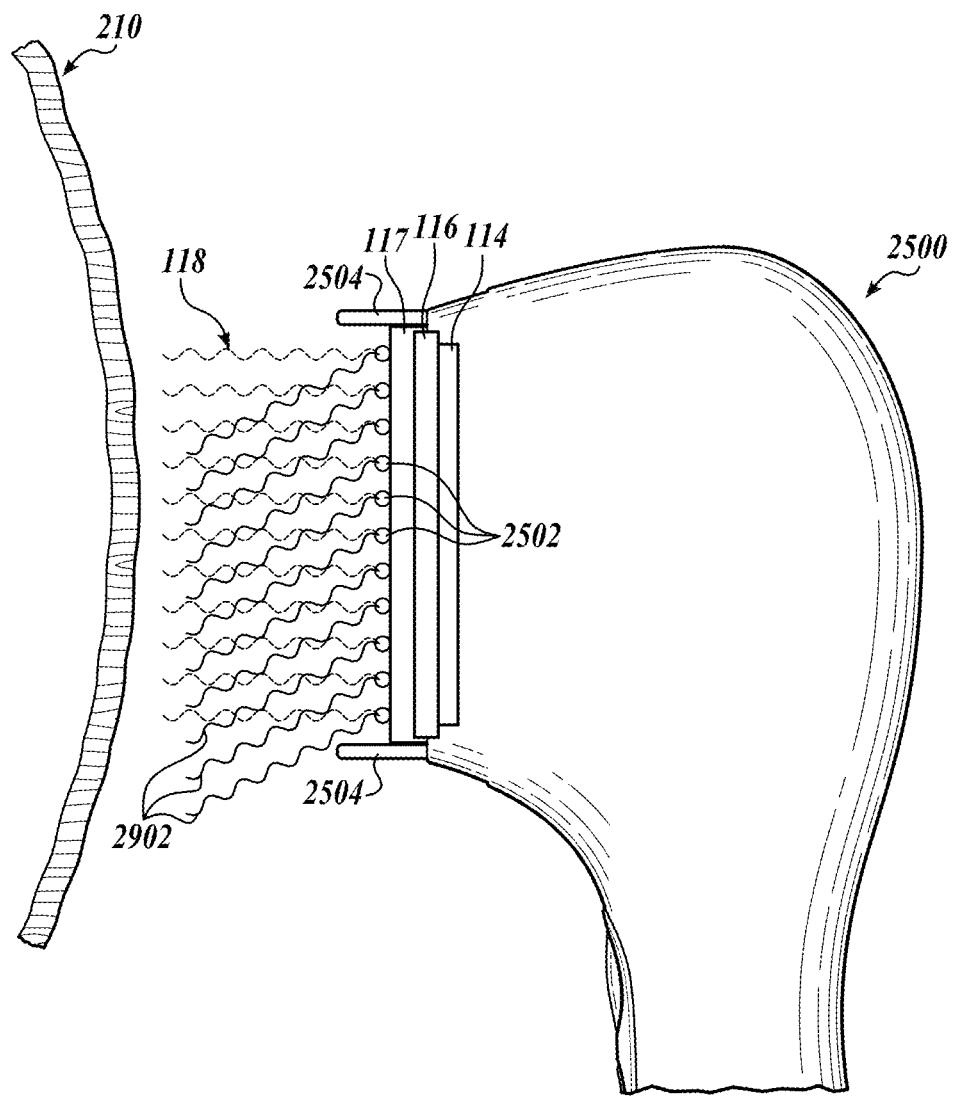
FIG. 33 depicts a side view of a schematic diagram of a cold plasma treatment system showing changed direction of plasma discharge in accordance with the present disclosure.

FIGS. 30-33 depict examples of controlled or confined plasma provided to the biological surface 210 using the plurality of electromagnetic field generator units 2502 in accordance with some embodiments of the present disclosure. FIGS. 30-32 depict simplified cross-sectional views of at least a portion of the device 2500 (e.g., the plurality of electromagnetic field generator units 2502) and the resulting plasma, viewed from the perspective of the biological surface 210 toward the plasma exiting side of the device 2500. FIG. 33 depicts a side view of the device 2500 similar to the view associated with FIG. 29 in accordance with some embodiments of the present disclosure.

As shown in FIG. 30, the plurality of electromagnetic field generator units 2502 may be arranged, without limitation, in a circle concentric with a plasma stream nominally generated by the device 2500 (e.g., nominal or initial plasma 2600). The circle prescribed by the plurality of electromagnetic field generator units 2502 has a diameter that is larger than a diameter of the outer perimeter of the nominal plasma 2600. Although the plurality of electromagnetic field generator units 2502 are shown arranged in a circle and evenly spaced apart from each other, it is contemplated that the arrangement may comprise a square, rectangle, oval, non-geometric shape, only partially surround the nominal plasma 2600, unevenly spaced apart from each other, and/or the like.

In an embodiment, if the plurality of electromagnetic field generator units 2502 is in an inactive state (e.g., off), the resulting/final plasma may comprise the nominal plasma 2600 since the nominal plasma 2600 is not changed by the plurality of electromagnetic field generator units 2502. If each electromagnetic field generator unit of the plurality of electromagnetic field generator units 2502 is operated at the same parameters relative to each other (e.g., at the same intensity), respective electromagnetic fields generated may serve to equally "push" or confine respective proximate portions of the nominal plasma 2600 toward the center, thereby creating a confined plasma 2602 different from the nominal plasma 2600.

Confined plasma 2602 (also referred to as the final or resulting plasma that reaches the biological surface 210 instead of the nominal plasma 2600) thus has a cross-sectional area smaller than that of the nominal plasma 2600. Confined plasma 2602 has a higher concentration of plasma species per cross-sectional unit area (or per unit volume) than the nominal plasma 2600. By operating the plurality of electromagnetic field generator units 2502 in such manner, a virtual volume of the plasma provided to the biological surface 210 can be defined without use of a physical barrier.

In some embodiments, as the electromagnetic field intensity increases, the greater the concentration of plasma species comprising the confined plasma 2602 per cross-sectional unit area or per unit volume.

While confined plasma 2602 has the same (or substantially the same) cross-sectional shape as the nominal plasma 2600 (e.g., both having a circular cross-sectional shape), FIG. 31 shows an example of a confined plasma 2702 having a different cross-sectional shape from that of the nominal plasma 2600. To modify the cross-sectional shape of a plasma volume, particular ones of the electromagnetic field generator units can be operated differently from other electromagnetic field generator units of the plurality of electromagnetic field generator units 2502. For example, without limitation, the electromagnetic field generator units located toward the top and bottom in FIG. 31 (those denoted with cross hatches in FIG. 31) can be configured to generate higher intensity electromagnetic fields relative to electromagnetic fields generated by the electromagnetic field generator units located along the left and right sides in FIG. 31. The higher intensity electromagnetic fields exert a stronger "push" or confinement of the proximate plasma species, resulting in changing the cross-sectional shape of the plasma volume associated with the nominal plasma 2600 from circular to a non-circular (e.g., oval) shape for the confined plasma 2702.

A particular (cross-sectional) shape of the confined plasma 2702 may be more suitable for particular areas of the biological surface 210. For example, the oval shape of the confined plasma 2702 may be suitable for the forehead region of a face.

In some embodiments, two, three, or more subsets of the plurality of electromagnetic field generator units 2502 may operate differently relative to each other to modify the cross-sectional shape of the nominal plasma 2600 as desired. The subset(s) of the plurality of electromagnetic field generator units 2502 may also selectively differentially or similarly operate relative to each other to simultaneously control both the plasma species concentration and cross-sectional shape of the nominal plasma 2600.

FIG. 32 illustrates use of the plurality of electromagnetic field generator units 2502 to effect the distribution of the plasma species within the nominal plasma 2600. In some embodiments, the plasma species included in the nominal plasma 2600 are ionized species and at least some of the plasma species have free charge (e.g., positive or negative charge). The plurality of electromagnetic field generator units 2502 can be configured to modulate the mix of the plasma species in different regions of the plasma stream by inducing electrophoresis in the gas phase. The regions of the plasma stream to be provided to a target (e.g., biological surface 210) can thus contain a high (or higher) concentration of desirable plasma components and low (or lower) concentration of undesirable plasma components. The plurality of electromagnetic field generator units 2502 serve filtering functionality for particular plasma components to be provided to or excluded from the target.

Nominal plasma 2600 may include plasma species or components having a positive charge (e.g., positively charged species 2800) and plasma species or components having a negative charge (e.g., negatively charged species 2802). One or more electromagnetic field generator units of the plurality of electromagnetic field generator units 2502 can be configured to generate a constant, direct current (DC) electric field. In response, the charged species of the nominal plasma 2600 migrate or redistribute to align with the applied electric field. The positively charged species 2800 are "pushed" to a first region 2804 of the plasma stream while the negatively charged species 2802 migrate to a second region 2806, different from the first regions 2804, of the plasma stream, for example. If the positively charged species 2802 comprise the plasma component desirable to be provided to a target, then only the first region 2804 of the plasma stream may be directed to the target and the second region 2806 of the plasma stream may be dispersed, discarded, or otherwise not provided to the target. In this manner, only desirable plasma components or a higher concentration of desirable plasma components may be provided to a target even though the generated cold plasma contains desirable as well as undesirable plasma components.

Depending upon the concentrations of various charged species within the nominal plasma 2600, which of the particular electromagnetic field generator units 2502 are actuated, and/or the desired redistribution of the various charged species to respective regions of the plasma stream, frequency response associated with one or more of the various charged species may also be relevant in the operational parameters of the plurality of electromagnetic field generator units 2502.

Although species 2800 and 2802 are shown in FIG. 32, it is understood that more than two charged species may be included in the nominal plasma 2600. Even among positively charged species 2800, more than one type of positively charged species may exist. For instance, a first positively charged species among the positively charged species 2800 may have a higher positive charge than a second positively charged species of the positively charged species 2800. Likewise, varying strengths of negative charge may exist among the negatively charged species 2802. Accordingly, the plasma species included in the nominal plasma 2600 may be sorted and grouped into two, three, or more regions of the plasma stream.

FIG. 33 shows the plurality of electromagnetic field generator units 2502 configured to steer or bend the discharge direction of the nominal plasma stream (e.g., plasma 118) into a plasma stream oriented at a different angle relative to the exiting plane of the device 2500 (e.g., plasma 2902). This has the effect of changing a target region of the biological surface 210 to which plasma may be actually provided by the device 2500 from the target region associated with plasma 118.

In this manner, plasma nominally or initially generated by device 2500 may be changed in one or more ways in accordance with dynamic operation of the plurality of electromagnetic field generator units 2502. Depending upon the characteristics of the electromagnetic fields generated by select ones of the plurality of electromagnetic field generator units 2502, electromagnetic fields can be used to control, confine, steer, filter, redistribute, reshape, and/or otherwise change the nominally/initially generated plasma. The plasma that actually impinges on the biological surface 210 from the device 2500 may thus differ from the plasma nominally/initially generated by device 2500. Without limitation, the concentration or density of the plasma components within a cross-sectional unit area can be increased from that of the nominally/initially generated plasma, the cross-sectional shape of the plasma stream can be changed from that of the nominally/initially generated plasma, the composition or distribution of plasma components within the plasma stream can be selectively controlled, and/or the target region on the biological surface 210 may be changed without moving the device 2500 relative to its current location.

Figure 34:
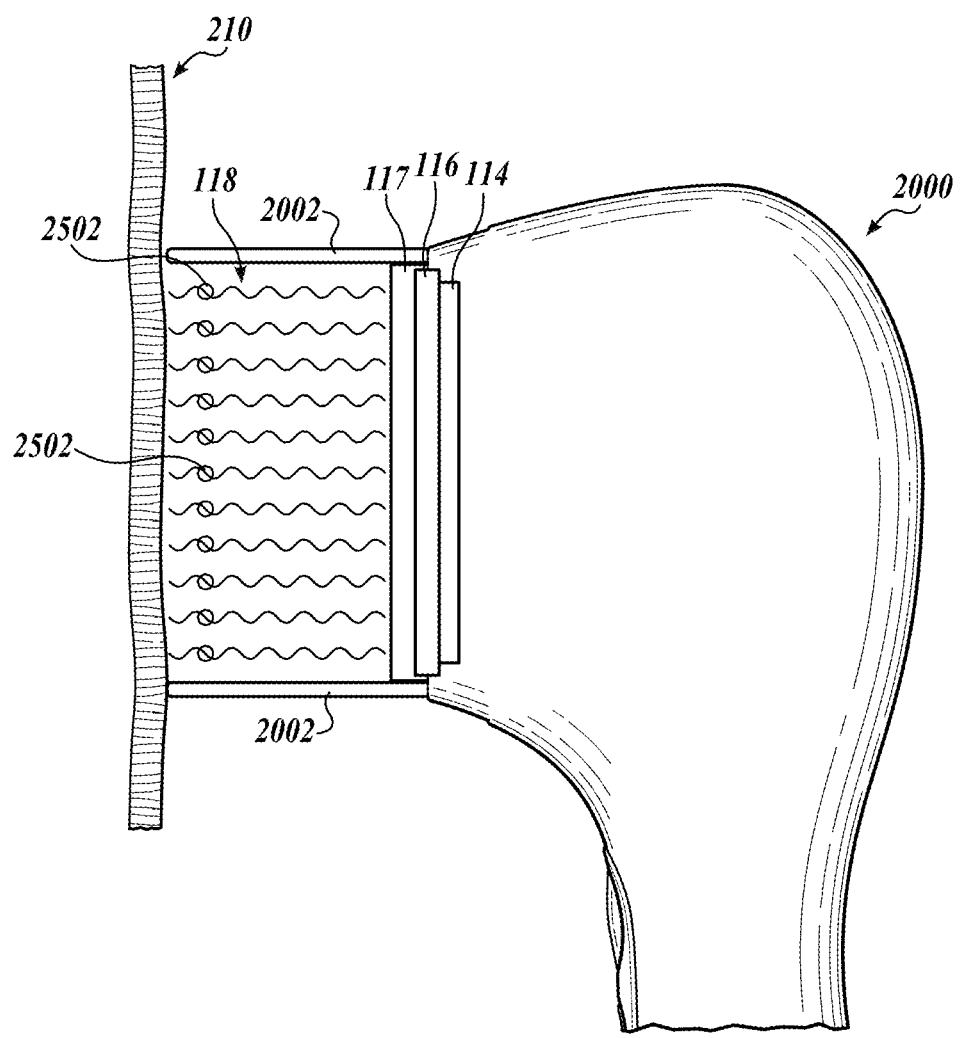
FIG. 34 depicts a side view of a schematic diagram of a cold plasma treatment system in accordance with some embodiments of the present disclosure.

FIG. 34 depicts a side view of a schematic diagram of a cold plasma treatment system in accordance with some embodiments of the present disclosure. Device 2000 is similar to device 2500 except the plurality of electromagnetic field generator units 2502 is disposed closer to the biological surface 210 than cover 117. In FIG. 34, the tips/ends of one or more spaces 2002 are shown in contact with the biological surface 210, which serve to properly position the device 2000 to a target region of the biological surface 210 to be treated with plasma 118 and simultaneously protect one or more components of the device 2000 (e.g., the plurality of electromagnetic field generator units 2502).

In an embodiment, the electromagnetic fields generated by the plurality of electromagnetic field generator units 2502 manipulate at least the free charge species/compounds (e.g., ions, free electrons, charged species, etc.) present within the nominally outputted plasma. In order to facilitate or increase electromagnetic field control of the nominally outputted plasma, the generation of the nominally outputted plasma itself may be optimized to increase or maximize electromagnetic field controllability. This may be achieved, for example, by configuring the plasma generator and/or including supplemental components to generate a higher proportion of free charges. A corona discharge system, for instance, may be used to create more free charge species/compounds in conjunction with the plasma generator.

The plasma generator included in device 2500 or 2000 may comprise devices that generate plasma using mechanisms other than dielectric barrier discharge. A variety of other plasma generation mechanisms can be implemented such as, but not limited to, plasma jets.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, application specific integrated circuit (ASIC), controller or data processor that is specifically programmed, configured or constructed to perform one or more of the computer-executable instructions described above. Of course, any logic or algorithm described herein can be implemented in software or hardware, or a combination of software and hardware.

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Where methods are described, the methods may include more, fewer, or other steps. Additionally, steps may be performed in any suitable order. Accordingly, the disclosure can encompass other embodiments not expressly shown or described herein. In the context of this disclosure, the term "about" means+/−5% of the stated value.

For the purposes of the present disclosure, lists of two or more elements of the form, for example, "at least one of A, B, and C," is intended to mean (A), (B), (C), (A and B), (A and C), (B and C), or (A, B, and C), and further includes all similar permutations when any other quantity of elements is listed.

What is claimed is:

1. A cold plasma system for treating a region of a biological surface, the system comprising:
   a housing;
   an air conduit within the housing;
   a first electrode configured proximately along the air conduit;
   a second electrode configured proximately along the air conduit and opposite from the first electrode;

a source of alternating current (AC) electrically connected with the first electrode, wherein the source of alternating current is configured to generate a cold plasma in the air conduit;

a reservoir configured within the housing, wherein the reservoir is in a fluid communication with the air conduit, and wherein the reservoir is configured for holding the cold plasma; and a cartridge containing a plasma precursor, wherein the cartridge is inserted into the housing, wherein the cartridge is in a fluid communication with the air conduit, wherein the air conduit is a first air conduit connecting the reservoir and the cartridge, the system further comprising:

a first air mover configured to transport the cold plasma from the cartridge through the first air conduit toward the reservoir;

a second air conduit connecting the reservoir and the cartridge;

a second air mover configured to transport the cold plasma back from the reservoir toward the cartridge; and a controller configured to control a speed of rotation of the first air mover and a speed of rotation of the second air mover based on a difference between a present concentration and a target concentration of the cold plasma in the reservoir, wherein the target concentration is selected at least in part based on a half-life of the cold plasma.

2. The system of claim 1, further comprising a third air mover configured to direct the cold plasma out of the cold plasma system, and toward the biological surface.

3. The system of claim 1, wherein the plasma precursor includes precursor components that generate reactive oxygen species or reactive nitrogen species (RONS) in the cold plasma that include at least one of hydroxyl (OH), atomic oxygen (O), singlet delta oxygen (02(1Δ)), superoxide (02-), hydrogen peroxide (H2O2), and nitric oxide (NO).

4. The system of claim 1, further comprising means for controlling a flow of cold plasma, wherein the means are selected from a group consisting of:

a compressible skirt configured to contain the cold plasma proximate to the biological surface;

a face mask configured to contain the cold plasma proximate to the biological surface, wherein a mask intake is in fluid communication with the air conduit; and a plurality of electromagnetic field generator units configured to steer or bend a discharge direction of the cold plasma between a plasma barrier and the biological surface.

5. The system of claim 1, further comprising a compressible skirt configured to contain the cold plasma proximate to the biological surface.

6. The system of claim 1, further comprising a face mask configured to contain the cold plasma proximate to the biological surface, wherein a mask intake is in fluid communication with the air conduit.

7. The system of claim 1, further comprising a plurality of electromagnetic field generator units configured to steer or bend a discharge direction of the cold plasma between a plasma barrier and the biological surface.

* * * * *